(12) United States Patent
Guo et al.

(10) Patent No.: US 10,975,412 B2
(45) Date of Patent: Apr. 13, 2021

(54) METHOD FOR DESIGNING COMPOUNDS AND COMPOSITIONS USEFUL FOR TARGETING HIGH STOICHIOMETRIC COMPLEXES TO TREAT CONDITIONS, INCLUDING TREATMENT OF VIRUSES, BACTERIA, AND CANCERS HAVING ACQUIRED DRUG RESISTANCE

(71) Applicant: UNIVERSITY OF KENTUCKY RESEARCH FOUNDATION, Lexington, KY (US)

(72) Inventors: Peixuan Guo, Columbus, OH (US); Dan Shu, Columbus, OH (US)

(73) Assignee: UNIVERSITY OF KENTUCKY RESEARCH FOUNDATION, Lexington, KY (US)

(*) Notice: Subject to any disclaimer, the term of this patent is extended or adjusted under 35 U.S.C. 154(b) by 828 days.

(21) Appl. No.: 15/572,038

(22) PCT Filed: May 6, 2016

(86) PCT No.: PCT/US2016/031292
§ 371 (c)(1),
(2) Date: Nov. 6, 2017

(87) PCT Pub. No.: WO2016/179531
PCT Pub. Date: Nov. 10, 2016

(65) Prior Publication Data
US 2018/0363021 A1    Dec. 20, 2018

Related U.S. Application Data

(60) Provisional application No. 62/158,114, filed on May 7, 2015.

(51) Int. Cl.
*C12Q 1/00* (2006.01)
*G01N 33/53* (2006.01)
(Continued)

(52) U.S. Cl.
CPC ............ *C12Q 1/025* (2013.01); *C12Q 3/00* (2013.01); *G01N 33/68* (2013.01); *G01N 33/94* (2013.01);
(Continued)

(58) Field of Classification Search
CPC .......... C12Q 1/025; C12Q 3/00; G01N 33/94; G01N 33/68; G01N 2333/195;
(Continued)

(56) References Cited

U.S. PATENT DOCUMENTS

| 2003/0013105 A1 | 1/2003 | Thompson et al. |
| 2004/0083060 A1 | 4/2004 | Church et al. |
| 2007/0269830 A1 | 11/2007 | Superti-Fuga et al. |

FOREIGN PATENT DOCUMENTS

| WO | 2013/192573 | 12/2013 |
| WO | 2015/028994 | 3/2015 |

OTHER PUBLICATIONS

"New approach to develop ultra-high inhibitory drug using the power function of the stoichiometry of the targeted nanomachine or bioconnplex", Nanomedicine (Lond.) (2015) 10(12), 1881-1897 (Year: 2015).*

(Continued)

*Primary Examiner* — Huan H Tran
(74) *Attorney, Agent, or Firm* — Baker Donelson

(57) ABSTRACT

A method is described for the identification of multi-subunit biocomplex drug targets. The method includes identifying a target that performs a biological function, wherein the target comprises one or more subunits, wherein a minimum number of the one or more subunits is inactivated to inhibit the biological function. The method includes selecting a drug that binds specifically to each subunit of the one or more subunits with a target probability. The method describes a relationship between inhibition efficiency of the drug and (Continued)

total number of the one or more subunits using a binomial distribution, wherein the inhibition efficiency comprises a probability that the delivered drug blocks the biological function. The method includes confirming empirically the relationship using an experimental target. The method includes administering the drug to the target to treat a multi-drug resistant disease, wherein the target comprises a biological complex in a mammalian subject.

25 Claims, 51 Drawing Sheets

(51) Int. Cl.
| | | |
|---|---|---|
| *C12Q 1/02* | (2006.01) | |
| *G16B 15/00* | (2019.01) | |
| *G16C 10/00* | (2019.01) | |
| *G16C 20/20* | (2019.01) | |
| *G16C 20/50* | (2019.01) | |
| *C12Q 3/00* | (2006.01) | |
| *G01N 33/68* | (2006.01) | |
| *G01N 33/94* | (2006.01) | |
| *G06G 7/58* | (2006.01) | |

(52) U.S. Cl.
CPC ............... *G06G 7/58* (2013.01); *G16B 15/00* (2019.02); *G16C 10/00* (2019.02); *G16C 20/20* (2019.02); *G16C 20/50* (2019.02); *G01N 33/53* (2013.01); *G01N 2333/005* (2013.01); *G01N 2333/195* (2013.01); *G01N 2333/37* (2013.01); *G01N 2500/00* (2013.01)

(58) Field of Classification Search
CPC ......... G01N 2333/37; G01N 2333/005; G01N 2500/00; G16B 15/00; G16C 10/00; G16C 20/20; G16C 20/50; G06G 7/58; Y02A 90/10
See application file for complete search history.

(56) References Cited

OTHER PUBLICATIONS

International Search Report dated Aug. 11, 20016.
Written Opinion of the ISA dated Aug. 11, 2016.

* cited by examiner

G. MecA-ClpC hexameric ATPase

A. bpFabI Homotetramer

E. Phi29
hexameric pRNA

F.CbbX hexameric ATPase

METHOD FOR DESIGNING COMPOUNDS AND COMPOSITIONS USEFUL FOR TARGETING HIGH STOICHIOMETRIC COMPLEXES TO TREAT CONDITIONS, INCLUDING TREATMENT OF VIRUSES, BACTERIA, AND CANCERS HAVING ACQUIRED DRUG RESISTANCE

This Application Is A § 371 National State Application Of PCT/US2016/031292 Filed May 6, 2016 Which Claims Priority To U.S. Provisional Patent Application Ser. No. 62/158,114, Filed May 7, 2015, The Entire Disclosure Of Which Are Incorporated By Reference In Their Entirety.

GOVERNMENT INTEREST

This invention was made with government support under EB012135. EB003730, and CA151648 awarded by the National Institutes of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

INTRODUCTION

Bacteria, viruses and cells contain biocomplexes and nanomachines composed of multiple subunits, such as biomotors [1,2,3,4], pumps [5], exosomes [6,7,8], valves [9,10,11], membrane pores [12,13,14,15], chaperonins[16], PCNA [17], ATPase [18,19], and tubes [20]. From a nano-biotechnological standpoint, these nanomachines can be used and converted to build sophisticated nano-devices including molecular sensors [21,22,23], patterned arrays, actuators [24], chips, microelectromechanical systems (MEMS) [25], molecular sorters [26], single pore DNA sequencing apparatus [12,13,21,27] or other revolutionary electronic and optical devices [28,29]. From a pharmaceutical standpoint, these multi-subunit biocomplexes or nanomachines have a potential for use as drug targets for therapeutics, as well as diagnostic applications such as pathogen detection, disease diagnosis, drug delivery, and treatment of diseases [22,23,30,31]. In the ASCE (Additional Strand Catalytic E) family including the AAA+ (ATPases Associated with diverse cellular Activities) and the FtsK-HerA superfamily in bacteria, viruses and cells, there are nanomotors that perform a wide range of functions [19,32,33] critical to chromosome segregation, bacterial binary fission, DNA/RNA and cell component transportation, membrane sorting, cellular reorganization, cell division, RNA transcription, as well as DNA replication, riding, repair, and recombination [1,34,35,36]. One of the directions of NIH Roadmap is to utilize these cellular nanomachines and biocomplexes for biomedical applications.

Acquired drug resistance has become a major reason for failure treatment of a range of diseases, i.e., the chemotherapy for cancer, bacterial or viral infections. Drug resistance of cancer has escalated and has partially contributed to the ~600.000 deaths in the USA in 2012 [37]. HIV drug resistance has also become a major issue [38]. Many common pathogens have become resistant to current drug treatments, with new infectious diseases on the rise. The use of multidrug-resistant agents in biological weapons has created a previously unrealized challenge [39]. Thus, there is a need to develop new treatment strategies to combat drug resistance with new drug development methods.

The first FDA-approved drug to treat multidrug-resistant tuberculosis, bedaquiline, follows a new mechanism of inhibiting the bacterial ATP synthase of $M.$ $tuberculosis$ and other mycobacterial species, but had little activity against other bacteria [40]. To combat multidrug resistance in cancer, several approaches have been explored. One method is to target components that are highly important for the growth of the biological entity [41,42]. Another approach uses nano-drug delivery carriers that are expected to enhance the binding efficiency of drugs to cancer cells[43, 44,45,46], or cocktail therapy [47]. A third approach is to develop new combinational drugs with higher potency by acting on multiple targets [48,49]. This involves identifying multiple targets that when treated leads to a synergetic effect and optimizing the design of multi-target ligands[50].

The approach of developing highly potent drugs through targeting protein or RNA complexes with high stoichiometry has never been reported due to challenges in comparing efficacies of two drugs that can be confused by target essentiality with binding affinity. For instance, if two drugs target two stoichiometrically different targets, it becomes extremely difficult to prove whether the difference in drug efficiency is due to differences in their target binding affinity or essential level in the growth of the biological organism. In order to quantify effects from targeting biocomplexes of different stoichiometry, a well-studied multicomponent system is required that allows empirical comparison of functional inhibition of individual components that are composed of different number of subunits.

An example of one nanobiomachine is the dsDNA translocation motor, for which the ATPase protein is a pivotal component that assembles into a hexameric ring structure and translates the action of ATP binding and hydrolysis into mechanical motion to translocate DNA physically. The DNA packaging motor of bacteriophage phi29 (FIG. 1A) [9,51, 52,53] is composed of three essential co-axial rings: 1) a dodecameric connector ring located at the vertex of the viral procapsid; 2) a hexameric packaging RNA (pRNA) ring [52] bound to the N-terminus of the connector [54], and 3) a hexameric ring of ATPase gp16 attached to the helical region of pRNA [10,19,55], powered through the hydrolysis of ATP resulting in DNA packaging. The use of Yang Hui's Triangle (FIG. 1B) or binomial distribution to determine the stoichiometry of the pRNA was first reported in 1997 [56]. The use of similar mathematical methods to determine the stoichiometry of the protein subunits has also been reported more recently [51]. The copy number of ATP molecules required to package one full phi29 genomic dsDNA was predicted to be 10000 [57]. It has recently been shown that this hexameric motor uses a revolution mechanism without rotation to translocate its genomic DNA [10,19,33,35,36,58,59].

Herein, the present inventors propose that the inhibitory efficiency of a drug is related to the stoichiometry of its targeted biocomplex; the higher the stoichiometry of the target complex, the more efficient the drug. This can lead to the development of potent therapeutics against high-stoichiometric biomachines or biocomplexes as drug targets.

This method was employed as described herein by using a mutant subunit as the drugged inactive target to calculate the theoretical inhibition efficiency via binomial distribution, and compared with experimental data from a defined in vitro viral assembly system. Since biomotors share certain common structures and operation mechanisms [1,36,59,60], the approach in drug development reported here has general applications especially in developing new generations of drugs for combating the rising acquired drug resistance in viruses, bacteria, and cancers [38,61,62].

SUMMARY

The presently-disclosed subject matter meets some or all of the above-identified needs, as will become evident to those of ordinary skill in the art after a study of information provided in this document.

Disclosed herein is a method for designing compounds useful for treating conditions that can be treated by targeting high stoichiometric complexes, which is useful, for example, in designing drugs for against in viruses, bacteria, and cancers having acquired drug resistance.

As described herein, Phi29 DNA-packaging motor components were used to test the method for use in connection with targets of different stoichiometries. Virion assembly efficiency was assayed with Yang Hui's Triangle:

$$(p+q)^Z = \sum_{M=0}^{Z} \binom{Z}{M} p^{Z-M} q^M,$$

where Z=stoichiometry, M=drugged subunits in each biocomplex, p and q represent the fraction of drugged and non-drugged subunits in the population.

As reported herein, inhibition efficiency follows a power function. When number of drugged subunits to block the function of the biocomplex K=1, the fraction of uninhibited biocomplex equals $q^Z$. Thus, stoichiometry has a multiplicative effect on inhibition. Tested targets with a thousand subunits showed the highest inhibition effect, followed by those with six and a single subunit. Complete inhibition of virus replication was found when Z=6.

As disclosed herein, drug inhibition potency depends on the stoichiometry of the targeted components of the biocomplex or nano-machine. The inhibition effect follows a power function of the stoichiometry of the target biocomplex.

BRIEF DESCRIPTION OF THE DRAWINGS

The features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A is an Illustration of Phi29 DNA packaging motor composed of 1 copy of genomic DNA that revolves through the channel wall (left panel), 6 copies of pRNA, 6 copies of ATPase gp16 and a connector channel.

FIG. 1B is a Yang Hui Triangle.

FIG. 1C is an illustration of Z=6 and K=1, drug targeting any one subunit of the complex will block its activity.

FIG. 1D is an AFM image of hexameric re-engineered pRNA rings.

FIG. 1E is a 3D structure of hexameric pRNA ring top view and side view from the crystal structure of 3WJ (PDB ID: pRNA 3WJ, 4KZ2).

FIG. 1F is a crystal hexameric structure of AAA+ Protein CbbX withtop view and side view [85] (PDB ID: CbbX, 3Zuh, http://www.ebi.ac.uk/pdbe/emdb/).

FIG. 2A is a gel showing the phi29 genome DNA treated with endonuclease EcoR1.

FIG. 2B is a plot of virion assembly derived from binomial distribution equation 2, which showed that the DNA has stoichiometry of 1.

FIG. 2C is a viral assembly inhibition effect of mutant DNA as model of drugged component with Z=1, showing the linear relationship to p with low slope.

FIG. 3A is the sequence and secondary structure of wild-type pRNA of phi29 DNA packaging motor (upper panel) and inactive mutant pRNA with 4 bases mutation at 5'end of the DNA translocation domain serving as a model of drugged inactive pRNA (lower panel).

FIG. 3B is a fitting the phage assembly inhibition result by inactive mutant pRNA with the theoretical plots derived from Equation 2 matched with Z=6 and K=1.

FIG. 3C compares the viral assembly inhibition effect by drugged pRNA at different concentration with the undrugged pRNA with same dilution factor.

FIG. 4A shows inactivation of pRNA by introducing a 4-nucleotide mutation at the 3'end.

FIG. 4B shows virion production by wild-type phi29 infection using host cell *B. subtilis* harboring plasmid expressing mutant pRNA, wild-type pRNA, or plasmid only.

FIG. 5A shows virion production inhibition effect of mutant gp16 (Z=6) at different concentration.

FIG. 5B shows inhibition efficiency by γ-s-ATP with ATP with high Z value.

FIG. 5C compares the virus assembly inhibition effect by drugged components of DNA, pRNA, gp16 and ATP with stoichiometry of 1, 6, 6, 10000 respectively.

FIG. 7A illustrates a Phi29 DNA packaging motor composed of 1 copy of genomic DNA through a channel composed of three coaxil rings, a 12 subunit connector, 6 subunit pRNA, 6 subunit ATPase gp16.

FIG. 7B shows a binomial distribution equation with its coefficient displayed by Yang Hui Triangle.

FIG. 7C shows an illustration of Z=6 and K=1, drug targeting any subunit of a hexameric complex in blocking its function.

FIG. 10A shows rotation nanomachine DnaB helicase which is a hexamer [69] (PDB ID: 4ESV).

FIG. 10B shows rotation nanomachine RecA motor protein which is a hexamer [72] (PDB ID: 1N03).

FIG. 10C shows revolution Phi29 DNA packaging motor which contains a hexameric pRNA [58].

FIG. 10D shows revolution DNA motor protein FtsK which is a hexamer [87] (PDB ID: 2IUU).

FIG. 11A shows tetrameric bpFabI. Tetrameric bpFabIis a key enzyme in fatty acid synthesis in bacterial, inhibitor PT155 forms a tetrameric complex with BpmFabI [31] (PDB ID: 4BKU).

FIG. 11B shows inosine monophosphate dehydrogenase (IMPDH) [32] (PDB ID: 1AK5). Inosine monophosphate dehydrogenase is a key enzyme in guanine nucleotide biosynthesis pathway, inhibitors have been developed targeting the tetrameric IMPDH.

FIG. 11C shows a bacterial multidrug efflux transporter AcrB which forming a homotrimer[91](PDB ID: 11WG).

FIG. 11D shows a multidrug exporter MexB from *Pseudomonas aeruginosa* forming a homotrimer[92] (PDB ID: 2V50).

FIG. 12A is an Illustration of Phi29 DNA packaging motor composed of 1 copy of genomic DNA that revolves through the channel wall (left panel), 6 copies of pRNA, 6 copies of ATPase gp16 and a connector channel.

FIG. 12B is a Yang Hui Triangle.

FIG. 12C is an illustration of Z=6 and K=1, drug targeting any one subunit of the complex will block its activity.

FIG. 12D is an AFM image of hexameric re-engineered pRNA rings.

FIG. 12E is a 3D structure of hexameric pRNA ring top view and side view from the crystal structure of 3WJ (PDB ID: pRNA 3WJ, 4KZ2).

FIG. 12F is a crystal hexameric structure of AAA+ Protein CbbX with op view and side view (PDB ID: CbbX, 3Zuh, http://www.ebi.ac.uk/pdbe/emdb/).

FIG. 13A is a gel showing the phi29 genome DNA treated with endonuclease EcoR1.

FIG. 13B is a plot of virion assembly derived from binomial distribution equation 2, which showed that the DNA has stoichiometry of 1.

FIG. 13C is a viral assembly inhibition effect of mutant DNA as model of drugged component with Z=1, showing the linear relationship to p with low slope.

FIG. 14A is the sequence and secondary structure of wild-type pRNA of phi29 DNA packaging motor (upper panel) and inactive mutant pRNA with 4 bases mutation at 5' end of the DNA translocation domain serving as a model of drugged inactive pRNA (lower panel).

FIG. 14B is a fitting the phage assembly inhibition result by inactive mutant pRNA with the theoretical plots derived from Equation 2 matched with Z=6 and K=1.

FIG. 14C compares the viral assembly inhibition effect by drugged pRNA at different concentration with the undrugged pRNA with same dilution factor.

FIG. 15A shows inactivation of pRNA by introducing a 4-nucleotide mutation at the 3'end.

FIG. 15B shows virion production by wild-type phi29 infection using host cell *B. subtilis* harboring plasmid expressing mutant pRNA, wild-type pRNA, or plasmid only.

FIG. 16A shows virion production inhibition effect of mutant gp16 (Z=6) at different concentration.

FIG. 16B shows inhibition efficiency by γ-s-ATP with ATP with high Z value.

FIG. 16C compares the virus assembly inhibition effect by drugged components of DNA, pRNA, gp16 and ATP with stoichiometry of 1, 6, 6, 10000 respectively.

DESCRIPTION OF EXEMPLARY EMBODIMENTS

Figure 1A:
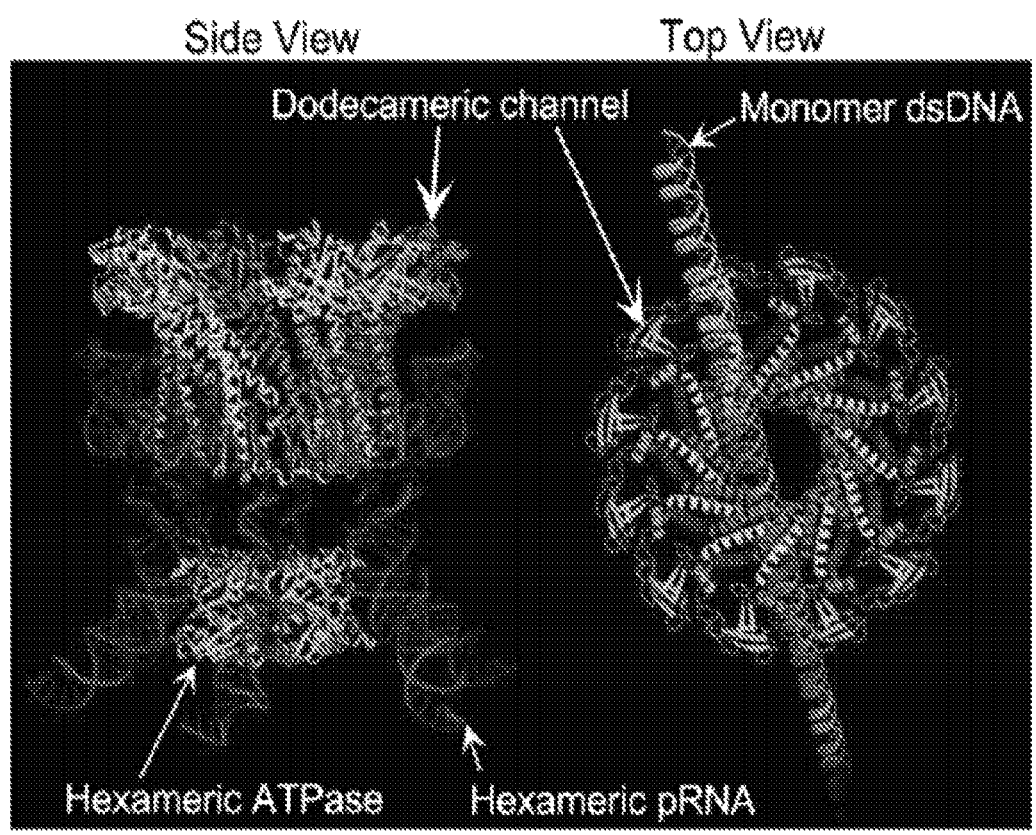
FIGS. 1A-1F show the stoichiometry of viral DNA packaging motor
Figure 1B:
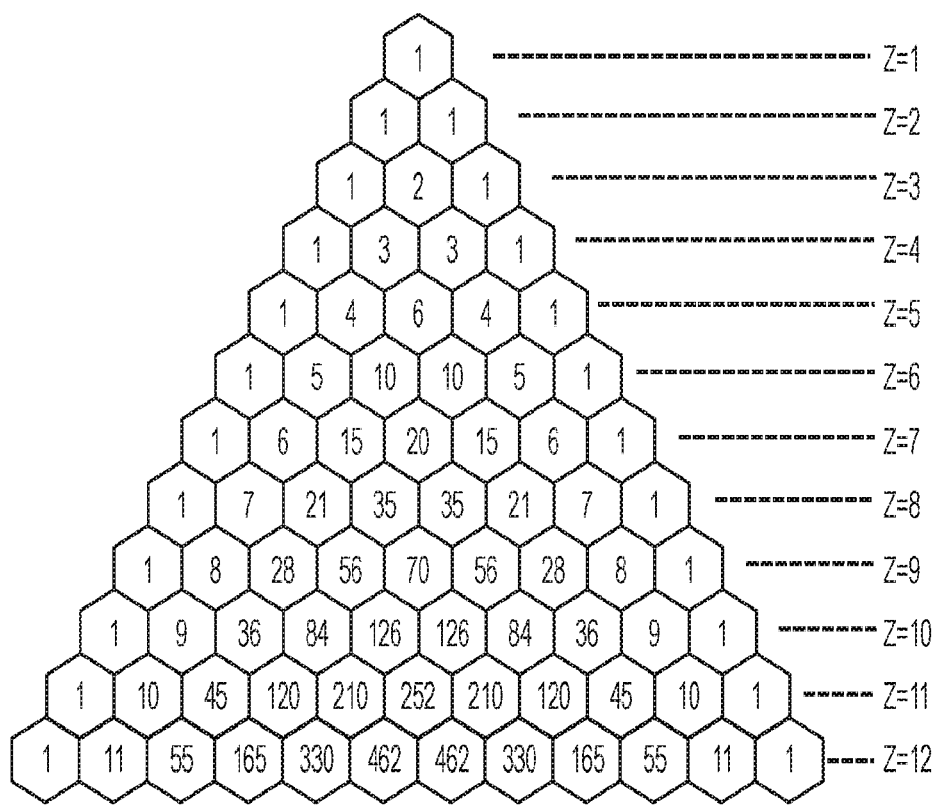

The disclosure below includes Section 1 (which includes the Introduction set forth above and description of FIGS. 1-6), Section 2 (which includes description of FIGS. 7-11 set forth above), and Section 3 (which includes the description of FIGS. 12-17 set forth above). Each section discloses systems, devices, and methods for designing compounds and compositions as further described below.

Section 1

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes a method for designing a compound or composition for treatment of virus, bacteria, or cancer having acquired drug resistance, which involves identifying a multi-subunit bio complex of the virus or bacteria that is distinct from other biocomplexes in the subject species, or selecting a multi-subunit bio complex of the cancer containing a mutation; and designing a drug to target subunit of the biocomplex. The present inventors have surprisingly determined that the inhibitory efficiency of a drug is related to the stoichiometry of its targeted biocomplex; the higher the stoichiometry of the target complex, the more efficient the drug.

This can lead to the development of potent therapeutics against high-stoichiometric biomachines or biocomplexes as drug targets. This method was employed as described herein by using a mutant subunit as the drugged inactive target to calculate the theoretical inhibition efficiency via binomial distribution, and compared with experimental data from a defined in vitro viral assembly system.

The approach in drug development reported here has general applications especially in developing new generations of drugs for combating the rising acquired drug resistance in viruses, bacteria, and cancers.

Disclosed herein is a method for designing compounds useful for treating conditions that can be treated by targeting high stoichiometric complexes, which is useful, for example, in designing drugs for against in viruses, bacteria, and cancers having acquired drug resistance.

$$(p+q)^Z = \sum_{M=0}^{Z} \binom{Z}{M} p^{Z-M} q^M,$$

where Z=stoichiometry, M=drugged subunits in each biocomplex, p and q represent the fraction of drugged and non-drugged subunits in the population.

Disclosed herein are methods for designing and/or identifying compounds useful for treating conditions that can be treated by targeting high stoichiometric complexes, which is useful, for example, in designing and/or identifying drugs for/against viruses, bacteria, and cancers having acquired drug resistance. In some embodiments, the compounds designed or identified herein may be an antibody, an antisense oligonucleotide, miRNA, a short hairpin RNA, a small peptide, and the like directed to a component or subunit of the nanomachines (e.g., biomotors or biocomplexes) contemplated herein. Other agents that could be used to bind the target compound include: protein, aptamer, LNA, chemical compounds and Polysaccharide.

In one embodiment, methods are provided for the identification of multi-subunit biocomplex drug targets. In one embodiment, the method comprises (a) identifying a target that performs a biological function, wherein the target comprises one or more subunits, wherein a minimum number of the one or more subunits is inactivated to inhibit the biological function; (b) selecting a drug that binds specifically to each subunit of the one or more subunits with a target probability, wherein the target probability comprises a common probability for each subunit that the drug delivered to the target inactivates the subunit; (c) describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number; (d) confirming empirically the relationship using an experimental target, wherein the target includes the experimental target; and (e) contacting the drug to the target to treat a multi-drug resistant disease, wherein the target comprises a biological complex in a mammalian subject. In a further embodiment, the mammalian subject is administered the drug identified or designed according to the methods of the invention.

In one embodiment, methods are provided for increasing inhibition efficiency of a multimeric biocomplex. In one embodiment, the method comprises (a) identifying a target that performs a biological function, wherein the target comprises one or more subunits, wherein a minimum number of the one or more subunits is inactivated to inhibit the biological function; (b) selecting a drug that binds specifically to each subunit of the one or more subunits with a target probability, wherein the target probability comprises a common probability for each subunit that the drug delivered to the target inactivates the subunit; (c) describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number; (d) confirming empirically the relationship using an experimental target, wherein the target includes the experimental target; and (e) contacting the drug to the target to treat a multi-drug resistant disease, wherein the target comprises a biological complex in a mammalian subject. In a further embodiment, the mammalian subject is administered the drug identified or designed according to the methods of the invention.

In one embodiment, methods are provided for optimizing biocomplex stoichiometry-based drug development. In one embodiment, the method comprises (a) identifying a target that performs a biological function, wherein the target comprises one or more subunits, wherein a minimum number of the one or more subunits is inactivated to inhibit the biological function; (b) selecting a drug that binds specifically to each subunit of the one or more subunits with a target probability, wherein the target probability comprises a common probability for each subunit that the drug delivered to the target inactivates the subunit; (c) describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number; (d) confirming empirically the relationship using an experimental target, wherein the target includes the experimental target; and (e) contacting the drug to the target to treat a multi-drug resistant disease, wherein the target comprises a biological complex in a mammalian subject. In a further embodiment, the mammalian subject is administered the drug identified or designed according to the methods of the invention.

In one embodiment, methods are provided for targeting a high stoichiometry biocomplex to increase drug targeting efficiency. In one embodiment, the method comprises (a) identifying a target that performs a biological function, wherein the target comprises one or more subunits, wherein a minimum number of the one or more subunits is inactivated to inhibit the biological function; (b) selecting a drug that binds specifically to each subunit of the one or more subunits with a target probability, wherein the target probability comprises a common probability for each subunit that the drug delivered to the target inactivates the subunit; (c) describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number; (d) confirming empirically the relationship using an experimental target, wherein the target includes the experimental target; and (e) contacting the drug to the target to treat a multi-drug resistant disease, wherein the target comprises a biological complex in a mammalian subject. In a further embodiment, the mammalian subject is administered the drug identified or designed according to the methods of the invention.

In one embodiment, methods are provided for treating a subject afflicted with a multi-drug resistant disease. In one embodiment, the method comprises: (a) identifying a target that performs a biological function, wherein the target comprises one or more subunits, wherein a minimum number of the one or more subunits is inactivated to inhibit the biological function; (b) selecting a drug that binds specifically to each subunit of the one or more subunits with a target probability, wherein the target probability comprises a common probability for each subunit that the drug delivered to the target inactivates the subunit; (c) describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number; (d) confirming empirically the relationship using an experimental target, wherein the target includes the experimental target; and (e) contacting the drug with the target to treat a multi-drug resistant disease, wherein the target comprises a biological complex in a mammalian subject. In a further embodiment, the mammalian subject is administered the drug identified or designed according to the methods of the invention.

In some embodiments of the invention, the experimental target comprises a component or subunit of a multimeric biocomplex. Non-limiting examples of a multimeric biocomplex include a receptor, a channel, an enzyme, and a transporter. In other embodiments, the experimental target comprises a component or subunit of a biological nanomotor. Non-limiting examples of a biological nanomotor include a linear motor, a rotation motor, and a revolution motor. In further embodiments, the biological nanomotor further comprises an ATPase component. In some embodiments, the biological nanomotor is a bacteriophage Phi29 DNA packaging motor. As discussed herein, the bacteriophage Phi29 DNA packaging motor comprises a genomic dsDNA component, a packaging RNA component, an ATPase gp16 component, an ATP component, or a combination thereof.

In one embodiment, the biological motor or multimeric biocomplex is homomeric. In another embodiment, the biological motor or the multimeric biocomplex comprises a dimer, a hetero-oligomer, or a homo-oligomer. In some embodiments, the number of components or subunits comprising the biological motor or multimeric biocomplex is at least 2, 3, 4, 5, 6, 7, 8, 9, 10, 20, 30, 40, 50, 60, 70, 80, 90, or 100. In some embodiments, the number of components or subunits comprising the biological motor or multimeric biocomplex is at least 100, 200, 300, 400, 500, 600, 700, 800, 900, 1000, 2000, 3000, 4000, 5000, 6000, 7000, 8000, 9000, or 10,000. In some embodiments, the number of components or subunits comprising the biological motor or multimeric biocomplex is at least 2, 3, 4, 5, 6, 7, 8, 9, 10, 11, or 12. For example, the bacteriophage Phi29 DNA packaging motor comprises 1 copy of genomic dsDNA, and such copy comprises a subunit (e.g., 1 target subunit). For example, the bacteriophage Phi29 DNA packaging motor comprises 6 copies of packaging RNA, and such copies comprise subunits (e.g., 6 target subunits). For example, the bacteriophage Phi29 DNA packaging motor comprises 6 copies of gp16, and such copies comprise subunits (e.g., 6 target subunits). For example, the bacteriophage Phi29 DNA packaging motor comprises 10,000 copies of ATP, and such copies comprise subunits (e.g., 10.000 target subunits).

As used herein and as is well understood in the art, "treatment" is an approach for obtaining beneficial or desired results, including clinical results. Beneficial or desired clinical results can include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also refer to prolonging survival as compared to expected survival if not receiving treatment.

The term "in need thereof" refers to the need for symptomatic or asymptomatic relief from a condition associated with multi-drug resistance, such as, for example, a cancer, and/or a condition associated with a multi-drug resistant disease caused by a multidrug-resistant organism. The subject in need thereof may or may not be undergoing treatment for conditions related to, for example, a cancer, and/or a condition associated with a multi-drug resistant disease caused by a multidrug-resistant organism. In some embodiments, the subject is a mammalian subject. In some embodiments, the mammalian subject is a human, a dog, a cat, a bird, a pig, a horse, or a cow. In certain embodiments, the mammalian subject is a human.

A multi-drug resistant disease can be caused by a multi-drug-resistant organism. The multidrug resistant organism is no longer responsive to an antibiotic composition treatment, an antifungal composition treatment, an antiviral composition treatment, or an antiparasitic composition treatment. In one embodiment, the multidrug-resistant organism is a bacterium, a fungus, a virus, or a parasite. Non-limiting examples of a multidrug-resistant bacterium include a species of *staphylococcus*, a species of *enterococcus*, a species of *gonococcus*, a species of *streptococcus*, a species of *acinetobacter*, a species of *enterobacter*, a species of *klebsiella*, a species of *salmonella*, a species of *escherichia*, a species of *pseudomonas*, and a species of *mycobacterium*. Non-limiting examples of a multidrug-resistant fungus include a species of *candida* and a species of scedosporium. Non-limiting examples of a multidrug-resistant virus include HIV, influenza, cytomegalovirus and herpes simplex virus. Non-limiting examples of a multidrug-resistant parasite include a species of *plasmodium*, a species of *toxoplasma*, and a species of *ascaris*.

The present disclosure relates generally to small molecule therapeutics useful the treatment of a multi-drug resistant cancer or a multi-drug resistant disease caused by a multi-drug-resistant organism. In one embodiment, a drug identified or designed according to the methods described herein is administered to a subject to prevent or treat diseases or disorders associated with a multi-drug resistant cancer or a multi-drug resistant disease caused by a multidrug-resistant organism. In one embodiment, an effective amount of the drug identified or designed according to the methods described herein is administered to the subject. In some embodiments, the drug identified or designed according to the methods described herein comprises a pharmaceutical composition administered to a subject in a pharmaceutically acceptable carrier. In some embodiments, the drug identified or designed according to the methods described herein can serve as a therapeutic method for the treatment of a multi-drug resistant cancer or a multi-drug resistant disease caused by a multidrug-resistant organism.

Embodiments of the invention may be used to treat a multi-drug resistant cancer or a multi-drug resistant disease caused by a multidrug-resistant organism Non-limiting examples of diseases, disorders, and/or illnesses which may benefit from embodiments of the present invention may include illnesses caused by Vancomycin-Resistant Enterococci, tuberculosis, pneumonia, illnesses caused by Methicillin-Resistant *Staphylococcus aureus*, cancer, food poisoning, legionnaire's disease, yeast infections, malaria, and helminthiasis.

The drug identified or designed according to the methods described herein can be utilized in pharmaceutical compositions by adding an effective amount of a compound to a suitable pharmaceutically acceptable diluent or carrier. Use of the drug compounds and methods of the invention may also be useful prophylactically.

An "effective amount". "sufficient amount" or "therapeutically effective amount" as used herein is an amount of a composition that is sufficient to effect beneficial or desired results, including clinical results. As such, the effective amount may be sufficient, for example, to reduce or ameliorate the severity and/or duration of an affliction or condition, or one or more symptoms thereof, prevent the advancement of conditions related to an affliction or condition, prevent the recurrence, development, or onset of one or more symptoms associated with an affliction or condition, or enhance or otherwise improve the prophylactic or therapeutic effect(s) of another therapy. An effective amount also includes the amount of the composition that avoids or substantially attenuates undesirable side effects.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in Remington: The Science and Practice of Pharmacy, 21st Edition (University of the Sciences in Philadelphia, ed., Lippincott Williams & Wilkins 2005); and Handbook of Pharmaceutical Excipients, 7th Edition (Raymond Rowe et al., ed., Pharmaceutical Press 2012); each hereby incorporated by reference in its entirety.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. A pharmaceutically acceptable carrier can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Any conventional media or agent that is compatible with the active compound can be used. Supplementary active compounds can also be incorporated into the compositions. For oligonucleotide compounds, examples of pharmaceutically acceptable salts and their uses are further described in U.S. Pat. No. 6,287,860, which is hereby incorporated by reference in its entirety.

Embodiments of the present invention can be administered alone, or can be administered in a therapeutic cocktail or as a pharmaceutical composition. For example, a pharmaceutical composition can comprise embodiments of the present invention, and a saline solution that includes a phosphate buffer. Embodiments of the present invention can be administered using the means and doses described herein. Embodiments of the present invention can be administered in combination with a suitable carrier. In one embodiment, the drug identified or designed according to the methods described herein encompass any pharmaceutically acceptable salts, esters, or salts of such esters, or any other compound which, upon administration to a subject, provides (directly or indirectly) the biologically active metabolite or residue thereof.

A pharmaceutical composition of the invention is formulated to be compatible with its intended route of administration. Examples of routes of administration include parenteral, (e.g., intravenous), intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EM™ (BASF, Parsippany. N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or Lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the harrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

Formulations useful for topical administration include those in which the drug identified or designed according to the methods described herein are in admixture with a topical delivery agent such as lipids, liposomes, fatty acids, fatty acid esters, steroids, chelating agents and surfactants. Exemplary lipids and liposomes include neutral (e.g. diolcoyl-phosphatidyl ethanolamine (DOPE), dimyristoylphosphatidyl choline (DMPC), distearolyphosphatidyl choline) negative (e.g. dimyristoylphosphatidyl glycerol (DMPG)) and cationic (e.g. diolcoyltetramethyl-aminopropyl (DOTAP), and diolcoyl-phosphatidyl ethanolamine (DOTMA)). For topical or other administration, the drug identified or designed according to the methods described herein can be encapsulated within liposomes or can form complexes thereto, in particular to cationic liposomes. Alternatively, the drug identified or designed according to the methods described herein can be complexed to lipids, in particular to cationic lipids. Exemplary fatty acids and esters, pharmaceutically acceptable salts thereof, and their uses are further described in U.S. Pat. No. 6,287,860, which is hereby incorporated by reference in its entirety.

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of the drug identified or designed according to the methods described herein, and can generally be estimated based on EC50s found to be effective in in vitro and in vivo animal models. In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 350 mg/kg body weight, at least about 400 mg/kg body weight, at least about 450 mg/kg body weight, or at least about 500 mg/kg body weight.

In one embodiment, the drug identified or designed according to the methods described herein can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof. For example, the dosage may be given once or more daily, weekly, monthly or yearly, or even once every 2 to 20 years. In one embodiment, two or more combined the drug identified or designed according to the methods described herein, therapeutics, and the like may be used together in combination or sequentially. The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the drug identified or designed according to the methods described herein is administered in maintenance doses, ranging from at least about 0.1 mg/kg body weight to about 10 mg/kg of body weight, from at least about 0.1 mg/kg body weight to about 20 mg/kg of body weight, from at least about 0.1 mg/kg body weight to about 30 mg/kg of body weight, from at least about 0.1 mg/kg body weight to about 40 mg/kg of body weight, from at least about 0.1 mg/kg body weight to about 50 mg/kg of body weight, from at least about 0.1 mg/kg body weight to about 60 mg/kg of body weight, from at least about 0.1 mg/kg body weight to about 70 mg/kg of body weight, from at least about 0.1 mg/kg body weight to about 80 mg/kg of body weight, from at least about 0.1 mg/kg body weight to about 90 mg/kg of body weight, from at least about 0.1 mg/kg body weight to about 100 mg/kg of body weight, once or more daily, to once every 2-20 years.

While the terms used herein are believed to be well understood by those of ordinary skill in the art, certain definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Although any methods, devices, and materials similar or equivalent to those described herein can be used in the practice or testing of the presently-disclosed subject matter, representative methods, devices, and materials are now described.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

Unless defined otherwise, all technical and scientific terms used herein have the same meaning as is commonly understood by one of skill in the art to which the invention(s) belong. All patents, patent applications, published applications and publications, GenBank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

Following long-standing patent law convention, the terms "a", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The terms "animal," "subject," and "patient" as used herein includes all members of the animal kingdom including, but not limited to, mammals, animals (e.g., cats, dogs, horses, swine, etc.) and humans.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Materials and Methods
Preparation of Mutant Genomic dsDNA

Phi29 genomic DNA-gp3 was purified from *B. subtilis* SpoA12 cells by CsCl gradient ultracentrifugation as described previously [63]. Mutant dsDNA was prepared by digesting the phi29 genomic dsDNA with EcoR1 restriction enzyme in fast digest buffer (Fermentas) at 37° C. for 1 hour followed by ethanol precipitation. The mutant DNA was tested by 1% agarose gel electrophoresis, stained by ethidium bromide (Sigma) and imaged by Typhoon (GE).

Preparation of Mutant pRNA

Wild-type phi29 pRNA and inactive mutant as drugged pRNA were prepared by in vitro transcription. In the inactive mutant pRNA, the first four bases "UUCA" (SEQ ID NO: 1) located at the 5' end were mutated to "GGGG" (SEQ ID NO: 2). BglII digested plasmid pRT71 was used as DNA template [64] in the PCR reaction for both RNAs. Oligonucleotide 5'-TAA TAC GAC TCA CTA TAG GGG TGG TAC-3' (SEQ ID NO: 3) and 5'-TTA TCA AAG TAG CGT GCA C-3'(SEQ ID NO: 4) were used as primers for mutant pRNA. RNAs were then transcribed by T7 RNA polymerase using double-stranded DNA generated from PCR, as described before [65]. The RNA from in vitro transcription was further purified by 8 M urea 8% polyacrylamide gel electrophoresis as described previously [64].

Preparation of Mutant ATPase Gp16

The purification of wild-type gp16 has been described previously [63]. The walker B mutant gp16 was constructed by introducing mutations in the gp16 gene. The amino acid residues D255 and E256 in walker B motif of gp16 were mutated to E255 and D256, respectively. The mutation was introduced with the Stratagene Quick Change site-directed mutagenesis kit using appropriate primers. The expression and purification of protein were carried out followed a published procedure [51].

Antisense Oligonucleotides

Antisense oligonucleotides P3 and P15 were designed to be reversely complementary to different regions on the pRNA molecule and chemically synthesized by IDT. P3 oligo (5'-TTGCCATGATTGACAAC-3' (SEQ ID NO: 5)) targets the region of 83-99 nucleotides at the 3'end of pRNA, P15 oligo (5'-AAGTACCGTACCATTGA-3' (SEQ ID NO:

6)) targets the region of 1-17 nucleotides at the 5'end of pRNA. P8 oligo (5'-TAATACGACTCAC-TATAGGGGTGGTAC-3 (SEQ ID NO: 7)) was designed as a non-targeting control in the test. 1 µl of individual oligos at 100 µM were mixed with 1 µl of pRNA at 4 µM and dialyzed on a 0.025 µm mixed cellulose esters VSWP filter membrane (Millipore Corp) against TBE buffer (89 mM Tris-HCl, pH 8.3, 89 mM boric acid, 2.5 mM EDTA) at room temperature for 15 min. The purified RNA complex was used for in vitro phi29 assembly assay.

In Vitro Phi29 Assembly Assay

Purified components were subjected to in vitro viral assembly assay as described previously [66]. Briefly, 10 µg of purified procapsids were mixed with 100 ng of pRNA in 5 µl of reaction buffer (10 mM ATP, 6 mM 2-mercaptoethanol, and 3 mM spermidine in TMS buffer) at room temperature for 30 min. Purified DNA-gp3 and gp16 were then added and the reaction mixture was incubated at room temperature for one hour to initiate DNA packaging. Finally, the DNA filled procapsids were incubated with 10 µl of gp8.5-9 extract from E. coli containing plasmid pARgp8.5-9 and 20 µl of gp11-14 extract from E. coli to complete the infectious phage assembly.

The newly assembled infectious viruses were plated with inoculated B. subtilis bacteria Su$^{+44}$ cells onto a half LB plate covered with top agar. After 12 hour incubation at 37° C., the viral assembly efficiency (plaque-forming unit, PFU) was calculated by counting the formed plaque numbers. Mixing different ratios of mutant with wild-type components, while keeping all other components the same, the viral assembly efficiency (PFU) versus ratio of mutant components gave an empirical curve for vial assembly inhibition assay, and it was compared with theoretical curves from the binomial distribution equation.

In Viva Viral Assembly Assay

Plasmid pRBwtRNA containing the pRNA coding sequence under T7 promoter was constructed by ligating the fragment coding pRNA sequence and T7 promoter into pRB381-L550 vector (modified and kindly provided by M. Wang and H Zalkin) following a previously described method [67]. Plasmid pRBmutRNA contained mutant pRNA under its natural promoter PE1 sequence, and the mutation was changing sequence 5'UUGA-3' (SEQ ID NO: 8) at its 3'end to 5'GGGG-3' (SEQ ID NO: 9). The DNA fragments coding mutant pRNA sequence and PE1 sequence were prepared by PCR as described previously[67]; and digested with HindIII-BglII restriction enzyme. The mutant pRNA sequence coding fragment was further ligated with a 6.0 kb fragment from pRB381-L550 that was digested with HindIII and partially digested with BglII.

The plasmids pRBmutRNA, pRBwtRNA, and pRB381-L550 were transformed into B. subtilis cells following methods described previously [67]. The B. subtilis cells harboring transformed plasmids were incubated in 416 medium with 10 mg/ml of neomycin for 3 hours at 37° C. and then plated onto LB-neomycin (10 mg/ml) plates for plaque formation analysis.

Results

The Definition of "Stoichiometry".

The definition of the stoichiometry in this report is different from conventional definition of stoichiometry used to evaluate drug efficiency. Conventionally the concept of stoichiometry refers to the number of a drug binding to each target molecule, which is also known as $B_{max}$. In this study the definition of stoichiometry refers to the copy number of subunit within a biocomplex or the nanomachine that serves as drug target.

The Definition of "K Value", and K=1 is One Key for Ultra-High Inhibition Efficacy Suppose a biocomplex drug target contains Z copies of subunits, then K is the copy number (K≤Z) of drugged subunits required to inhibit the function of the complex or the nanomachine. As an analogy to the difference between the parallel circuit and the serial circuit, when the Christmas lights are arranged in a parallel circuit, any light bulbs that are burnt out will not affect other bulbs. But in a serial circuit, any one light bulb that is broken will stop the entire lighting system, which is K=1. Thus, the K value is the key to the probability of inactive nanomachines or biocomplexes by combination and permutation of all subunits. K equals 1 is critical for such ultra-high inhibition effect. The foundation of the approach in this report is the difference in probability of inhibited biocomplexes in systems of different K values with combination and permutation algorithms. Biological systems display complicated reactions. Many reactions involve multiple subunits to work cooperatively sequentially or processively to accomplish one essential biological function [33,68,69,70,71,72,73,74,75]. Single assembly pathways have been reported in the viral assembly system [76,77]. In most cases of the sequential, cooperative, and processive action, inactivation of any one, not necessary all, of the subunits will result in inhibition of its function, thus K=1. Drug synergism was utilized in multi-target drug therapy; in short, a drug combination can simultaneously act on multiple targets in disease networks to produce a synergistic effect [50,78]. However, our design reported here is unique from the conventional synergistic approach. We suggest that using multi-subunit biocomplexes as drug target could lead to development of ultra-high potent drugs. In a conventional six-component system, for example one drug is designed to target component #3 to stop the entire system, since the drug can only target component #3, the condition fits the model of Z=1 and K=1. Thus, the inhibition efficiency and substrate targeting efficiency (p) of drug will be in linear relationship. However, in the system in this report, the entire system will be blocked when drug targets any subunit of a hexamer, which is Z=6 and K=1. Thus the probability of remaining undrugged targets will be $q^6$, where q represents the fraction of untargeted hexamer subunits; in other words, the drug inhibition efficiency will be $1-q^6$, which increases following a power function compared to the linear for conventional mono-subunit approaches.

Figure 1C:
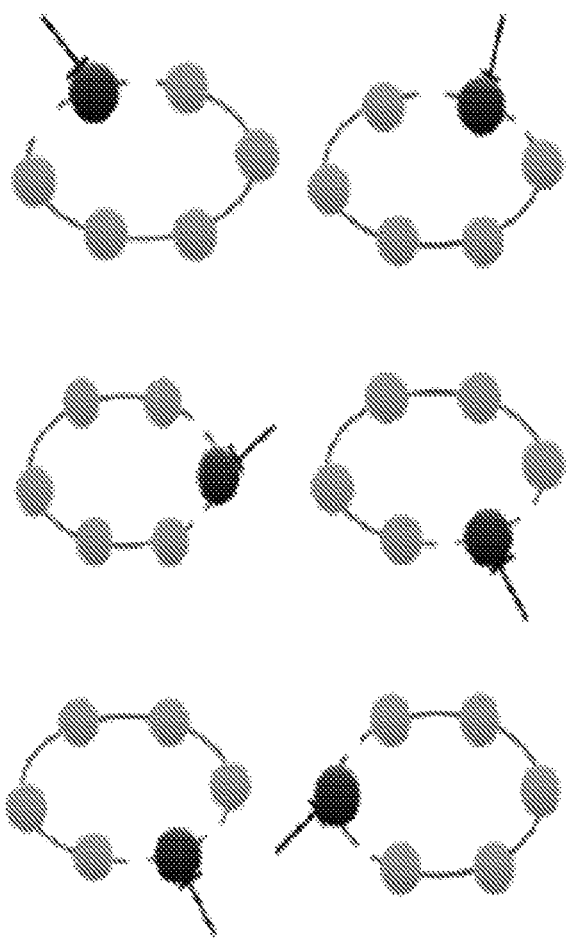
Figure 1D:
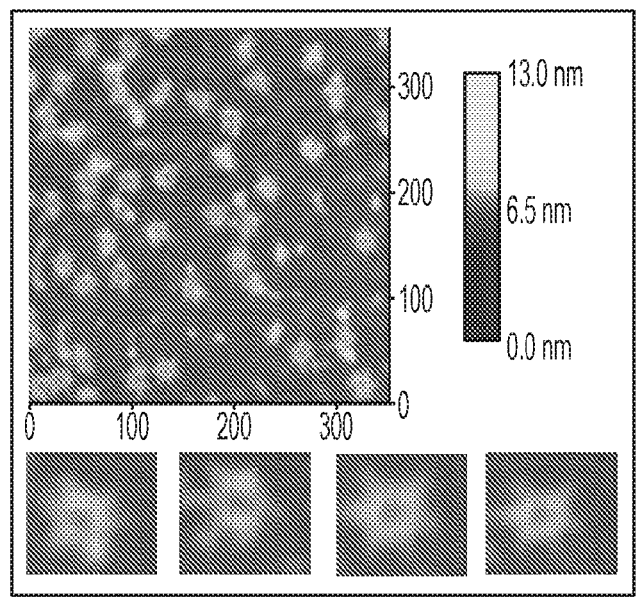
Figure 1D:
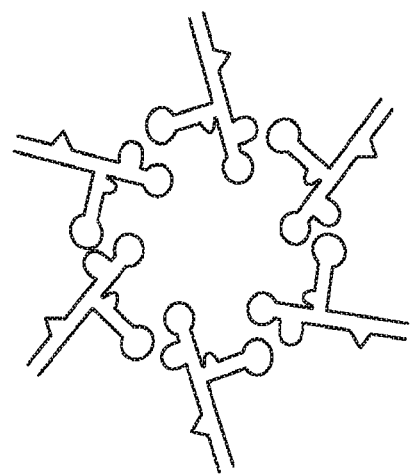
Figure 1E:
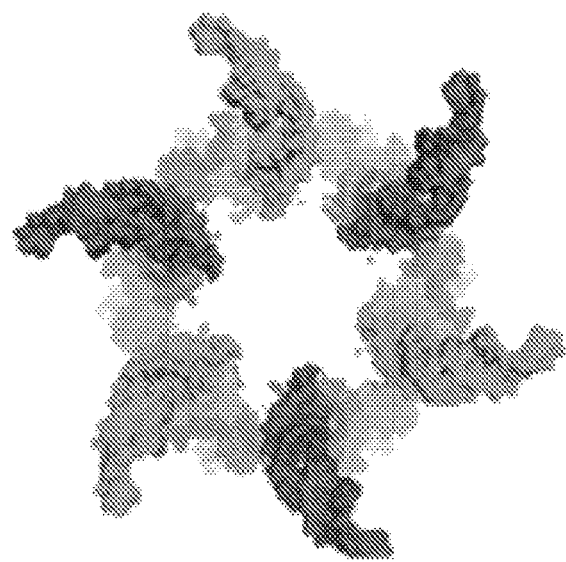
Figure 1E:
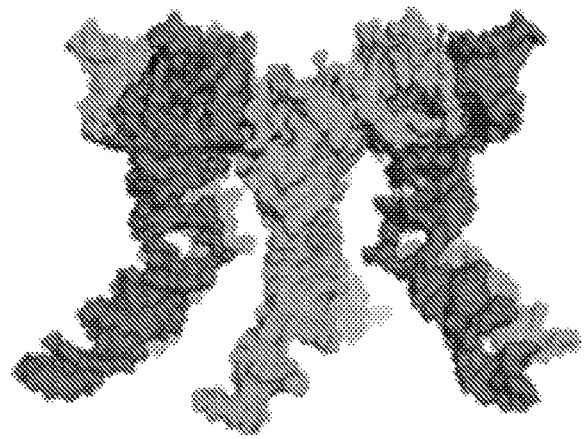
Figure 1F:
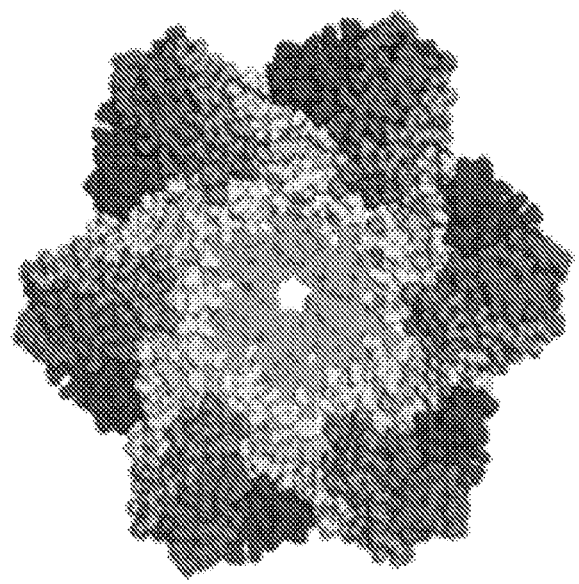
Figure 1F:
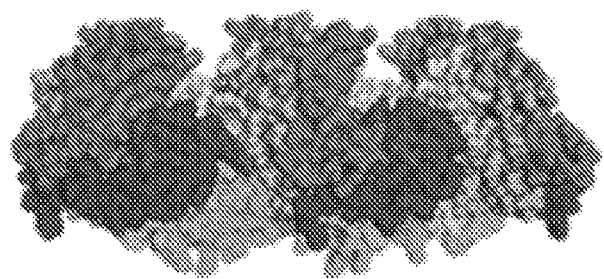
Figure 1G:
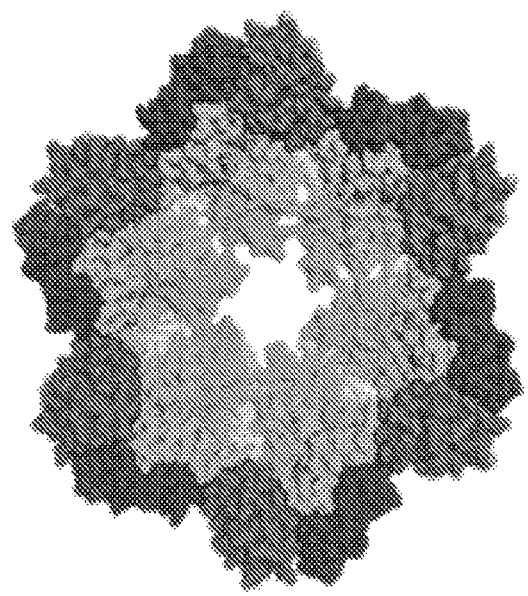
FIG. 1G is a structure of the hexameric AAA+ molecular machine ClpC with adaptor protein MecA. [86] (PDB ID: MecA-ClpC, 3PXG).
Figure 1G:
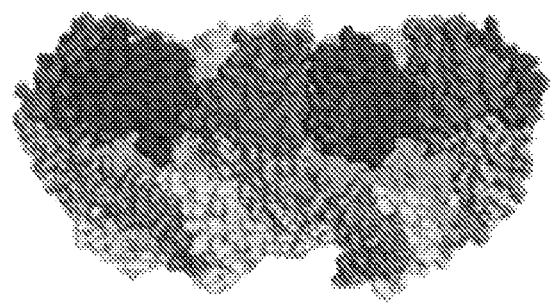

Assuming that at least K copies of drugged subunits were needed to deactivate the nanomachine or biocomplex, the probability of functional biocomplexes in the presence of various ratios of inhibited and wild-type subunits could be predicted from equation 2. When K=1, it implies that drug binding to one subunit will inactivate the subunit, and one drugged subunit per multi-subunit complex is sufficient to inhibit the overall function of the complex. The inhibition efficiency by drugs targeting multi-subunit biocomplexes with stoichiometry of Z will equal $1-q^z$, as shown in table 2. An example for such a probability calculation when Z=6 and K=1 is as follows: since it was assumed that 6 (Z=6) copies of subunits per element were required for function and one drugged subunit (K=1) was sufficient to block its activity, all elements possessing 1 to 5 copies of drugged subunits would be non-functional (FIG. 1C). Only those complexes possessing 6 copies of normal subunits will be functional. The chance for a complex containing 6 copies of unaffected subunits in a population is $q^6$ and the inhibition efficiency will be $1-q^6$.

Rationale Behind Selection of Multi-Subunit Biocomplexes as Efficient Drug Targets Mechanisms for drug inhibition of organism growth are to block or stop an essential biological element from functioning. When a drug is designed to target the subunit of a complex with targeting efficiency p, a fraction of subunits will not interact with the drug (a percentile given as g, p+q=1) and will remain active and exert their function properly. Some biological elements are monomers containing only one subunit, while other biological elements, such as the bio-motors of hexameric AAA+ family, consist of multiple-subunits [19,34]. Conventional drugs are designed to inhibit pathogenesis through targeting of a single subunit molecule, such as an enzyme or a structural protein of a virus. In this situation, the inhibition efficiency is proportional to the substrate targeting efficiency p and the effect is proportional to the first order of p. As described above, in most cases of sequential action or cooperatives in multiple subunit complexes, inactivation of one, not all, of the subunits will result in inhibition of its function. Thus, if complexes containing Z copies of subunits exercise their function in a sequential and cooperative way, then K=1, and the fraction of the uninhibited active biocomplex will be $q^Z$, a higher order with regards to the stoichiometry. The inhibition proportion will equal $1-q^Z$.

In this investigation, a well-defined in vitro phi29 viral assembly system was used to represent a multi-subunit nano-machine target, with the mutant component representing a target component that have been inactivated by an effective drug. Then, the inhibition efficiencies by targeting different elements of the phi29 DNA packaging motor with different stoichiometry were compared. The viral assembly competition assays combined with binomial distribution analysis illustrated the concept that drug targeting functional biological complexes of a higher-stoichiometry has a higher efficiency than drug acting on a single subunit target.

When the target element is a monomer containing only one subunit, the inhibition efficiency can be calculated through a binomial distribution (equation 1), where p and q are the fractions of drugged (substrate targeting efficiency) and undrugged (normal active elements) subunits, respectively (p+q=1).

$$X=(p+q)^1 \quad (1)$$

However, when the target element contains multiple subunits, a high order binomial distribution (equation 2) is applied to calculate the drug inhibition effect by finding the ratio of resulted active and inactive complexes, where Z represents the total number of subunits (the stoichiometry) in one biocomplex and M represents the number of drugged subunits in one biocomplex.

$$X = (p+q)^Z = \sum_{M=0}^{Z} \binom{Z}{M} p^{Z-M} q^M = \sum_{M=0}^{Z} \left( \frac{Z!}{M!(Z-M)!} \right) p^{Z-M} q^M \quad (2)$$

Note that the binomial distribution as set forth in equation 2 may also be expressed as follows:

$$\sum_{M=0}^{Z} \binom{Z}{M} p^M q^{Z-M} = \sum_{M=0}^{Z} \left( \frac{Z!}{M!(Z-M)!} \right) p^M q^{Z-M}$$

Computational results based on the binomial equation are set forth herein. The context of the results governs which form of the equation is used.

For example, if Z is 3, the probability of all combinations of drugged subunits (M) and undrugged subunits (N; M+N=Z) in a given biocomplex entity can be determined by the expansion of equation 2: $(p+q)^3=p^3+3p^2q+3pq^2+q^3=1$. That is, the probability of a complex element possessing three copies of drugged subunits in the population is $p^3$, two copies of drugged and one copy of undrugged or wild-type subunit is $3p^2q$, one copy of drugged and two copies of undrugged subunits is $3pq^2$, and three copies of undrugged subunits is $q^3$. Assuming there were 70% (p=0.7) of subunits inactivated by bound drugs, and 30% (q=0.3) unaffected subunits in the population, then the percentage of elements possessing at least two copies of normal subunits would be the sum of those possessing one copy of drugged and two copies of undrugged wild-type subunits, $3pq^2$, and those possessing three copies of native subunits is $q^3$. That is $3pq^2+q^3=3(0.7)(0.3)^2+(0.3)^3=0.216=21.6\%$. In another example, if one complex contains 6 subunits, and 5 out of the 6 subunits need to remain uninhibited in order to be biologically functional, the active complex ratio in the population will be the sum of: 1) the probability of each element containing 5 undrugged subunits, and 2) the probability of each element containing 6 undrugged subunits.

The probability X in the population displaying a certain combination of undrugged versus drugged subunits can be predicted by a binomial distribution, as shown in equation 2. Table 1 shows the probability of a given element with M drugged and N undrugged subunits at increasing percentages of drugged subunits in the population, considering that the total subunits in one element (Z) is 3 or 12. The formula, $$\frac{Z!}{M!N!} p^M q^N$$

(from equation 2) was used to calculate each combination probability value, the coefficient $$\frac{Z!}{M!N!}$$

in this equation can also be calculated using Yang Hui Triangle, which is also called Pascal's Triangle, or binomial distribution (FIG. 1B)[79].

In Vitro Virus Assembly System Used for Testing the Hypothesis

The highly sensitive in vitro phi29 assembly system was used to determine the inhibition efficiency of drugs targeting multi-subunit complexes [56,66,76,80]. Bacteriophage phi29 DNA packaging motor contains one copy of genomic dsDNA, 6 copies of packaging RNA, 6 copies of ATPase protein gp16 and more than 10000 copies of ATP. The stoichiometry of RNA in phi29 has been proven by extensive studies including single-molecule studies[81] AFM images (FIG. 1D) [82,83], pRNA crystal structure determination (FIG. 1E) [84], and mathematical studies [56]. The stoichiometry of gp16 in phi29 has been proven by multiple approaches including native gel binding, capillary electrophoresis assays, Hill constant determination, and by titration of mutant subunits using binomial distribution [19,33]. Many other AAA+ superfamily members have been found to be hexamers as well [85,86,87,88,89,90,91], such as a red type rubisco activase AAA+ protein CbbX (FIG. 1F) [85], MecA-ClpC molecular machine (FIG. 1G)[86]. The copy number of ATP molecules was calculated based on the fact that 6 ATP molecules are required to package one pitch of dsDNA with 10.5 basepairs (bp) [92], thus 1 ATP is used to package 1.7 bp. The entire phi29 genome is composed of 19.4 kbp, thus, it is expected that more than 10000 ATP molecules are required to package the entire phi29 genome. The phi29 DNA nano-motor which packages an entire genomic DNA into the procapsid can be treated as a disease model for drug inhibition efficiency analysis.

In Vitro Testing of the Hypothesis Using DNA Element with Stoichiometry of 1

Figure 2A:
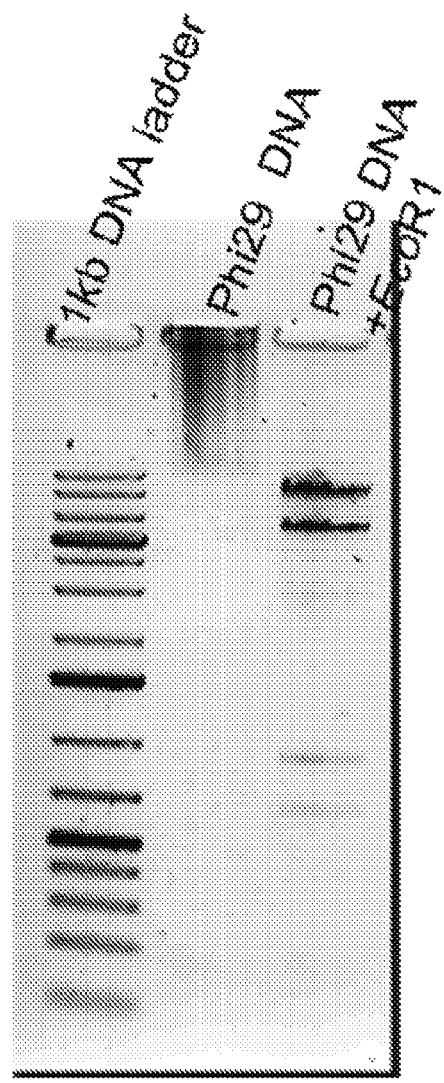
FIGS. 2A-2C show a theoretical plot (with variable Z) and empirical data illustrate inhibition efficiency with drug targeting to genomic DNA (Z=1).
Figure 2B:
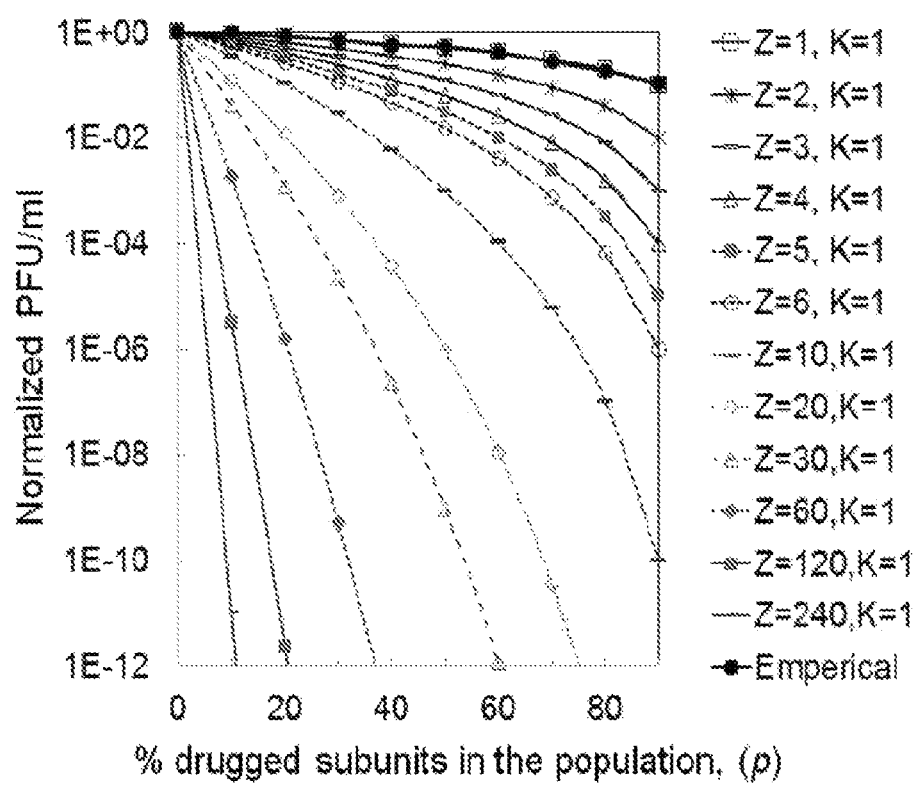
Figure 2C:
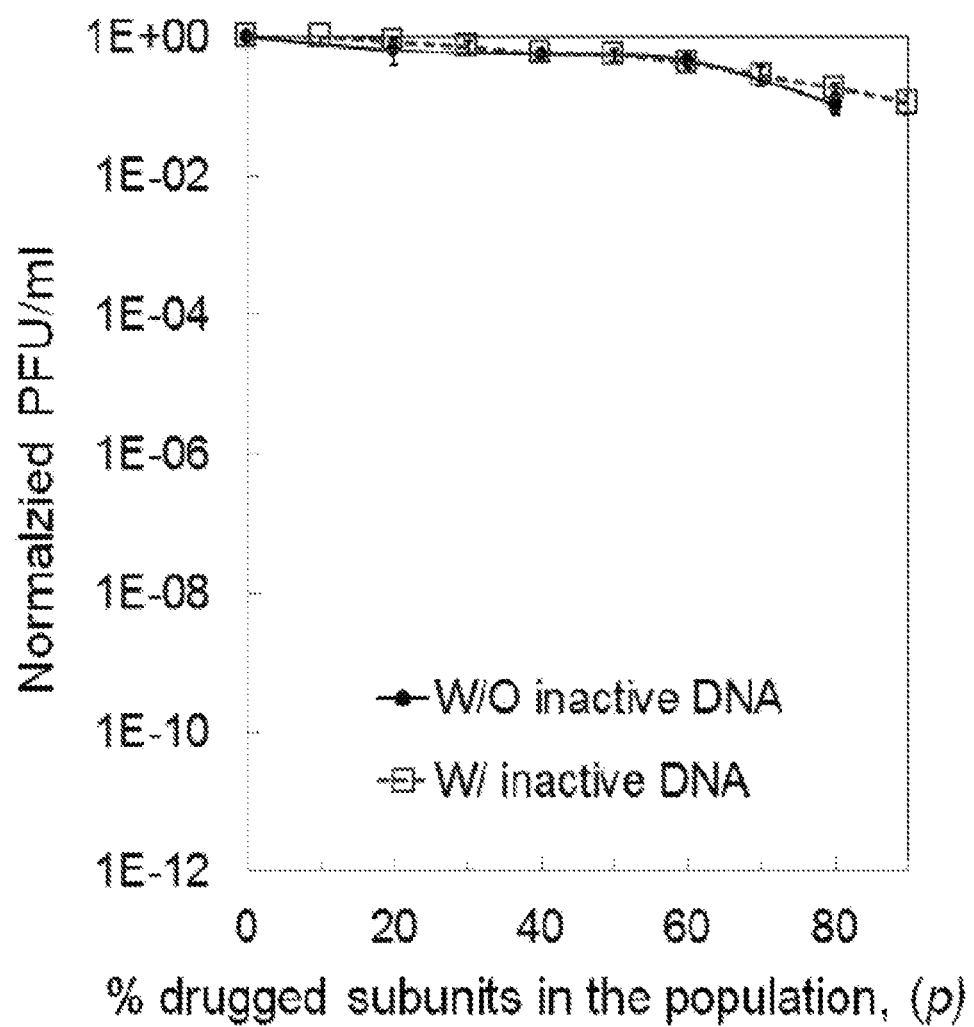

The inhibition efficiency of drugs targeting a single subunit substrate was tested by in vitro phi29 assembly inhibition by mutating the genomic dsDNA (FIG. 2A). Various ratios of mutant DNA were mixed with wild-type DNA in in vitro viral assembly assays. The empirical curve of viral assembly efficiency against drugged mutant DNA ratio fits well with the theoretical curve from binomial distribution for Z=1 and K=1 (FIG. 2B). This suggests that when designing drug targeting the genomic DNA in phi29 nano-motor, it is expected to be a first order inhibition response. Comparing the in vitro phi29 assembly inhibition, by adding drugged mutant DNA, with simply diluting wild-type DNA concentration as a control, revealed that the drugged mutant DNA didn't cause much difference (FIG. 2C). The results showed that the inhibition effect of drugs targeting the substrate with stoichiometry of 1 is minimal.

In Vitro Testing of the Hypothesis Using RNA Elements with Stoichiometry of 6

Figure 3A:
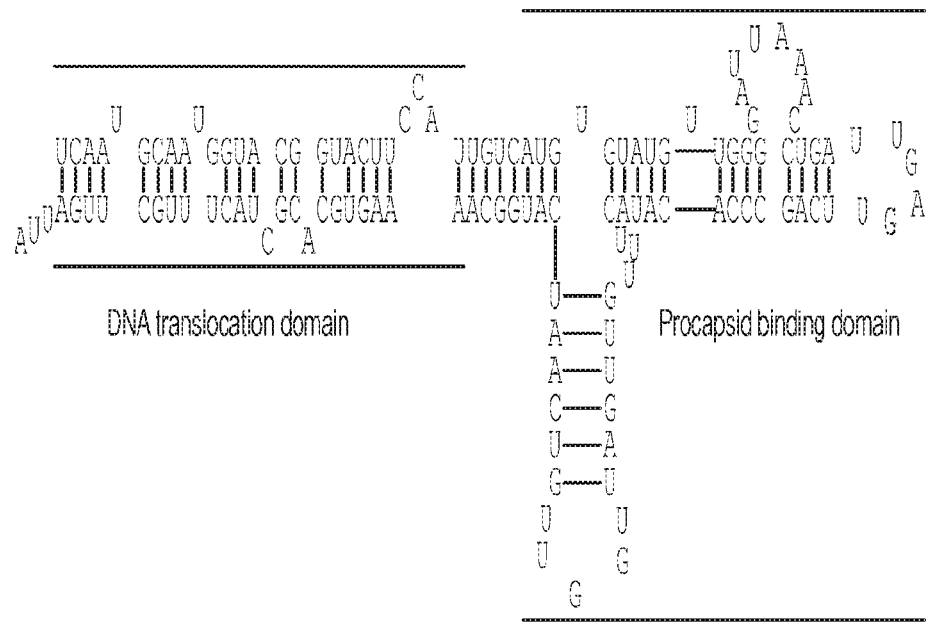
FIGS. 3A-3C is a theoretical plot (K=1 to 6) and empirical data to illustrate inhibition efficiency with drug targeting pRNA (Z=6).
Figure 3A:
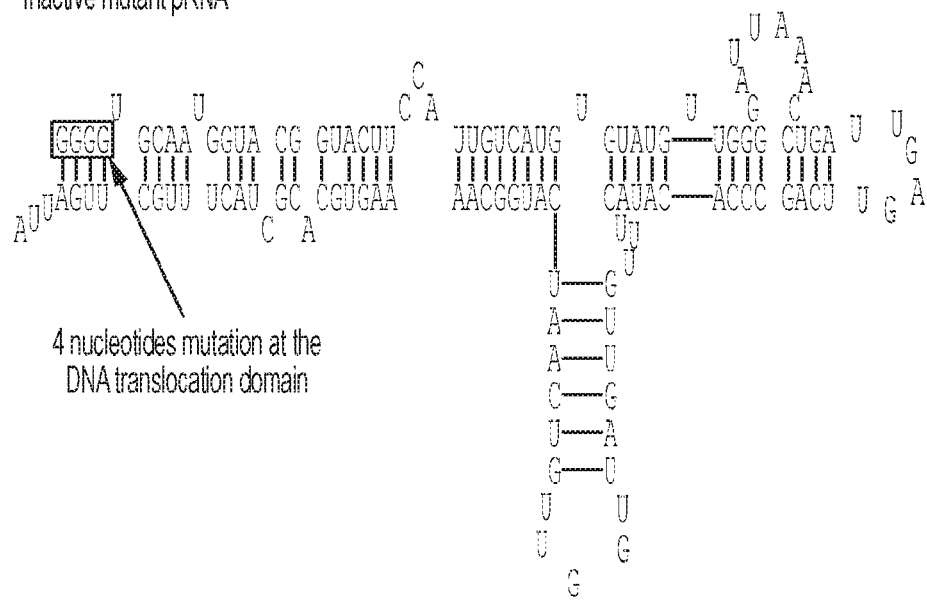
Figure 3B:
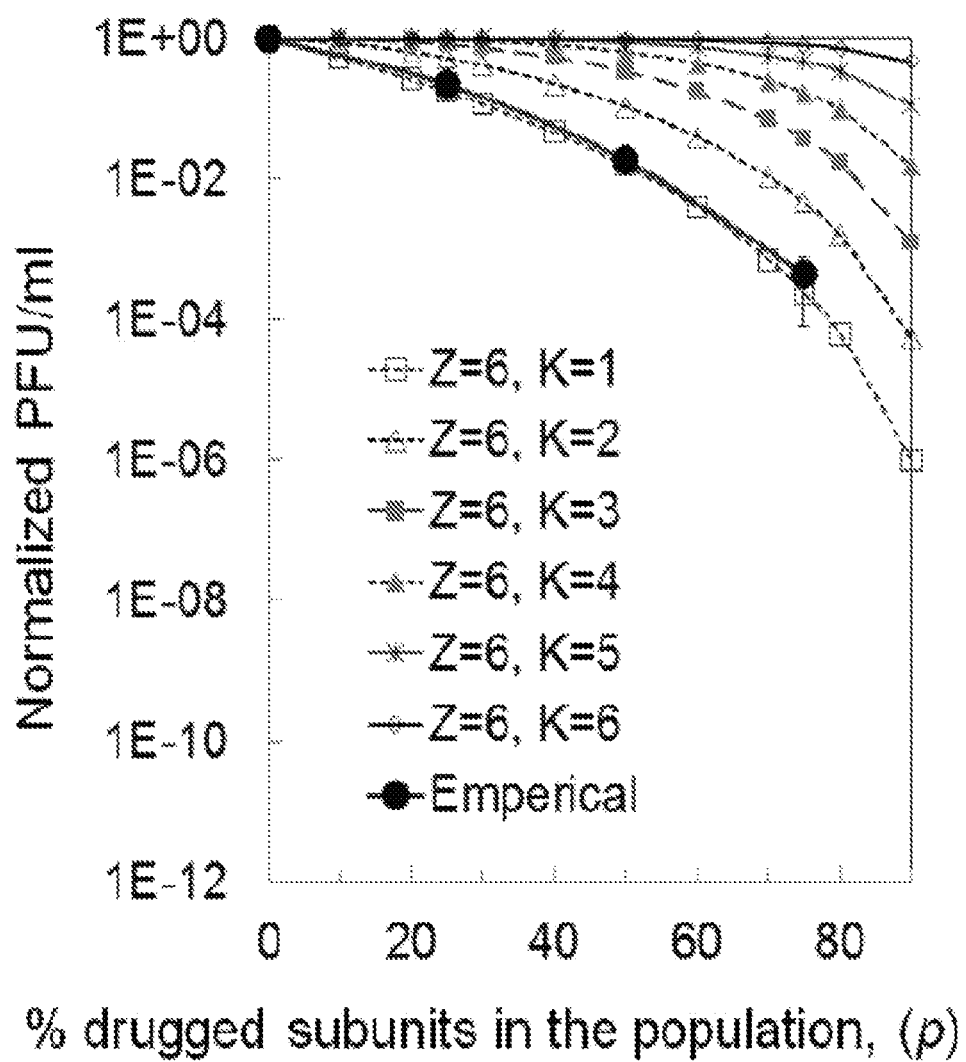
Figure 3C:
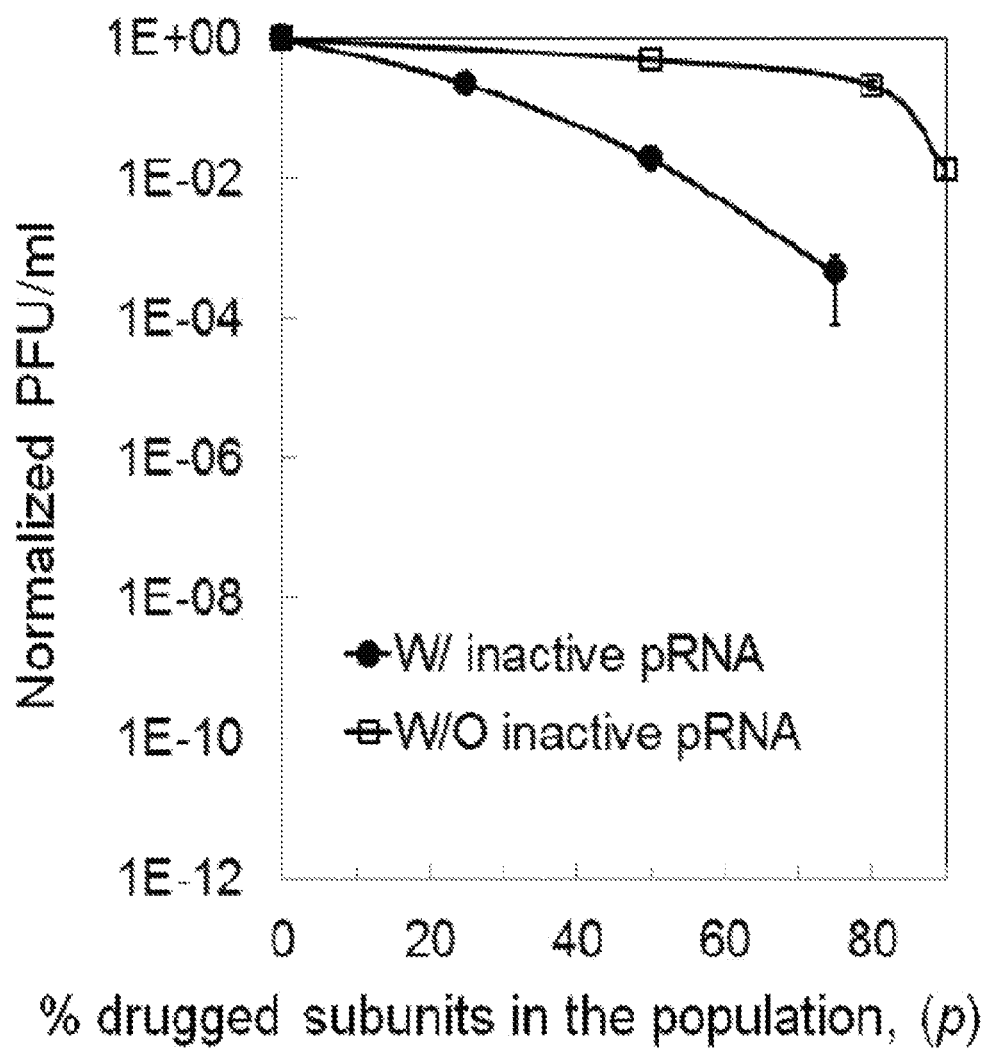

The pRNA of phi29 contains two domains; a head-loop domain essential for procapsid binding and a helix domain essential for DNA translocation (FIG. 3A, upper panel) [30,93,94]. The right-hand loop and left-hand loop of two pairing pRNA molecules can interact with each other by complementary base pairing. Extensive studies have led to the conclusion that 6 copies of pRNA form a hexameric ring which binds to the procapsid for virus activity [81,82,83,84]. Drugged mutant pRNA was constructed by mutating 4 nucleotide sequences at the 5'end region of pRNA (FIG. 3A, lower panel), which has been shown to compete with wild-type pRNA for procapsid binding, hut was found to be deficient in allowing DNA packaging to occur [67]. The theoretical curves generated using the expansion of binomial distribution equation while total subunit number Z is 6 and varying K number from 1 to 6 are shown in FIG. 3B. Fitting the empirical data from phage assembly efficiency at different ratios of drugged mutant pRNAs into the theoretical curves, the empirical data fit into the theoretical curve of Z=6 and K=1. It suggested that the pRNA oligomer ring is composed of six copies of pRNA subunits and one subunit of the pRNA multimer blockage is sufficient to block the phage assembly activity. Comparing the empirical curve for viral assembly efficiency against different ratios of drugged mutant pRNAs with the wild-type pRNA concentration dilution control, addition of drugged mutant pRNA showed a much stronger inhibition effect (FIG. 3C).

To further prove the concept that drugs targeting biocomplex with high stoichiometry causes stronger inhibition effect, antisense oligonucleotides which can bind to pRNA molecules were designed as mock drugs in the viral assembly assay. The oligonucleotides P15, and P3 were designed to target the 5'-end and 3'-end regions on pRNA, respectively. It was confirmed that the antisense oligonucleotides can be hybridized to pRNA by gel shift assay (data not shown). When mixing the antisense oligonucleotides with wild-type pRNA for in vitro phi29 assembly assay, complete inhibition effects were shown by antisense oligonucleotides P15, and P3, but not with the non-targeting control oligonucleotide P8[95]. By mixing the non-targeting oligo P8 with pRNA, it generated plaques with $4.4 \times 10^6$ PFU on the plate.

In Vivo Testing of the Hypothesis Using RNA Elements with Stoichiometry of 6

Figure 4A:
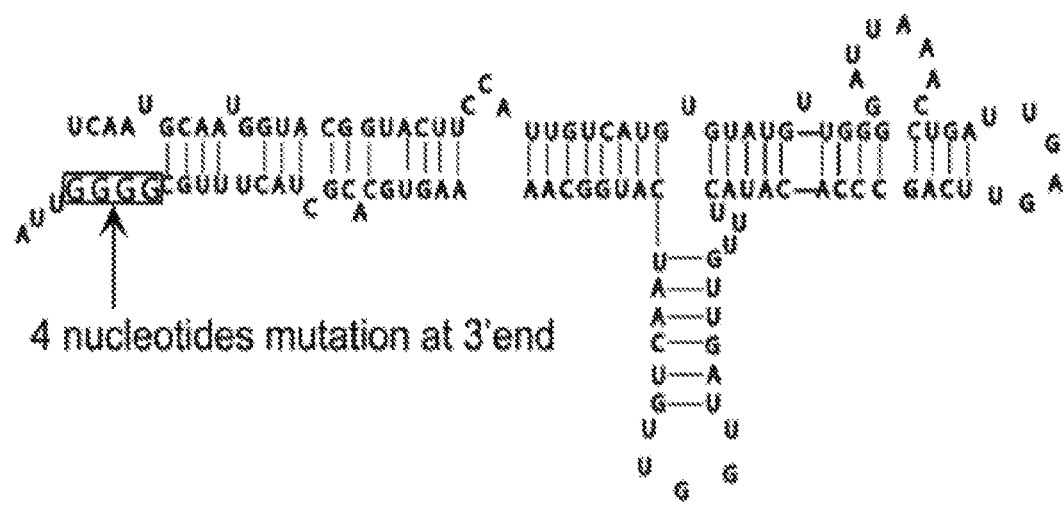
FIGS. 4A-4B shows complete inhibition of viral assembly in vivo by mutant pRNA as a model of drugged complex (Z=6).
Figure 4B:
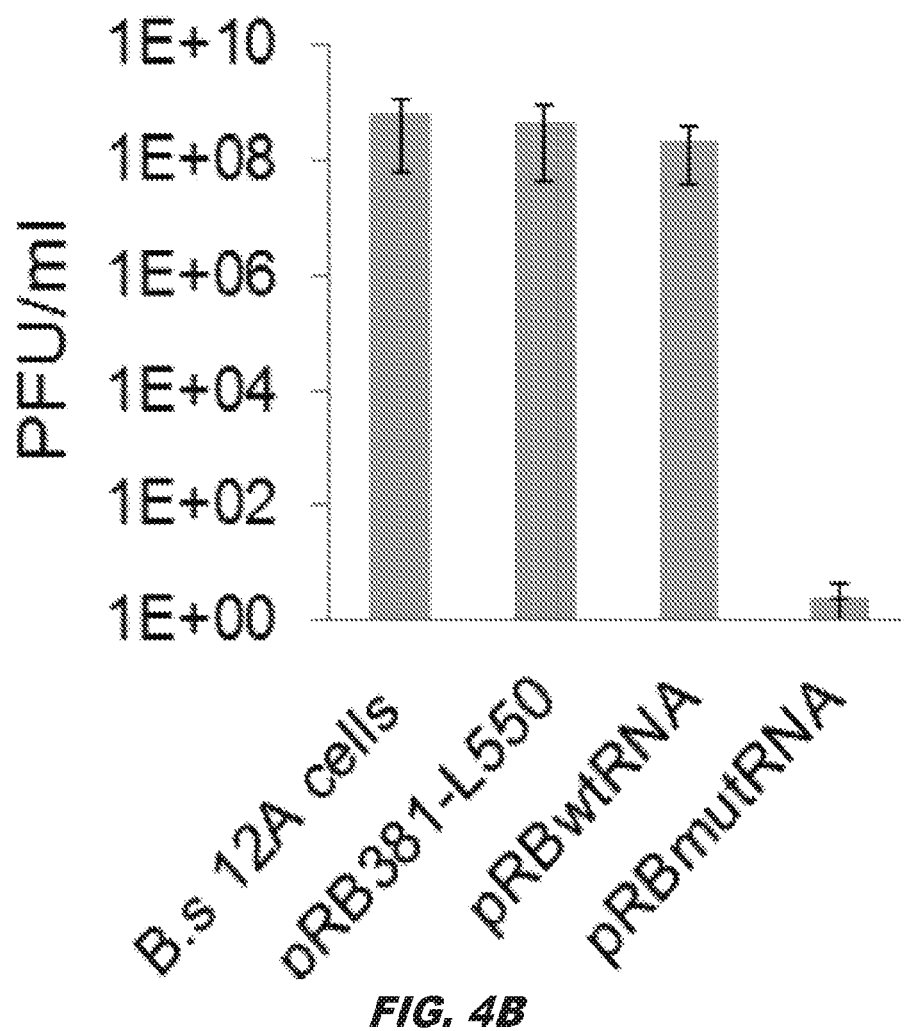

Formation of the hexameric ring of pRNA in the phi29 dsDNA packaging motor has been discovered through biochemical and structural studies [52,81,84,96,97,98,99,100, 101,102,103] and activity assays [94,104]. The observed high inhibition efficiency by drugged mutant pRNA on phi29 assembly in vitro was striking [67,105]. To test whether such a high level of inhibition was attainable in vivo, pRBmutRNA plasmid expressing a pRNA with 4-base mutation at the 3' end (FIG. 4A) was transformed into *B. subtilis* DE1 cells. Plasmid pRBwtRNA contained the pRNA coding sequence but do not express pRNA in *B. subtilis* DE1 cells, and vector pRB381-L550 was introduced as well as a negative control. The results showed that only cells harboring pRBmutRNA plasmid were completely resistant to plaque formation by wild-type phi29 virus infection. Control cells, including *B. subtilis* 12A cells alone, *B. subtilis* DE1 cells carrying vector pRB381-L550 alone, and cells carrying a wild-type pRNA coding sequence but no expression plasmid pRBwtRNA were all positive for plaque formation (FIG. 4B). The ability of mutant pRNAs generated in cells by plasmid pRBmutRNA completely inhibited plaque formation indicated that hexameric pRNA in DNA packaging nano-motor may be a potential target for developing potent antiviral agents [67].

In Vitro Testing of the Hypothesis Using the ATPase with Stoichiometry of 6

Hexameric folding of ATPase gp16 protein in the phi29 dsDNA packaging motor has been discovered [1,19,33,35]. The hexameric gp16 protein complex functions as ATPase like many other AAA+ superfamily members. ATP binding to one subunit of gp16 stimulates the ATPase to change its conformation from having a lower affinity to one having a higher affinity for dsDNA.

Figure 5A:
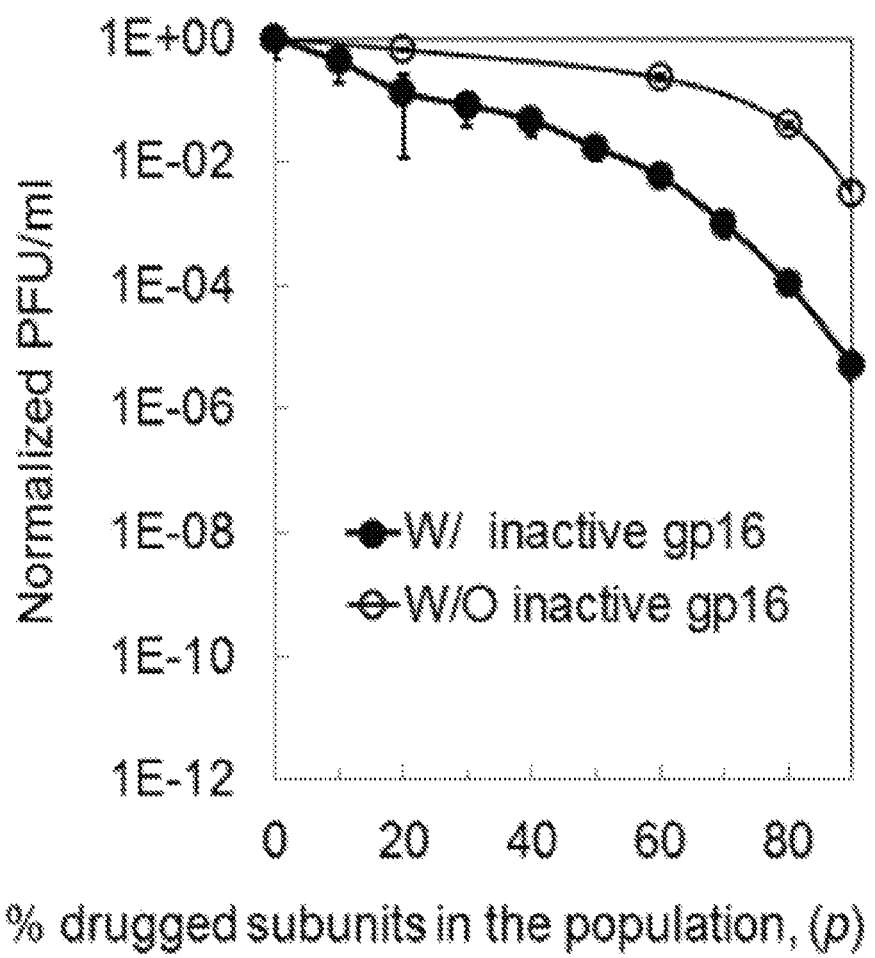
FIGS. 5A-5C show comparison of inhibition efficiency using targets with different Z values.

Determination of gp16 stoichiometry was carried out by in vitro phage assembly assay and based on the binomial distribution of wild-type and Walker B mutant gp16 [51]. Different ratios of drugged Walker B mutant gp16 were mixed with undrugged gp16 to test the inhibition efficiency of gp16 mutation on phi29 DNA packaging motor. Assuming K equals 1 and the total copy number of gp16 (Z) is between 1 and 12, twelve theoretical curves for the production of phi29 virion against the ratio of the Walker B mutant corresponding to the stoichiometry (Z) of 1 to 12 were generated according to equation 2. The empirical data nearly perfectly overlapped the theoretical curve of Z=6, K=1[51]. This data suggested that the ATPase gp16 components of phi29 DNA packaging motor have a stoichiometry of six, and only one copy of the drugged gp16 can block the phi29 motor function. Comparing the inhibition effect of adding mutant gp16 with wild-type gp16 at different concentrations, it showed that adding mutant gp16 had a much stronger inhibition effect than the wild-type gp16 concentration dilution control (FIG. 5A). Comparing the inhibition effect of mutation on hexameric gp16 to the effect of mutation on single subunit target DNA, the gp16 mutation displayed a much stronger inhibition effect on virus assembly than the same ratio of DNA mutation, indicating the hexameric ATPase protein complex of virus assembly system should also be an efficient target for generating new anti-virus drugs with high potency.

In Vitro Testing of the Hypothesis Using ATP with Stoichiometry of More than 10000

Figure 5B:
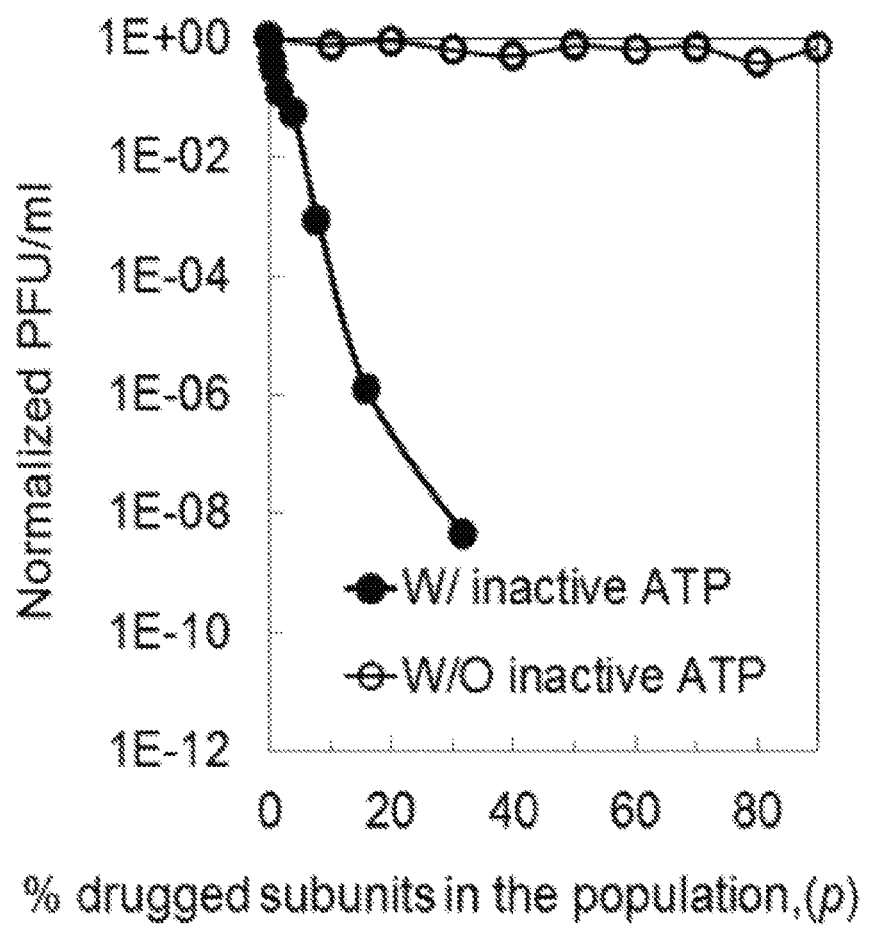

It has been reported that 6 ATP molecules are required to package one pitch of dsDNA with 10.5 bp [90], thus 1 ATP is used to package 1.7 bp. As the entire phi29 genomic DNA has 19,000 base pairs, it is expected that more than 10000 ATP molecules are required to package the entire phi29 genome. Since concerning ATP, the functional unit displayed in FIG. 5 is the viral production expressed as plaque-forming unit (PFU), so the production of one functional unit of PFU require 10000 ATP subunits to package one genomic DNA. Thus, the ATP in one phi29 nanomotor can be regarded as a stoichiometry of 10000. One non-hydrolysable ATP analogue γ-S-ATP was treated as the drugged subunit that mixed with ATP at different ratios to test the inhibition effect of γ-S-ATP on phi29 assembly efficiency. It was found that the inhibition curve of mutant ATP fits into the theoretical curve between Z=100. K=1 and Z=60. K=1 (FIG. 5B). The empirical ATP value derived from binomial distribution assay was different from real condition, since the binomial distribution equation was based on a condition that each subunits has the same binding affinity to the biocomplex in the targeted nanomotor, but due to the change of the γ-S-ATP structure, it has a ATPase gp16 binding affinity lower than the normal ATP. Furthermore, the affinity difference in each subunit has a multiplicative effect in the nanomotor's activity. Thus, there is a big discrepancy between the curves with predicted Z value and the empirical Z value.

Figure 5C:
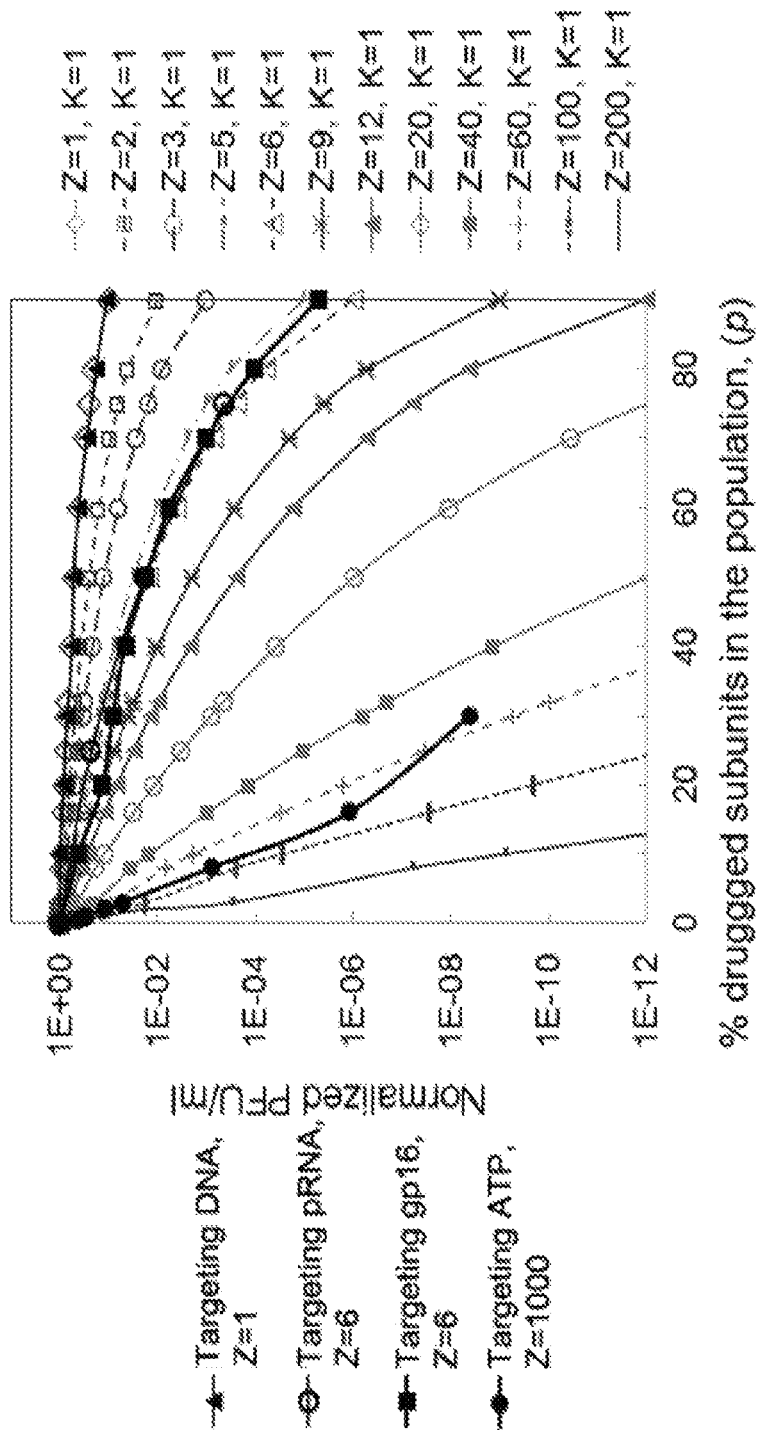

Comparing virus assembly inhibition effect using different components, the γ-S-ATP showed a severe inhibition effect (FIG. 5C). Adding 20% of gamma-s-ATP nearly completely inhibited the viral assembly. Comparing the inhibition effect targeting to ATP, pRNA, ATPase gp16, and DNA with stoichiometry of 10000, 6, 6, and 1, respectively, γ-S-ATP showed the strongest inhibition effect, while drugged mutant pRNA and mutant gp16 showed stronger inhibitory effect than mutant DNA (FIG. 5C). For example, adding 20% mutant DNA caused 20% inhibition effect in viral assembly, while 20% of drugged mutant pRNA exerted 74% of inhibition effect on viral assembly and 20% of γ-S-ATP almost completely inhibited the viral assembly, indicating the higher the stoichiometry, the stronger the inhibition efficacy.

Mathematical Reasoning for the Increase of Inhibition Efficacy

Using a biological complex with higher stoichiometry as drug target will substantially reduce the proportion of non-inhibited complex. For K=1, the proportion of non-inhibited complex is $q^Z$. Table 3 compares the proportion of non-inhibited complex from two populations with Z=6 and Z=1, respectively, with varied substrate targeting efficiency (p) when K=1. For example, when q=0.4, the proportion of non-inhibited complex is $q^Z=0.4^1=0.4$ for Z=1. K=1. Therefore, only 1-0.4=60% of complex is inhibited. In contrast, for Z=6, K=1, the proportion of non-inhibited complex is $q^Z=0.4^6=0.0041$. Therefore, 1-0.0041=99.59% of complex is inhibited. The ratio of the proportions of non-inhibited complex equals 0.0041/0.4=0.0102, indicating a 1/0.0102=98-fold decrease in the proportion of non-inhibited complex. One more example is to use the drug targeting efficiency p=0.9 to compare the inhibition efficiency between two groups with Z=6 and Z=1. For Z=6, K=1, the proportion of inhibited complex is $1-q^Z=1-0.1^6=0.999999$. The proportion of non-inhibited complex is $q^Z=0.1^6=$ 1E-6.

For Z=1, K=1, the proportion of inhibited complex is $1-q^Z=1-0.1=0.9$. The proportion of non-inhibited complex is $q^Z=0.1$. The ratio of inhibition efficiency equals to 1E-6/0.1=1E-5, indicating a 10000-fold increase in inhibition efficiency (Table 3).

The equation displays inhibitory effect with a power function of stoichiometry since when K=1, the percentage of uninhibited biocomplexes in the population equal to $q^z$. Since (P+q)=1, thus q≤1, thus the larger the Z, the smaller the value of $q^z$ That is to say, the higher the stoichiometry, the smaller number of the uninhibited background will display. With the same substrate targeting efficacy, p, the inhibition efficiency is determined by z, the power of the equation component. The inhibitory effect is a power function concerning the stoichiometry. Thus, the higher the stoichiometry, the more efficient the inhibition comparing the drugs with same binding affinity.

Figure 6:
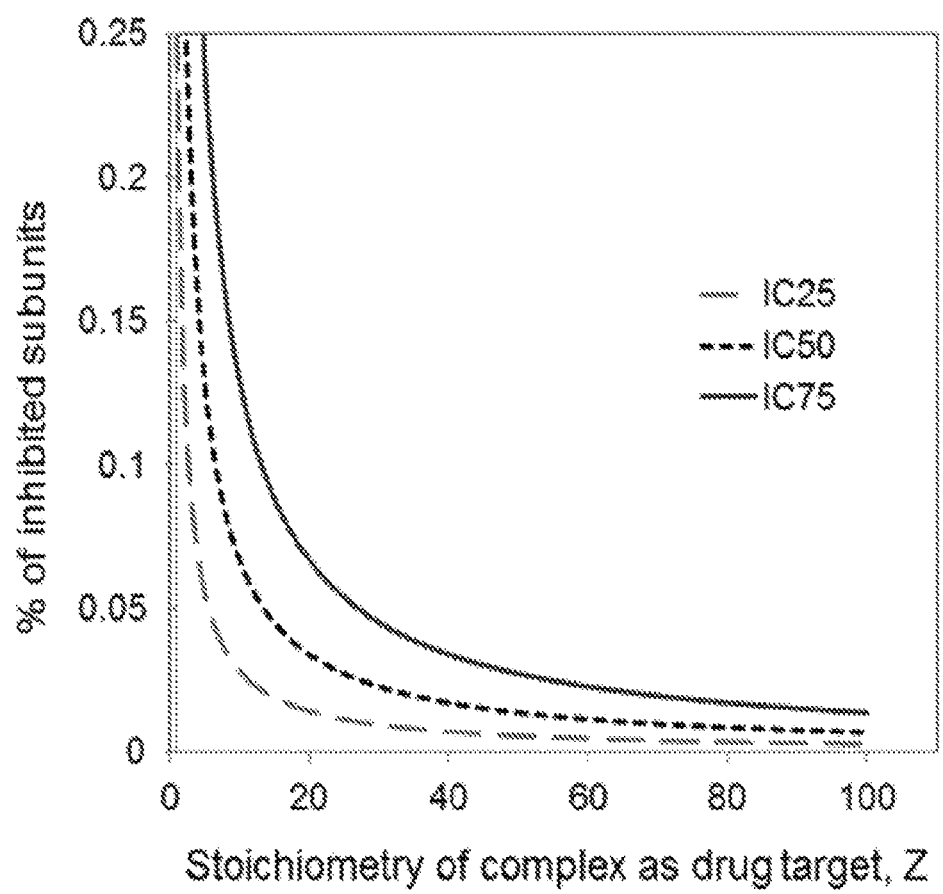
FIG. 6 shows a relationship between stoichiometry (Z) and drug targeting level (a combined result of drug binding efficacy and drug concentration) to reach the inhibition effect (IC).
Figure 7A:
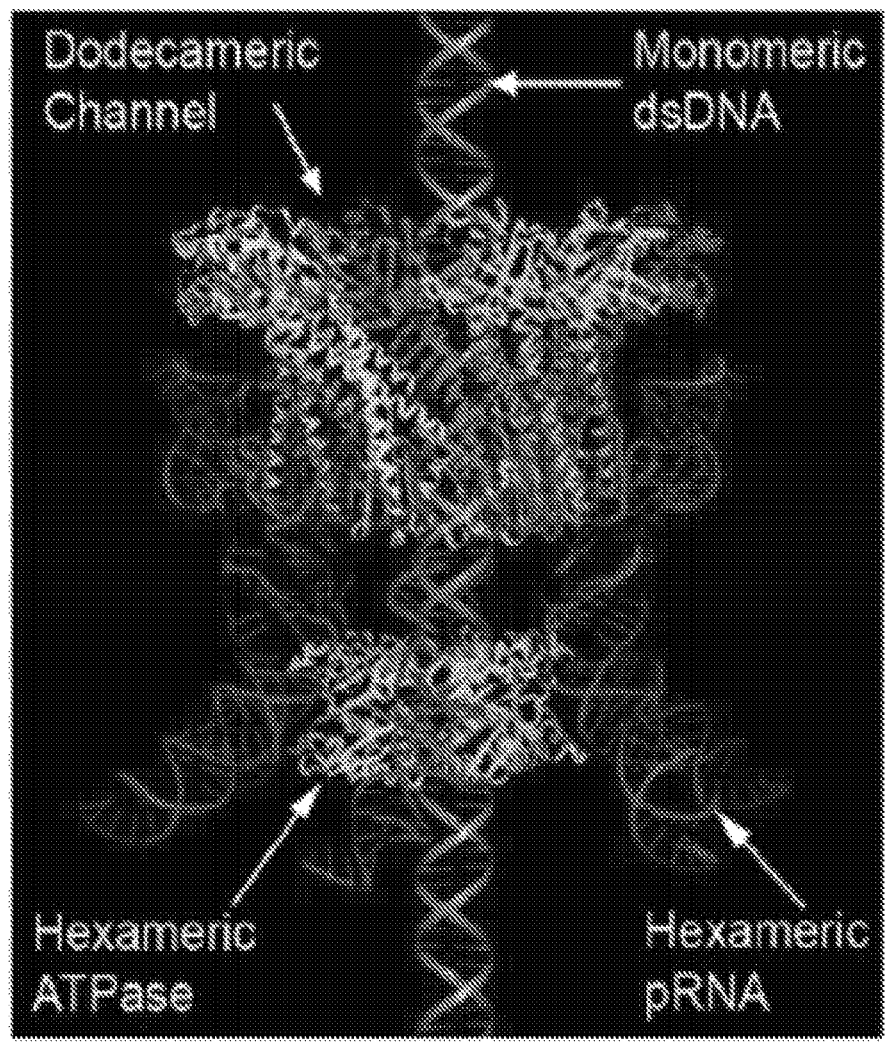
FIGS. 7A-7C show the morphology and stoichiometry of Phi29 DNA packaging motor.
Figure 7B:
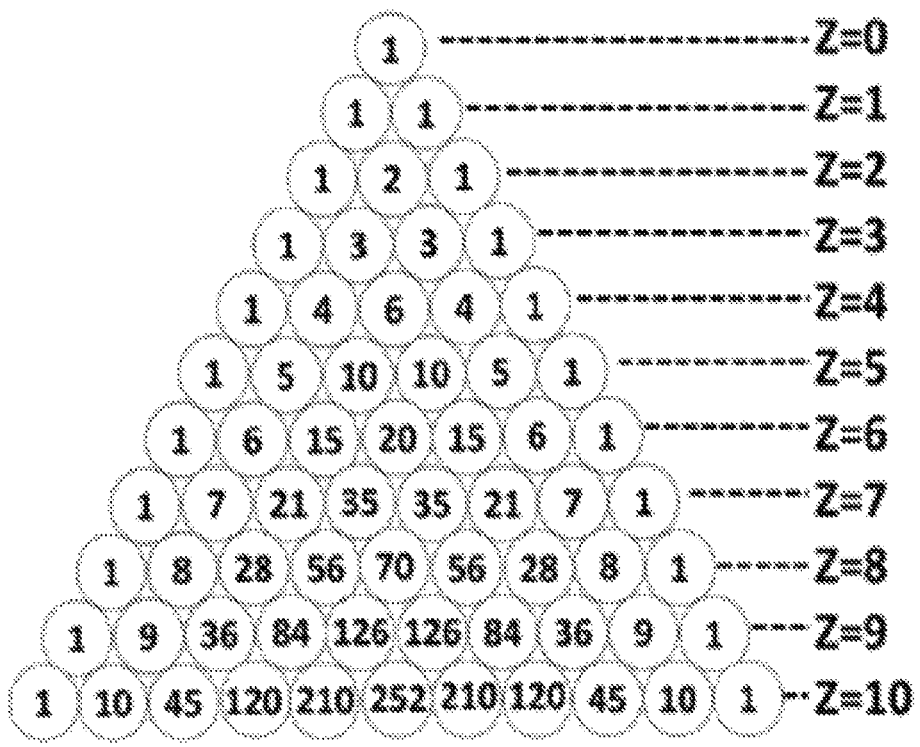
Figure 7C:
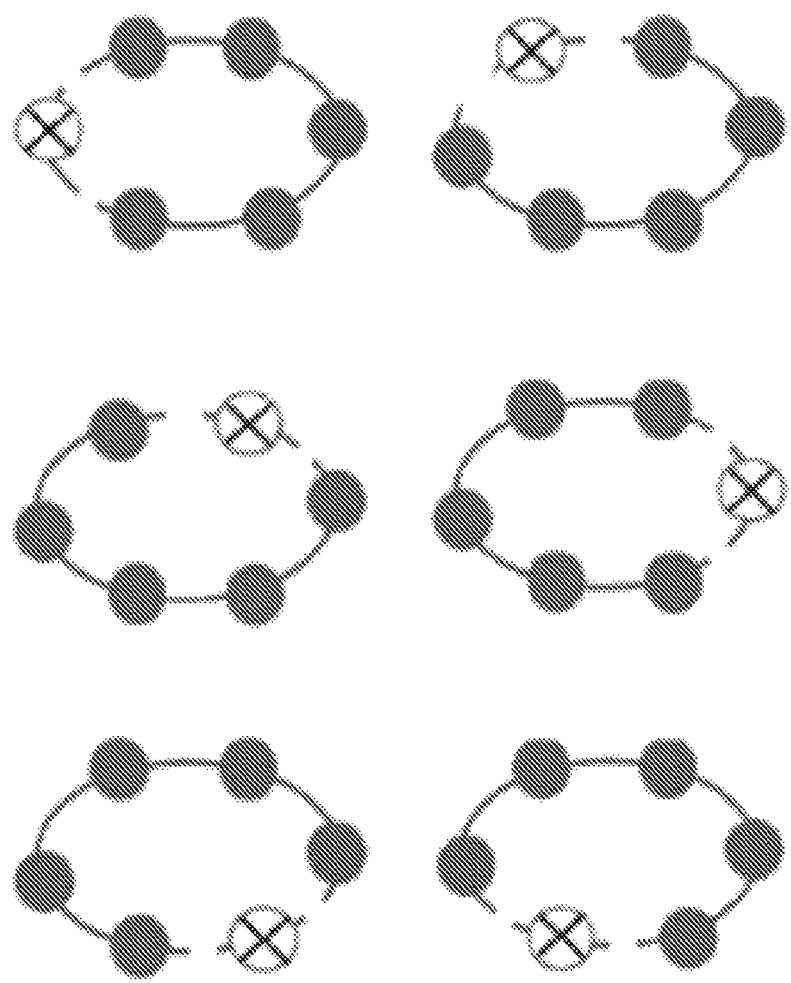

The half maximal inhibitory concentration ($IC_{50}$) is commonly used to evaluate drug effect, which quantitatively indicates how much of a particular drug is needed to inhibit a given biological process by half. If we denote $P_{IC50}$ as the percentage of drugged subunit needed to reach to 50% inhibition in the the in vitro assay in the defined system, thus $1-(1-p_{IC50})^Z=50\%$. Solving this equation, $p_{IC50}=1-0.5^{1/Z}$. FIG. 6 shows the relationship between stoichiometry (Z) and drug targeting level p to reach the inhibition effect (IC), where p is the combined result of drug binding efficacy and drug concentration (dosage). When biocomplexes with stoichiometry of Z are used as drug targets, the dosage of drug or the drug binding affinity presented by percentage of drugged subunits to reach $IC_{50}$, $IC_{25}$, or $IC_{75}$ decreases. This clearly shows that as Z increases, decreases (FIG. 6), and hence the drug is more potent.

Discussion

Aiming to find a method for developing drugs with ultra-high potency, we proposed that the inhibition efficiency of a given drug depends on stoichiometry of the biocomplex or bio-machine that was used as drug target. Here the definition of the stoichiometry is different from conventional definition of stoichiometry used to evaluate drug efficiency. Conventional thinking in drug development emphasizes stoichiometry which refers to the number of drug binding per target molecule, which is also known as $B_{max}$. In this study the definition of stoichiometry refers to the copy number of subunit within a biocomplex that serves as drug target. We used phi29 viral components with a series of variable but known stoichiometry as mock drug targets to test the hypothesis. Both in vitro and in vivo virion assembly assays were employed to compare the inhibition efficiency targeting to components with different numbers of subunit stoichiometry. Viral inhibition efficiency was analyzed with Yang Hui's (Pascal's) Triangle (or knowns as binomial distribution). It was found that inhibition efficiency on virus replication correlates to the component stoichiometry of nano-machine as drug target. It displayed power law inhibitory effect since when K=1, the percentage of uninhibited biocomplexes in the population equal to $q^z$. With the same q and same K value, the inhibition efficiency is determined by z, the number of subunits within the biocomplex or the bio-machine as drug target. Here z serves as the power in the equation, thus, the inhibitory effect is the power of the stoichiometry. Empirical data demonstrated that the target with thousand-subunits shows higher inhibition effect than the targets with six subunits, and in turn higher than the target with single subunit.

In evaluation of drug effect, two parameters were commonly used. One is the half maximal inhibitory concentration ($IC_{50}$), which quantitatively indicates how much of a particular drug is needed to inhibit a given biological process by half. It is universally used as a measure of drug potency in pharmacological research. Another important parameter is the median lethal dose ($LD_{50}$), which is also known as 50% of lethal concentration ($LC_{50}$). $LD_{50}$ is frequently used to indicate a substance's acute toxicity. Obviously, the usefulness of a drug will dependent on the ratio of $LD_{50}$ to $IC_{50}$. The larger this ratio, the safer the drug. By ways of increasing the inhibition efficiency through targeting to the components with high stoichiometry, the $IC_{50}$ of a drug will decrease. As a result, lower concentration of drug will be required for reaching a desired effect, resulting in a reduced toxicity of the drug.

Most of current anti-cancer, anti-virus or anti-bacteria drugs target single enzymes or single proteins. Our data showed that drugs selected to target components, biocomplexes, or nano-machines with high copy numbers could lead to a much higher efficacy, and it could potentially solve the problem of low drug effect and multi-drug resistance.

Conclusions

Targeting the functional biological units with higher stoichiometries will have a higher efficiency of inhibition. The inhibition effect is power, other than proportional, and the power, is the copy number of the drug-targeted element of the machine. The new theory developed herein suggests that potent drugs can be developed by targeting biocomplex with high stoichiometry, and a complete inhibition of virus, bacterium, or cancer is possible if a bio-machine with high stoichiometry is identified. Since bio-motors share certain common structure and operation mechanism in viruses, bacteria, and cells, this approach should have general application in drug development.

Living systems contain many elegant arrays, motors and nanomachines that are multi-subunit complex. As reported here, these biocomplex with high copy number of components can serve as potent drug targets. For example, most members of the AAA+ family are hexamer [19,87,88,106, 107,108]. However, these machines are common in living systems therefore the specificity and toxicity is an issue. For bacteria and virus, since our goal is to kill them nonexclusively, the specificity and toxicity is not an issue as long as the target biocomplex is not identical to that in human body. For cancers drugs, as long as a mutation is found in the multiple-subunit biocomplex, it will be an ideal target for potent drug.

Disclosed Method(s)

A method is disclosed herein for developing potent drugs. Drug inhibition potency depends on the stoichiometry of the targeted biocomplex.

Approach:

Phi29 viral components with variable stoichiometry were used as model to prove the hypothesis. Virion assembly efficiency was assayed and analyzed with Yang Hui's Triangle:

$$(p+q)^Z = \sum_{M=0}^{Z} \binom{Z}{M} p^{Z-M} q^M.$$

Results:

Inhibition efficiency displayed a power function of the stoichiometry of the target biocomplexes. The uninhibited biocomplex in population can equals to $q^Z$. Thus, the inhibitory effect is a power of the stoichiometry. Targets with thousand-subunit showed higher inhibition effect than with six subunits, and in turn higher than target with single subunit. A complete inhibition of virus, bacterium, or cancer was demonstrated when targets with high stoichiometry was used as target.

Conclusions

Drug inhibition potency depends on the stoichiometry of the targeted components of the biocomplex or nano-machine. The inhibition effect displayed a power function of the stoichiometry of the target biocomplex. Since bin-motors share certain common structure and operation mechanism in viruses, bacteria, and cells, this approach should have general application in drug development.

Section 2

Multidrug resistance and the appearance of incurable diseases inspire the quest for potent therapeutics.

A new methodology in designing potent drugs is developed by targeting multi-subunit homomeric biological motors, machines, or complexes with Z>1 and K=1, where Z is the stoichiometry of the target, and K is the number of drugged subunits required to block the function of the complex. The condition is similar to the series electrical circuit of Christmas decorations; failure of one light bulb results in power-off of the entire lighting system. In most multisubunit homomeric biological systems, a sequential coordination or cooperative action mechanism is utilized, thus K equals 1. Drug inhibition depends on the ratio of drugged to non-drugged complexes. When K=1, and Z>1, the inhibition effect follows a power law with respect to Z, leading to enhanced drug potency. The hypothesis that the potency of drug inhibition depends on the stoichiometry of the targeted biological complexes was recently quantified by Yang-Hui's Triangle (or binomial distribution), and proved using a highly sensitive in vitro phi29 viral DNA packaging system. Examples of targeting homomeric bio-complexes with high stoichiometry for potent drug discovery are discussed.

Biomotors with multiple subunits are widespread in viruses, bacteria, and cells, making this approach generally applicable in the development of inhibition drugs with high efficiency.

The continuous escalation of drug resistance has been threatening human health and life, i.e., many microorganisms including bacteria, viruses, and even cancer cells are developing resistance to current chemotherapies. Drug resistance in cancer has partially contributed to ~600,000 deaths in the USA in 2012[1]. To combat the on-rising drug resistance, different approaches for developing new drugs have been explored. One method is to develop drugs that target new mechanisms. Components highly important for cancer cell growth have been explored as drug targets for the treatment of multidrug resistant cancer[2, 3]. The first 1-DA-approved drug to treat multidrug-resistant tuberculosis, bedaquiline, follows a new mechanism of inhibiting the bacterial ATP synthase of M. tuberculosis and other mycobacterial species[4]. Another approach is to use nano-drug carriers to enhance the binding efficiency of drugs to cancer cells[5-8]. A third approach is to develop new combinational drugs acting on multiple targets to enhance its efficacy [9, 10], including cocktail therapy[11]. This involves identifying multiple targets that when treated simultaneously lead to a synergetic therapeutic effect and optimizing the design of multi-target ligands[12]. Still, there is unmet need for treating multi-drug resistant disease. Thus, new approaches for drug development are needed to combat drug resistance.

A new hypothesis that potent drugs can be developed by targeting proteins or RNA complexes with high subunit stoichiometry was reported recently[13]. The major challenge for testing this hypothesis is to evaluate the significance of the target stoichiometry and the binding affinity of the drug molecule with respect to its efficacy. In order to quantitatively correlate the drug inhibitory efficacy to the stoichiometry of the target biocomplexes, a well-studied multicomponent system is required, which allows an empirical comparison of functional inhibition efficiency of individual components with different numbers of subunits.

The DNA packaging motor of bacteriophage phi29 was an ideal model for testing this theory. The morphology and stoichiometry of the individual components in the phi29 DNA packaging motor have been well studied. The Phi29 biomotor (FIG. 1A) is composed of three essential, co-axially stacked rings[14-17]: a dodecameric connector ring located at the vertex of the viral procapsid; a hexameric packaging RNA (pRNA) ring bound to the N-terminus of the connector[16, 18], and a hexameric ring of ATPase gp16 attached to the helical region of pRNA[19-21]. The stoichiometry of pRNA was first determined using Yang Hui's Triangle (or binomial distribution) in 1997[22], and similar mathematical methods were applied to determine the stoichiometries of the protein subunits [14]. Furthermore, dsDNA packaging utilizes a revolution mechanism without rotation to translocate its genomic DNA powered through the hydrolysis of ATP[20, 21, 23-28]. The copy number of ATP molecules required to package one full Phi29 genomic dsDNA has been predicted to be 10,000[20, 21, 23-27, 29]. Phi29 DNA packaging, thus, offers an ideal platform to test the concept described above: the dependence of the inhibitory drug efficiency on the stoichiometry of its targeted biocomplex.

Although the theory of targeting multisubunit complexes for developing potent drugs was reported and validated recently[13], real cases of targeting multisubunit complex for new drug development have been practiced[30-32]. Since multicomponent biomotors are widely spread in nature[26, 27, 33, 34], the approach of targeting multisubunit complexes for potent drug development discussed here is generally applicable, especially in developing new generations of drugs for combating the rising acquired drug resistance in viruses, bacteria, and cancers [35-37].

Rationale for Selection of Multi-Subunit Biocomplexes as Efficient Drug Targets

Inhibitory drugs are typically designed to bind selectively to a target site, thereby blocking the site from interaction with other biomolecules leads to the loss of essential activity of the biological target. This target can be a single element, composed of only one subunit, or a complex consisted of multiple subunits, such as the biomotors of the hexameric ASCE (Additional Strand Catalytic E) superfamily[20, 38]. Conventional drugs are designed to inhibit pathogenesis through targeting of a single subunit molecule, such as an enzyme or a structural protein of a virus. As discussed below, the key in designing potent drugs lies in targeting multisubunit biological motors, machines, or complexes as drug targets that follow a sequential coordination or cooperative mechanism. The stoichiometry of the complex, Z, is larger than 1 and the number of drugged subunits that are required to block the activity of the target complex, K, equals 1 (Z>1 and K=1). Similar to in-series connected decorative Christmas lights, where one broken light bulb will turn off the entire chain, one drugged subunit will inhibit the entire complex and therefore biological activity. Sequential action or cooperativity in multisubunit complexes has been widely reported in biological systems[39-43]; inhibiting any subunit leads to inhibition of the entire complex, or in other words K equals 1.

For a conventional drug that inhibits its single subunit target (Z=1) with efficiency p, the fraction of undrugged target molecules q will be 1−p; and those undrugged target molecules will remain active to maintain their biological function. In this situation, the inhibition efficiency is proportional to the substrate targeting efficiency p[39-41]. When targeting a dimeric complex (Z=2), for example, inactivating any subunit results in inhibition of the whole complex. For a drug targeting a dimeric complex with substrate targeting efficiency p=0.9 (90%), only 10% of the first subunit and 10% of the second subunit remain active after drug targeting. Thus, the fraction of undrugged complexes will be effectively reduced to 0.01, leaving 1% of complexes active. Since drug inhibition depends on the ratio of drugged to undrugged complexes, the efficiency of the inhibition is proportional to the product of the inhibition of the individual subunits, in other words, it follows a power law with respect to Z.

Consequently, a complex composed of Z subunits with the smallest number of blocked subunits (K) to inhibit activity of the complex is 1, when p percent of subunits are interacting with the drugs, the fraction of uninhibited biocomplexes will be $q^Z$ and the proportion of inhibition equals $1-q^Z$.

2.1 Drug Inhibition Efficiency Predicted by Binomial Distribution Model

The scenario outlined above follows a binomial distribution which can hence be used to outline the relation between drug inhibition efficiency and target stoichiometry in general. When the target element is a monomer, the inhibition efficiency can be calculated using Equation 1, where p and q are the fractions of drugged (substrate targeting efficiency) and undrugged (normal active elements) subunits, respectively (p+q=1).

$$X=(p+q)^1 \tag{1}$$

However, when the target element contains multiple subunits, a higher order binomial distribution (Equation 2) is required to calculate the ratio of active complexes, where Z represents the total number of subunits (the stoichiometry) and M the number of drugged subunits in one biocomplex.

$$X = (p+q)^Z = \sum_{M=0}^{Z} \binom{Z}{M} p^{Z-M} q^M = \sum_{M=0}^{Z} \left(\frac{Z!}{M!(Z-M)!}\right) p^{Z-M} q^M \tag{2}$$

Note that the binomial distribution as set forth in equation 2 may also be expressed as follows:

$$\sum_{M=0}^{Z} \binom{Z}{M} p^M q^{Z-M} = \sum_{M=0}^{Z} \left(\frac{Z!}{M!(Z-M)!}\right) p^M q^{Z-M}$$

Computational results based on the binomial equation are set forth herein. The context of the results governs which form of the equation is used.

The probability of drugged subunits (M) and undrugged subunits (N; M+N=Z) in any given biocomplex can be determined by the expansion of Equation 2. When Z=3, The expanded form of Equation 2, $(p+q)^3=p^3+3p^2q+2pq^2+q^3=1$, displays the probabilities of all possible combinations of drugged and undrugged subunits of a homotemary complex composed of three ($p^3$), two ($p^2q$), one ($pq^2$), or no ($q^3$) drugged subunits; the sum equals 1. Assuming that 70% (p=0.7) of subunits are inactivated by bound drugs leaving 30% (q=0.3) unaffected, then the percentage of complexes possessing at least two copies of normal subunits would be the sum of those possessing one copy of drugged and two copies of undrugged wild-type subunits, $3pq^2$, and those possessing three copies of native subunits is $q^3$, i.e., 3pq2+ q3=3(0.7)(0.3)2+(0.3)3=0.216. In another example, if a complex contains 6 subunits, and biological activity requires 5 out of the 6 subunits to remain uninhibited, the fraction of active complexes in the total population equals the sum of probabilities of obtaining: 1) 5 and 2) 6 undrugged subunits.

Using the binomial distribution, the probabilities that a population contains any combination of undrugged versus drugged subunits can be predicted. The effect of the targeting efficiency p on the probability of obtaining a given complex with M drugged and N undrugged subunits is displayed in Table 1. The probabilities are calculated using equation 2, $$\frac{Z!}{M!N!} p^M q^N,$$

with the coefficients $$\frac{Z!}{M!N!}$$

obtained from Yang Hui's Triangle, which is also called Pascal's Triangle, or binomial distribution (FIG. 1B)[44]. The use of Yang Hui's Triangle and binomial distribution to determine the stoichiometry of biological motor was published in Guo Lab in 1997[22, 45] for RNA component and restated in 2014 for protein component[14] in phi29 DNA packaging motor.

2.2 Cooperativity in Multisubunit Biocomplexes Leads to High Inhibition Efficiency The cooperativity of multisubunit biocomplexes is the key to high drug inhibition efficiency. Cooperativity means that multiple subunits work sequentially or processively to accomplish one essential biological reaction [23, 40-42, 46-50]. Blocking any subunit of the complex inhibits the activity of the whole complex. Many reactions involving multiple subunits work cooperatively, e.g. assembly pathways in viral assembly systems [39, 51]. An analogy to such a biological reaction mechanism is given by the difference between parallel and series circuits. When a chain of light bulbs is arranged in a parallel circuit, burning out one light bulb will not affect others, while in a series circuit, breaking any one light bulb turns off the entire lighting system. The K value, the smallest number of subunits that needs to be inhibited in order to inhibit function of the light chain is therefore, K=1. Thus, the K value is a key factor in estimating the probability of obtaining inactive nanomachines or biocomplexes by combination and permutation of all subunits.

K=1 is critical for obtaining ultrahigh inhibition. The foundation of the approach in this report is the difference in inhibition probability for biocomplexes with the same ratio of drugged target subunits but different K values. Biological systems display complicated reactions that involve several steps and multiple components interacting in series or parallel Based on the binomial math model and cooperative nature of biological reactions, we suggest that targeting of multi-subunit biocomplexes can serve as a tool to develop highly potent drugs. In a conventional six-component system, when one drug is designed to target only the component #3 to stop the entire system, such a condition resembles the model in equation 2 with Z=1 and K=1. Thus, the inhibition efficiency is linear to the substrate targeting efficiency (p) of the drug. However, in a homohexameric component system, the entire complex is blocked when a drug targets any subunit of the hexamer, which resembles Z=6 and K=1. Thus, the probability of active target complexes equals $q^6$ (q=1−p). In other words, the drug inhibition efficiency is equal to 1-$q^6$, which scales with the $6^{th}$ power of q compared to linearly with q as for conventional mono-subunit approaches (see Table 1).

Targeting a biological complex that exhibits a higher stoichiometry substantially reduces the fraction of non-inhibited complexes. K=1 implies that drug binding to one subunit inactivates the subunit, in which one drugged subunit is sufficient to inhibit the function of the entire complex. As an example, a probability calculation for Z=6 and K=1 is given below. As all 6 (Z=6) copies of the subunits are required for function, while one drugged subunit (K=1) is sufficient to block the activity, all elements possessing 1 through 5 copies of drugged subunits are non-functional (FIG. 1C). Only those complexes possessing 6 copies of undrugged subunits are functional. The probability that a complex contains 6 copies of unaffected subunits is $q^6$ and therefore the inhibition efficiency is 1−$q^6$ [12, 23, 39, 46, 51, 52].

Consequently, for a drug with binding efficiency p, a larger stoichiometry of the target complex substantially increases the inhibition efficiency. To illustrate, we compare the fraction of non-inhibited complexes for Z=6 and Z=1, while keeping q=0.4 and K=1 fixed for both target systems. The fraction of non-inhibited complexes for Z=1 amounts to $q^Z=0.4^1=0.4$, resulting in 1-0.4=60% of inhibited complexes. In contrast, for Z=6, the fraction of non-inhibited complexes is $q^Z=0.4^6=0.0041$ and therefore 1-0.0041=99.59% of complexes are inhibited. The ratio of the remaining non-inhibited complexes (0.4/0.0041=98) shows a 98-fold decrease in non-inhibited complexes for Z=6 compared to Z=1. At a targeting efficiency of p=0.9, the inhibition efficiency for Z=6 is 1−$q^Z$=1-$0.1^6$=0.999999 resulting in a 10,000-fold increased inhibition efficiency compared to Z=1 ($0.1/0.1^6=10^5$, see Table 1). The binomial distribution indicates that the inhibitory effect follows a power law with respect to the stoichiometry of the target. Thus, for K=1, the fraction of uninhibited biocomplexes equals $q^Z$; the larger Z, the smaller $q^Z$, (as 0<q<1). That is to say when developing drugs with the same binding affinity to their targets, the higher the stoichiometry of its multimeric target, the fewer uninhibited targets will remain and the more efficient the drug will be.

2.3 $IC_{50}$ Decreases as the Stoichiometry of Target Complexes Increases

The half maximal inhibitory concentration ($IC_{50}$) is one parameter used to evaluate drug efficacy. It quantitatively indicates how much of a particular drug is required to reduce the activity of a given biological process by half. It is universally used as a measurement of drug potency in pharmacological research. The median lethal dose $LD_{50}$, also known as 50% of lethal concentration, is an important parameter to evaluate the safety profile, i.e., acute toxicity of a drug. Most importantly, a larger ratio of $LD_{50}$ to $IC_{50}$, results in a safer drug. By increasing the inhibition efficiency through targeting components with high stoichiometry, the effective drug dosage is greatly decreased, thus decreasing the $IC_{50}$. As a result, the ratio of $LD_{50}$ to $IC_{50}$ increases, resulting in an enlarged therapeutic window of the drug.

Figure 8:
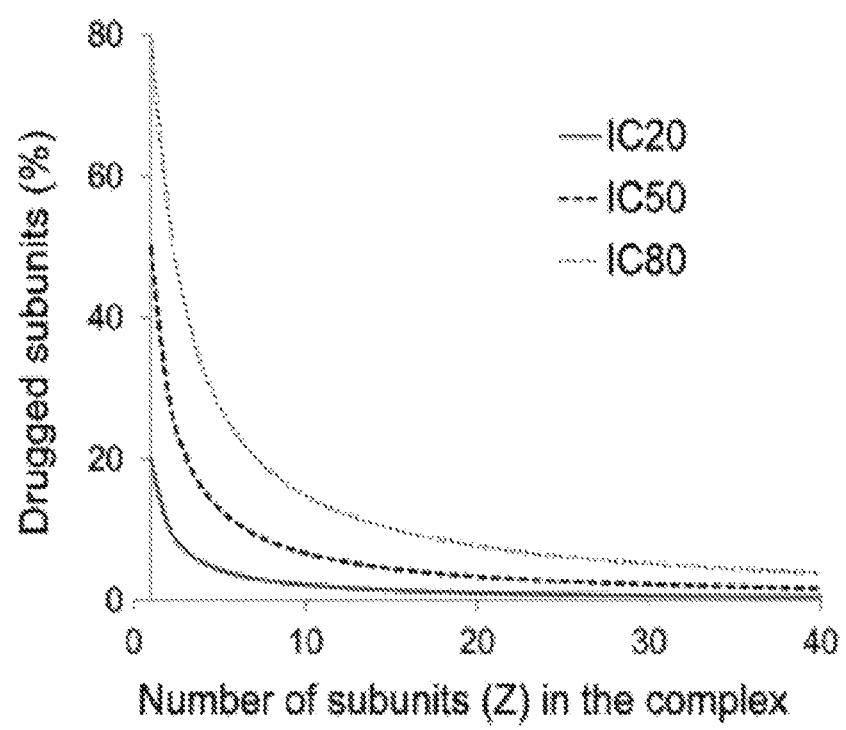
FIG. 8 shows the relationship between the stoichiometry of homomeric target complex (Z) and target complex inhibition effect (IC).

If we denote $P_{IC50}$ as the percentage of drugged subunits needed to reach 50% inhibition, then $1-(1-p_{IC50})^Z=50\%$ Solving this equation $p_{IC50}=1-0.5^{1/Z}$. FIG. 8, shows the relationship between stoichiometry (Z) and drug targeting level p to reach the inhibition effect (IC), where p is a combined result of drug binding efficacy and drug concentration (dosage). When the stoichiometry Z of the multimeric drug target increases, the dosage of drug to reach $IC_{50}$, $IC_{20}$, or $IC_{80}$ decreases, presented by the percentage of drugged subunits. This clearly shows that as Z increases, $p_{IC50}$ decreases, and hence the drug is more potent.

Focusing on the stoichiometry of the target complex for drug development differs from conventional approaches. Conventional drug molecules are sought to have a high binding affinity to the target, which means we expect more drug molecules to bind to one target molecule. Here stoichiometry refers to the copy number of subunits within a biocomplex or nanomachine that serves as the drug target. This idea agrees with a newer model for predicting clinical drug efficacy, the receptor occupancy. Receptor occupancy acts as a predictor for human pharmacodynamics and antihistamine potency and takes into account both the affinity of the drug for its receptor and its free plasma concentration [53].

Inhibition Efficiency as a Power Function of Target Stoichiometry Proved by Phi29 Viral Assembly System The hypothesis that drug inhibition efficiency follows a power function with respect to the target stoichiometry has been proved using the Phi29 viral assembly system [54]. This well-defined in vitro assembly system is composed of four components, each of which is comprised of different subunits that can act as the nano-machine target. Inhibition of viral assembly is achieved using mutant components that represent drugged target components. The inhibition efficiencies were analyzed with Yang Hui's triangle for targeting each of the Phi29 DNA packaging motor components. Binomial distribution analysis of these viral assembly competition assays confirmed the concept that drug targeting biological complexes with higher stoichiometry results in a higher efficiency than drugs acting on a single subunit target.

The highly sensitive in vitro Phi29 assembly system was used to determine the inhibition efficiency of drugs targeting multi-subunit complexes [22, 39, 45, 55], thus validating a new method for developing potent drugs. The bacteriophage Phi29 DNA packaging motor contains one copy of genomic dsDNA, 6 copies of packaging RNA, 6 copies of ATPase protein gp16, and consumes more than 10,000 copies of ATP during genome packaging. The hexameric stoichiometry of Phi29 pRNA has been extensively shown using single-molecule techniques[54], AFM imaging[56, 57], pRNA crystal structure determination[58], and statistical evaluations[22]. The hexameric stoichiometry of Phi29 gp16 has been proved by native gel binding, capillary electrophoresis assays, Hill constant determination, and by titration of mutant subunits using binomial distribution[20, 23]. The copy number of ATP molecules was calculated based on the fact that 6 ATP molecules are required to package one pitch of dsDNA containing 10.5 base pairs [59], thus one ATP is used to package 1.7 base pairs of dsDNA. The entire Phi29 genome is composed of 19,400 base pairs, thus, it is expected that more than 10,000 ATP molecules are required to package an entire Phi29 genome. The availability of a motor system with multiple well-defined and characterized components makes an ideal disease model for the analysis of drug inhibition efficiency versus the subunit stoichiometry of individual subcomponents within the same assay.

Inhibition efficiencies were determined for ATP, pRNA, ATPase gp16, and DNA as drug targets with stoichiometries of 10,000, 6, 6, and 1, respectively. Among these components, targeting of ATP showed the strongest inhibition, while drugged mutant pRNA and mutant gp16 still showed stronger inhibitory effects than mutant DNA (FIG. 3). For example, adding 20% mutant DNA caused 20% inhibition of viral assembly, while 20% of drugged mutant pRNA exerted 74% of inhibition on viral assembly and 20% of γ-S-ATP almost completely inhibited the viral assembly, indicating that higher stoichiometry results in stronger inhibition efficacy.

The target with ten-thousand-subunits showed higher inhibition than those with six subunits, which in turn showed higher inhibition than the single subunit target. In conclusion, these results show that inhibition efficiency displays a power function with respect to the stoichiometry of the target biocomplexes. Drug inhibition potency depends on the stoichiometry of the targeted components of the biocomplex or nano-machine. Since bio-motors share certain common structural and operational mechanisms across viruses, bacteria, and other cells, this approach has general application in drug development.

Wide-Spread Distribution of Biomotors with Multiple Subunits or High Order Stoichiometry Biological systems contain a wide variety of nanomachines with highly ordered stoichiometry that are essential for DNA replication, DNA repair[60], homologous recombination, cell mitosis, bacterial binary fission, Holliday junction resolution[61], viral genome packaging[62], RNA transcription, nuclear pore transport, as well as motion, trafficking, and exportation of cellular components. Here we use biological motors as an example to elucidate the rationale of Z>1 and K=1. These biological motors can generally be classified into three categories according to their DNA transportation mechanism: linear motors, rotation motors and the newly discovered revolution motors[23, 27, 34]. High order stoichiometries are wildly observed among biomotors, especially in rotation and revolution motors. Thus, biomotors are feasible targets for the development of potent inhibitory drugs that exploit the power law behavior of the subunit stoichiometry.

4.1 Rotation Nanomachines

FoF1 ATP synthase and helicases are representatives of rotary motors [63, 64]. FoF1 ATP synthase is a ubiquitous membrane enzyme that plays a key role in biological energy metabolism [65, 66]. It consists of two linked rotary motors, F1 and Fe, which are distinct in structure and function. F1 ATPase, forming the catalytic core, shows strong ATP hydrolysis activity. It is composed of 5 subunits $(\alpha_3\beta_3\gamma_1\delta_1\varepsilon_1)$, with three α and three β subunits forming a hexameric ring with part of a long coiled coil γ subunit. Fo is the proton pore that is embedded in the membrane, it consists of at least 3 subunits $(a_1b_1c_{8-15})$ whereby subunit c differs among species.

Helicase DnaB is a hexameric nanomachine (FIG. 4A) that unwinds dsDNA in front of the replication fork during DNA replication[67, 68]. Recently, a hand-over-hand translocation mechanism was proposed for DnaB based on the crystal structure of the DnaB hexamer complexed with ssDNA and GDP-AIF4 [69]. In this mechanism, the 5'-3' translocation of the subunits at a stepsize of two nucleotides is coupled with the sequential hydrolysis of NTP [70]. The sequential hand-by-hand migration of the individual subunits results in DNA translocation.

RecA, a family of ATP-dependent recombinases, plays an important role in dsDNA repair and genetic recombination in Archaea, Bacteria, and Eukaryota. It can interact with ssDNA forming right-handed helical filaments as a complex with approximately six monomers of RecA per turn (FIG. 4B)[71, 72]. Electron microscopy studies have demonstrated that ATP binding induces a re-orientation between the RecA ATPase domains, resulting in the relative rotation of the protein on DNA substrate during DNA translocation powered by ATP hydrolysis.

4.2 Revolution Nanomachines

All the dsDNA viruses known to date utilize similar mechanisms to transport their genome into preformed protein shells during replication. For example, Bacteriophage phi29, HK97, SPP1, P22, and T7 all share a common revolution mechanism for dsDNA packaging that employ a hexameric ATPase and predominantly dodecameric connector channels for packaging dsDNA. The phi29 DNA packaging motor is composed of three coaxial rings: a dodecameric channel ring and an ASCE hexameric ATPase linked by a hexameric ring of pRNA (FIG. 4C)[20, 54, 58]. During genome packaging, more than 10,000 ATP molecules are consumed by the hexameric ATPase as energy source to drive the translocation of one copy of the dsDNA genome [59].

The ASCE superfamily, including FtsK-HerA superfamilies and the AAA+ (ATPases associated with diverse cellular Activities), is a clade of nanomachines that display a hexameric arrangement[73-76] of subunits. Their biological function is to convert chemical energy from ATP into mechanical motion[20, 29, 77, 78], typically associated with conformational changes of the ATPase enzyme [20, 79, 80].

FtsK belongs to the ASCE superfamily. It is a multi-domain protein composed of a C-terminal ATPase domain FtsK(C) containing α, β and γ sub-domains, an N-terminal membrane-spanning domain FtsK(N) and a 600-amino acid linker[81-83]. It is responsible for conjugation between bacterial cells and dsDNA bidirectional translocation[84, 85]. It has been proposed that FtsK subunits acts in a sequential manner employing a revolution mechanism to translocate dsDNA[86, 87]. The crystal structure and electron microscopy of FtsK(C) demonstrates formation of a ring-like hexamer with DNA passing through the hexameric ring (FIG. 4D)[87, 88].

Targeting Biocomplexes for Developing Potent Drugs

As illustrated above, drug efficiency follows a power function of the stoichiometry of the subunits of the multimeric target biocomplex. Targeting biocomplexes with higher stoichiometry therefore can lead to the development of more potent drugs. Experimentally, approaches targeting receptor dimers, hetero- and homo-oligomers for drug screening open exciting possibilities for drug discovery and development[89].

Targeting Homomeric Channel Proteins for Drug Development

In the history of drug development, one important property of most channel protein receptors has been overlooked, their stoichiometry. As a matter of fact, many channel proteins are expressed as dimers or oligomers on cell membrane, including most G-Protein-Coupled Receptors (GPCR) proteins [89]. Targeting of GPCR hetero- and homo-oligomers is generally starting to be considered for drug development. Therefore, new models for multisubunit protein binding are being developed[89]. Cooperative binding affinity between ligand and multisubunit targets has been reported and cooperativity factors were calculated by fitting to the Hill equation[23, 89].

The ATP-sensitive homotrimeric P2X7 receptor (P2X7R) acts as a ligand-gated ion channel. It forms a chalice-like channel with three ATP binding sites localized at the interface of the three subunits. Occupancy of at least two of the three sites is necessary for activation of the receptors which results in opening of the channel pore allowing passage of small cations ($Na^+$, $Ca^{2+}$, and $K^+$). P2X7R has received particular attention as a potential drug target for its widespread involvement in inflammatory diseases and pivotal roles in central nervous system (CNS) pathology [30]. These concepts will broaden the therapeutic potential of drugs that target multi-subunit channel proteins, including receptor heteromer-selective drugs with a lower incidence of side effects. They will also help to identify new pharmacological profiles using cell models that express heteromeric receptors.

Targeting Homomeric Enzyme for Antibiotics Development

Targeting of key enzymes in essential biosynthesis pathways is an important approach for antibiotics development. Many key proteins in the fatty acid synthesis pathway and nucleotide synthesis pathway are found to be multivalent. The highly ordered oligomeric enzymes in biosynthesis pathways could be promising targets for developing more potent antibacterial drugs. Some examples of developing potent drags by targeting multisubunit biocomplexes are discussed below.

Fatty acid synthesis is an essential lipogenesis process in both Gram-positive and Gram-negative bacteria. A key enzyme in the fatty acid biosynthesis pathway is fatty acid biosynthesis 1 (FabI), which is a homotetramer complex acting as the major enoyl-ACP reductase present in *Burkholderia pseudomallei* (Bpm). A recent X-ray structure study revealed the binding mode of the inhibitor PT155 with the homo-tetrameric BpmFabI [31] (FIG. 5A). The substrate BpmFabI is a homo-tetramer, one PT155 molecule bound to each monomeric subunit has shown significant promise for antibacterial drug development[31]. Another example of targeting multisubunit biocomplex as drug target is found in the guanine nucleotide biosynthesis pathway to control parasitic infection. Inosine 5'-monophosphate dehydrogenase (IMPDH) is a homo-tetramer enzyme[32](FIG. 5B), which plays an important role by catalyzing the oxidation of IMP to XMP in guanosine monophosphate (GMP) biosynthesis[32]. Structural characterization of IMPDH with chemical inhibitor drugs indicates that binding to the repeating units shows a more potent inhibition effect[90].

These examples of successfully targeted homotetramer enzymes for potent drug development further proved the importance of the stoichiometry of target homo-meric complexes. When applying this method to search enzymes as drug targets, it is critical to test whether the stoichiometry of the complexes (Z) is >1, and the number of subunits needed to inhibit to block biological function (K) equals 1.

Targeting Homomeric Drug Transporters for Drug Development

The mechanism of drug transporter, very similar to that of the revolution motor, involves entropy induced transitions by ATP. High stoichiometry of the target complex is a key consideration in drug efficiency. Targeting multidrug efflux transporters with high stoichiometry has a better chance to develop drugs for treating multi-drug resistant disease. The structure of bacterial multidrug efflux transporter AcrB is composed of three alpha-helix subunits, that connect to form a funnel around a central cavity (FIG. 5C)[91]. The multidrug exporter MexB from *Pseudomonas aeruginosa* also forms a homotrimer (FIG. 5D)[92]. Pyridopyrimidine derivatives have been reported to be promising drugs to treat multidrug resistant pathogens by specific inhibition of the homotrimeric AcrB and MexB transporters[117]. The structural architecture of ABC transporters consists minimally of two TMDs and two NBDs. These four individual polypeptide chains combine to form a full transporter such as in the E. coli BtuCD[93]. Although the stoichiometry of the heterodimer is not very high, the stoichiometry of ATP per transporter is high. It is involved in the uptake of vitamin B12. The TMDs of ModBC-A and MalFGK2-E have six helices per subunit. These unique structural features can be used in target considerations.

Conclusion and Future Perspective

Targeting functional biological units with higher stoichiometries allows for higher inhibition efficiencies. The inhibition efficacy follows a power law with respect to the subunit copy number when targeting multimeric biocomplex, compared to a linear effect of the drug-target binding affinity when targeting a single-subunit substrate. This new concept outlined herein suggests that potent drugs can be developed by targeting biocomplexes with high stoichiometries with the potential of complete inhibition of the targets activity. Possibly, this method can further be applied to guide development of dominant negative proteins for potent gene therapy, which can be incorporated into a multimeric protein nanomachine and results in a change of its activity [94]. Since bio-motors share certain common structural and operational mechanisms across viruses, bacteria, and cells, this approach has general applicability in drug development.

Living systems contain many elegant arrays, motors and nanomachines that are composed of multiple identical subunits. As reported here, these homomeric biocomplexes can serve as potent drug targets. For example, most members of the ASCE family are hexamers[20, 95-99]. As these machines are common among living systems, specificity and toxicity need to be considered. In the development of anti-bacterial and anti-viral drugs, specificity and toxicity is not problematic since the target biocomplexes differ from those found in human cells and thus all targets are intended to be killed nonexclusively. In the development of anti-cancer drugs, mutations in multiple-subunit biocomplexes of cancer cell will present ideal targets for potent drug development.

Expert Opinion

Drug discovery is a multidisciplinary science including the fields of medicine, biotechnology and pharmacology. Aiming to find a method for developing drugs with ultra-high potency, much effort has been placed in the screening of new drug compounds, uncovering of new drug targets, and illumination of functional pathways, but little attention has been paid to the exploration of new methods for the design and development of more efficient drugs. Here we propose that the inhibition efficiency of a given drug depends on the stoichiometry of the biocomplex or bio-machine that serves as drug target. Here the notion of "stoichiometry" differs from the conventional concept in drug development. Conventionally, stoichiometry refers to the number of drug molecules bound to each substrate or cell membrane. In the current study stoichiometry refers to the number of identical subunits that the target biocomplex is composed of. Phi29 viral components with a series of variable but known stoichiometries were evaluated as mock drug targets to test the hypothesis. Both in vitro and in vivo virion assembly assays were employed to compare inhibition efficiencies for targets with differing subunit stoichiometries. Viral inhibition efficiency was analyzed with Yang Hui's (Pascal's) Triangle (also known as binomial distribution) (FIG. 1), as shown in equation 2.

It was observed that inhibition efficiency of virus replication correlates with the stoichiometry of the drug target. The inhibition efficacy follows a power law behavior where the percentage of uninhibited biocomplexes equals $q^Z$ (see equation 2). For a system with fixed q and K values, the inhibition efficiency thus depends on Z, the number of subunits within the target biocomplex or bio-machine. This hypothesis is supported by empirical data that a target with ten-thousand-subunits shows higher inhibition effect than a target with six subunits, which in turn shows higher inhibition than a single-subunit target (FIG. 3). The unconventional hypothesis described in this article for the development of potent drugs with power function behavior with respect to the target stoichiometry can be foreign or even outlandish to the main force of the pharmaceutical field. The approach of developing highly potent drugs through targeting of protein, RNA or other macromolecule complexes with high stoichiometry has never been reported due to challenges to prove the concept.

Traditionally, it is almost impossible to prove this concept by comparing efficacies of two drugs where one of them targets a biocomplex with multiple subunits. When reporting the efficiency of this new approach, it is very difficult to distinguish essentiality of the two targets in biological function, it is also very challenging to compare the binding affinity of two different drugs to two different targets. For instance, if two drugs target two stoichiometrically different complexes, it becomes extremely difficult to prove whether the difference in drug efficiency is due to differences in their target binding affinity or essential level of the target in the biological organism.

The mechanism of drug inhibition mainly relies on blocking an essential biological target element from functioning. The target elements can be monomers or a complex of multiple homosubunits; such as the biomotors of the hexameric ASCE superfamily[20, 38]. Conventional drugs are designed to target a single subunit molecule to inhibit pathogenesis, such as an enzyme or a structural protein of a virus. The key in designing potent drugs is to target multi-subunit biological motors, machines, or complexes with $Z>1$ and $K=1$, where Z is the stoichiometry of the complex and K is the number of drugged subunit that are required in order to block the function of the entire complex. Similarly, in a series circuit Christmas decorative light chain, one broken light bulb will turn off the entire lighting system.

In most, if not all, multi-subunit biological systems, sequential coordination or cooperative action mechanisms are utilized, thus, K equals 1. Drug inhibition depends on the ratio of drugged to the non-drugged complex. For $K=1$, and $Z>1$, inhibition efficacy follows a power function with respect to Z, leading to an increased potency of the drug since inhibition of any subunit results in complete inhibition of activity. For a drug designed to target a single-subunit molecule at targeting efficiency p, the fraction of undrugged target molecules q that will remain active is 1−p. In this situation, the inhibition efficiency is proportional to the substrate targeting efficiency p and the inhibition efficacy is of the first order of p. Sequential action or cooperativity in multi-subunit complexes has widely been reported in biological systems[39-41]. Drugs targeting a complex with multiple subunits can inhibit the complex activity if any homosubunit of the target is inactivated. Thus, if the copy number of this cooperative complex is $Z>1$, and the least number of blocked subunit to inhibit complex activity (K) is 1, the fraction of uninhibited biocomplexes is $q^Z$, and the inhibition efficiency is $1-q^Z$, where $1-q$ is the portion of drugged subunits.

The binomial distribution analysis allows prediction of the inhibition efficiencies. For example, in targeting a six-subunit biocomplex with K=1, the inhibition efficiency is determined by drug binding to any one of the six homosubunits. Therefore, the probability of inhibiting any subunit at random position is $$\frac{1-q^6}{1-q}$$

times higher than inhibiting a monomer substrate. With this new elucidation and understanding of the concepts behind targeting of cooperative multi-homosubunit complexes, a new generation of potent drugs may emerge in the near future.

Our discovery is an approach, not a drug. This approach will have general impact in the development of drugs for many diseases such as cancer, viral or bacterial infections. In living systems, biological machines or complexes with high stoichiometry and operated by sequential cooperative action or coordination with Z>1 and K=1 are ubiquitous. This class of biological machines is involved in many aspects of crucial cellular processes to the survival of viruses, bacteria, and eukaryotic cells. For example, multi-subunit biomotors are involved in chaperon, ATPase, ATP synthase, cell mitosis, bacterial binary fission, DNA replication, DNA repair, homologous recombination, Holliday junction resolution, nuclear pore transportation, RNA transcription, drug transporters, muscle contraction, viral genome packaging, as well as motion, trafficking, and exportation of cellular components. These systems use a sequential mechanism similar to the serial circuit of the Christmas decoration lighting chain. Thus, our approach will have broad application in drug development in many biological systems. Drugs targeting to these motors will be highly efficient.

Biomotors belonging to the multi-subunit ATPase are widely spread in organisms, including bacteria, viruses and cancer cells. Successful implementation of this new methodology will lead to the development of the next generation of potent drugs. In fact the first drug approved to treat multidrug-resistant tuberculosis, bedaquiline [4], is acting on the ATP synthase which is a multisubunit biomotor [100-111]. Treating multidrug-resistant tuberculosis had been very challenging previously. Although this drug's inventors were not aware of the concept of targeting multisubunit complexes for potent drug development, the success in this drug conquering the tough *Mycobacterium tuberculosis* organism supports the concept of using the multisubunit complex as a potent drug target. Cancer or bacterial mutant multi-subunit ATPase can be used as target. The drug developers can simply check the published literature and identify a multi-subunit machine as the drug target. For cancer treatment, it is to find a multi-subunit machine with mutation.

Figure 9:
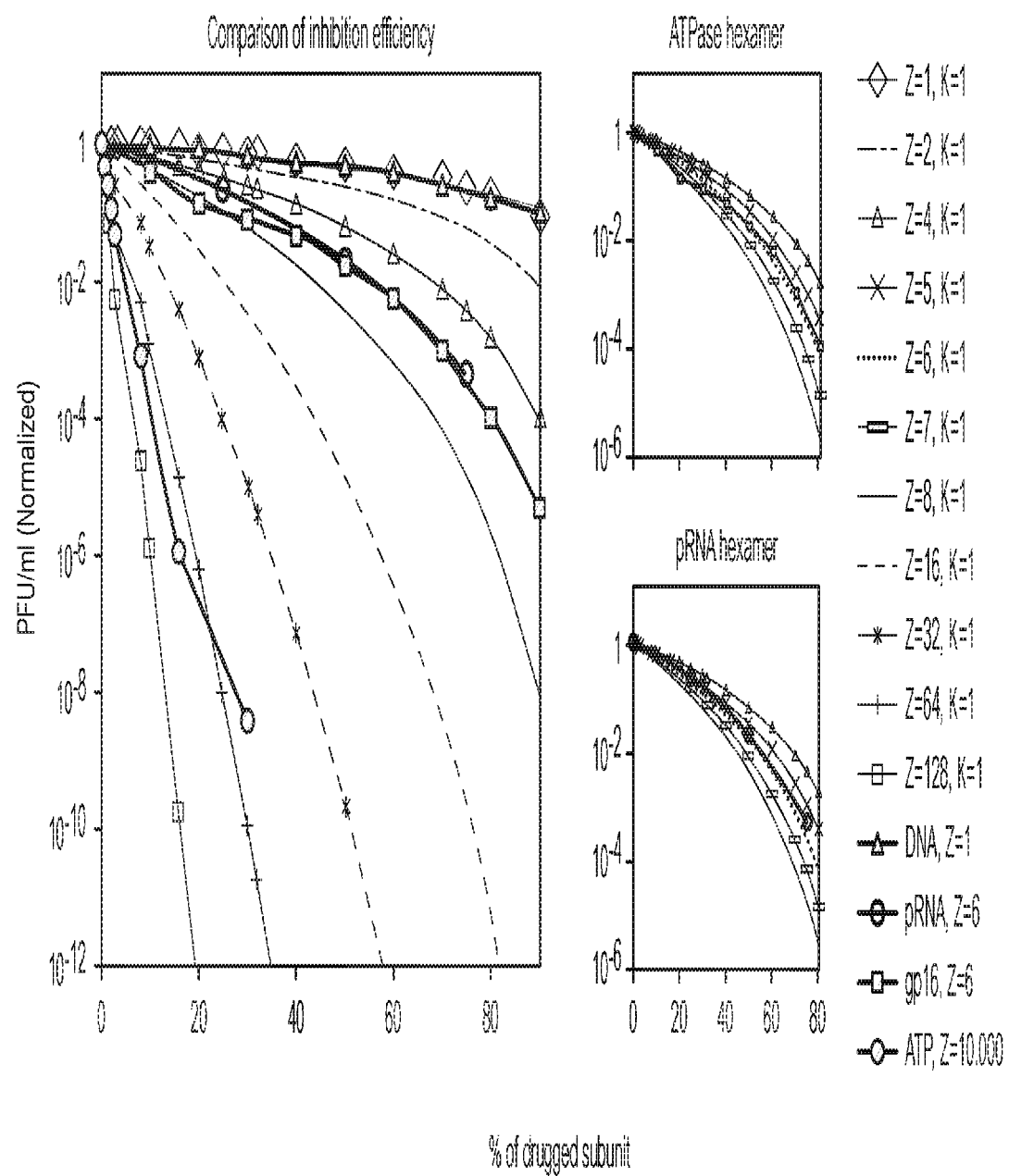
FIG. 9 compares Phi29 viral assembly inhibition efficiency by targeting components of the system with different stoichiometries (left panel), DNA with stoichiometry of 1, ATPase gp16 with stoichiometry of 6 (right upper panel), pRNA with stoichiometry of 6 (right lower panel), and ATP with stoichiometry of 10,000. Adapted from ref. [13] with permission.
Figure 10A:
FIGS. 10A-10D shows widespread biomotors or nanomachines that are composed of multisubunit complex.
Figure 10B:
Figure 10C:
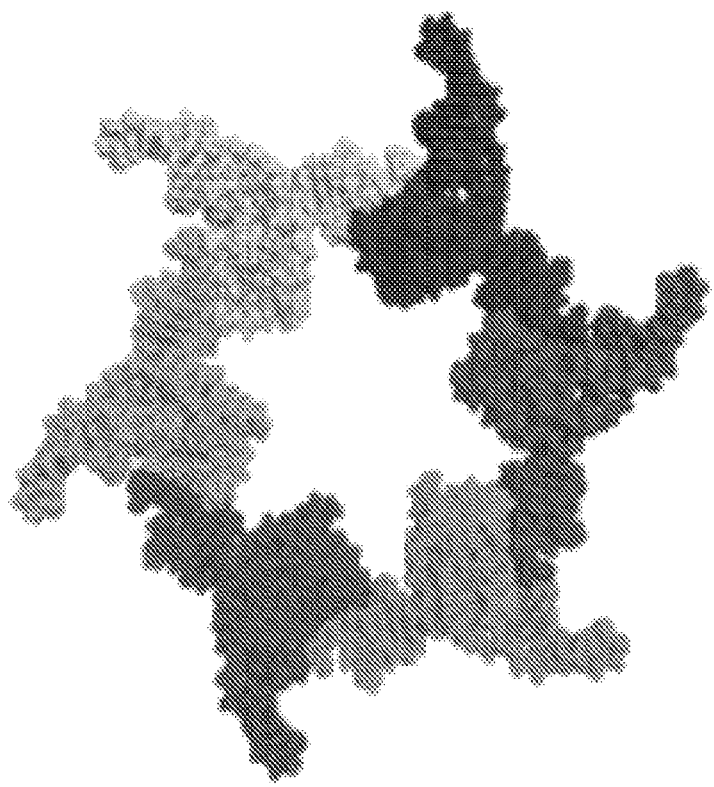
Figure 10D:
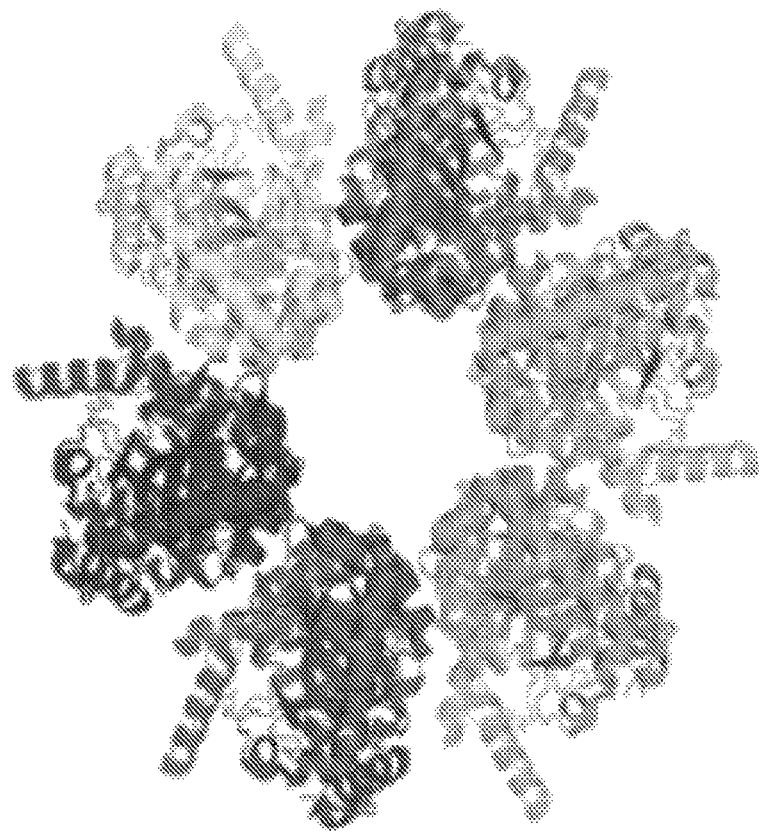
Figure 11A:
FIGS. 11A-11D show examples of homomeric multisubunit complex as drug target for developing potent drugs.
Figure 11B:
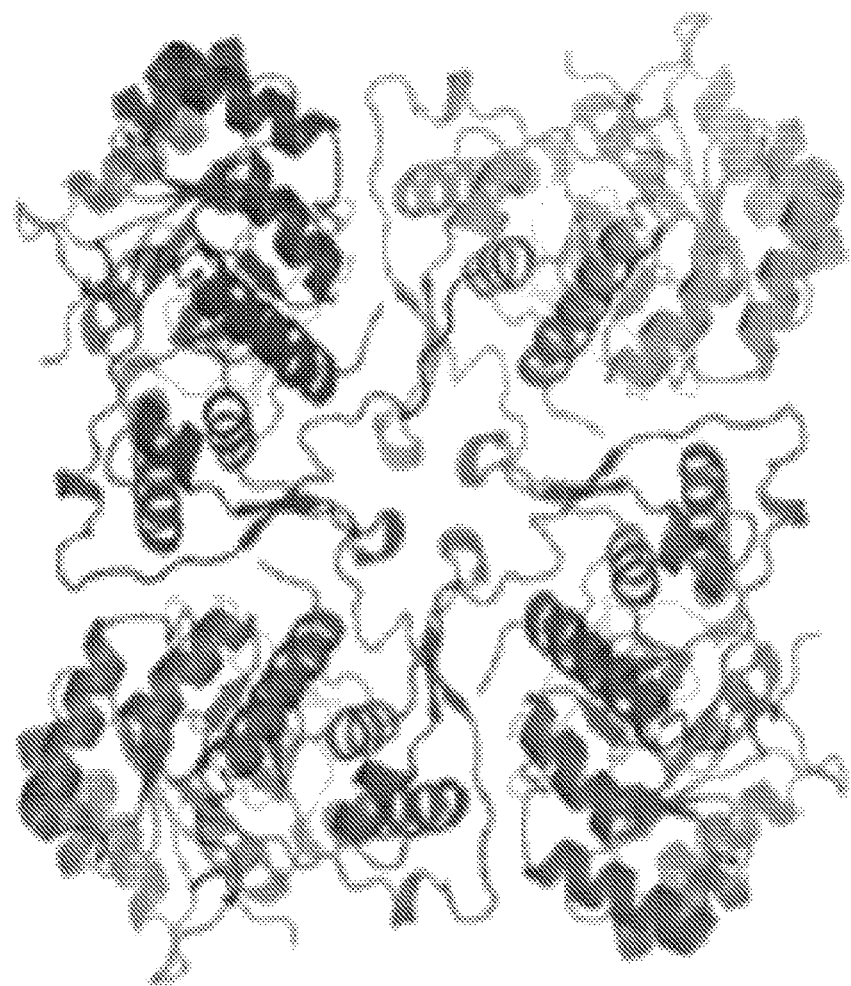
Figure 11C:
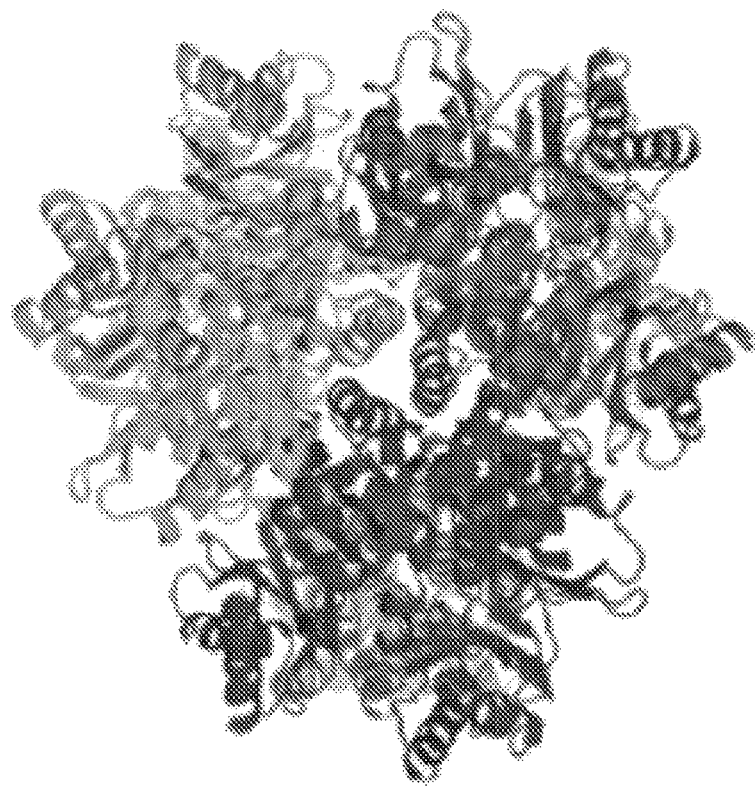
Figure 11D:
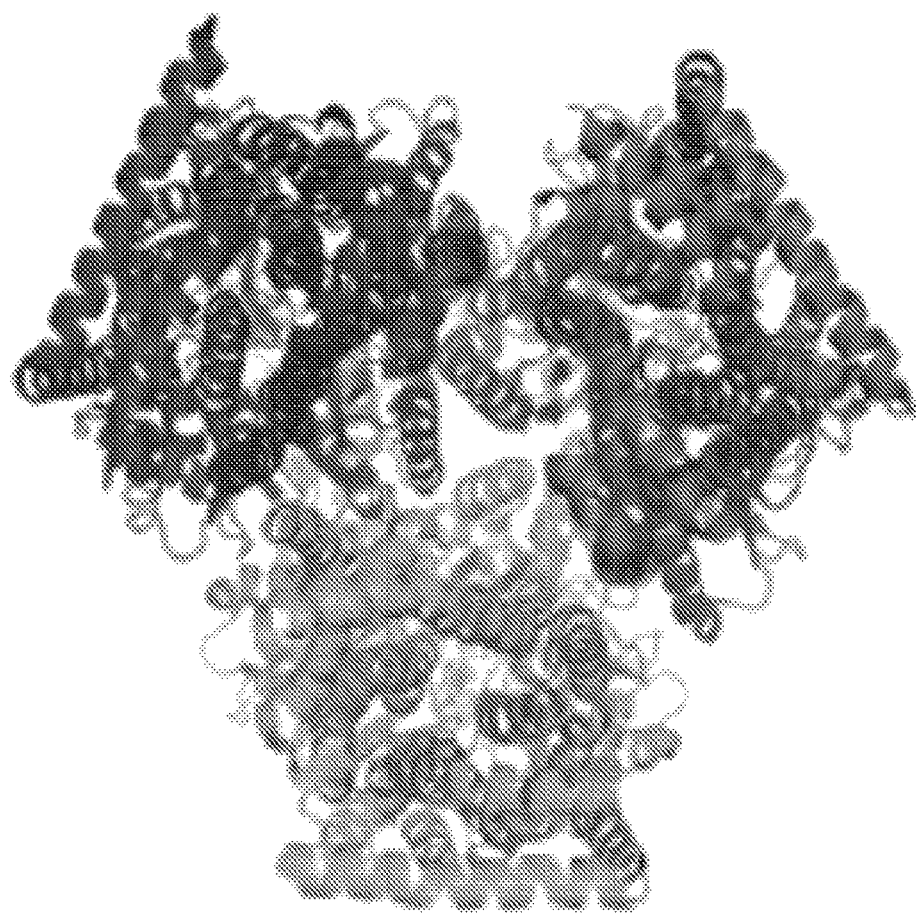

The concept of K=1 for high efficiency inhibition may be impactful in gene or protein therapy. By introducing the dominant negative protein[94] or inactive mutant protein into the cell, either by intracellular expression or direct introduction of proteins, which resembles the above illustrated approach and mechanism used for phi29 DNA packaging motor systems [13, 14, 45, 112](FIG. 9). This involves the incorporation of mutant proteins, either intracellularly expressed or directly introduced, into a highly multimeric complex that is identified as the target unit. For purposes of serving as a small molecule drug target, a multimeric complex might be identified, such that binding of one drug molecule to any one binding site on the complex will inactivate the whole complex. The fact that the complex composed of Z subunits holding one drugged subunit will only come into play as the drug concentration is at the high end. However, if the strategy was to express a dominant negative protein, as has been done in recent cardiac gene therapy with dominant negative phospholamban[94], a high inhibition efficacy will achieve. The greater the value of Z the more the effect of the dominant negative protein subunit or mutant subunit will be achieved.

Another possibility is the use of homomeric drug transporters [113, 114] as drug targets (see section 5.3). The mechanism of drug transporters is very similar to that of the revolution motor featuring an entropy transition induced by ATP. High stoichiometry of target complex is a key consideration for achieving high drug efficiency. Targeting multi-drug efflux transporters with high stoichiometry has a better chance to develop drugs for treating multi-drug resistant disease.

While the hypothesis behind this method might theoretically seem challenging, elucidation of the mechanism should greatly facilitate application of this approach. Two factors are essential for drugs development: efficiency and specificity. The strategy described herein focuses on drug efficiency, while specificity is similar to the general consideration in the development of chemicals and drugs. Nevertheless, design of potent drugs to common machines or general targets is still possible. For example, if an oncogenic mutant hexameric ATPase is found in one specific type of cancer cells, drugs targeting to this mutation of the altered ATPase will not only be highly efficient but also specific.

Using multisubunit homomeric complexes such as AAA+ family ATPase, biomotors or drug transporters with high stoichiometry could lead to development of highly potent drugs.

Most multisubunit complexes work in a sequential and cooperative manner, that is K=1, which is the key for these complexes to be used as target for potent drug development.

Bacterial virus Phi29 DNA packing motor contains many multisubunit components with different stoichiometries; it is a good model to elucidate the concept of stoichiometry in drug development.

Multisubunit nanocomplexes such as biomotors or ATPase are widely spread in nature. Thus, the method should have broad application in the development of new drugs. For example, the use of ATP synthase as drug target has led to the development of a new drug for treating multidrug resistant tuberculosis.

Section 3

Abstract

Aims:

To find a method for developing potent drugs and to prove a hypothesis that drug inhibition potency depends on the stoichiometry of the targeted biocomplex.

Methods:

Phi29 DNA-packaging motor components were used to test this model for different stoichiometries. Viron assembly efficiency was assayed with Yang Hui's Triangle:

$$(p+q)^Z = \sum_{M=0}^{Z} \binom{Z}{M} p^{Z-M} q^M,$$

where Z=stoichiometry, M=drugged subunits in each biocomplex, p and q represent the fraction of drugged and non-drugged subunits in the population.

Results:

Inhibition efficiency follows a power function. When number of drugged subunits to block the function of the biocomplex K=1, the fraction of uninhibited biocomplex equals $q^z$. Thus, stoichiometry has a multiplicative effect on inhibition. Targets with a thousand subunits showed the highest inhibition effect, followed by those with six and a single subunit. Complete inhibition of virus replication was found when Z=6.

Conclusion:

Drug inhibition potency depends on the stoichiometry of the targeted components of the biocomplex or nano-machine. The inhibition effect follows a power function of the stoichiometry of the target biocomplex.

Introduction

Bacteria, viruses and cells contain biocomplexes and nanomachines composed of multiple subunits, such as biomotors, pumps, exosomes, valves, membrane pores, chaperonins, PCNA, ATPase, and tubes. From a nanobiotechnological standpoint, these nanomachines can be used and converted to build sophisticated nano-devices including molecular sensors, patterned arrays, actuators, chips, microelectromechanical systems (MEMS), molecular sorters, single pore DNA sequencing apparatus or other revolutionary electronic and optical devices. From a pharmaceutical standpoint, these multi-subunit biocomplexes or nanomachines have a potential for use as drug targets for therapeutics, as well as diagnostic applications such as pathogen detection, disease diagnosis, drug delivery, and treatment of diseases. In the ASCE (Additional Strand Catalytic E) family including the AAA+(ATPases Associated with diverse cellular Activities) and the FtsK-HerA superfamily in bacteria, viruses and cells, there are nanomotors that perform a wide range of functions critical to chromosome segregation, bacterial binary fission, DNA/RNA and cell component transportation, membrane sorting, cellular reorganization, cell division, RNA transcription, as well as DNA replication, riding, repair, and recombination. One of the directions of NIH Roadmap is to utilize these cellular nanomachines and biocomplexes for biomedical applications.

Acquired drug resistance has become a major reason for failure treatment of a range of diseases, i.e., the chemotherapy for cancer, bacterial or viral infections. Drug resistance of cancer has escalated and has partially contributed to the ~600,000 deaths in the USA in 2012. HIV drug resistance has also become a major issue. Many common pathogens have become resistant to current drug treatments, with new infectious diseases on the rise. The use of multidrug-resistant agents in biological weapons has created a previously unrealized challenge. Thus, there is a need to develop new treatment strategies to combat drug resistance with new drug development methods.

The first FDA-approved drug to treat multidrug-resistant tuberculosis, bedaquiline, follows a new mechanism of inhibiting the bacterial ATP synthase of *M. tuberculosis* and other mycobacterial species, but had little activity against other bacteria. To combat multidrug resistance in cancer, several approaches have been explored. One method is to target components that are highly important for the growth of the biological entity. Another approach uses nano-drug delivery carriers that are expected to enhance the binding efficiency of drugs to cancer cells, or cocktail therapy. A third approach is to develop new combinational drugs with higher potency by acting on multiple targets. This involves identifying multiple targets that when treated leads to a synergetic effect and optimizing the design of multi-target ligands.

The approach of developing highly potent drugs through targeting of protein or RNA complexes with high stoichiometry has never been reported due to challenges in comparing efficacies of two drugs that can be confused by target essentiality with binding affinity. For instance, if two drugs target two stoichiometrically different targets, it becomes extremely difficult to prove whether the difference in drug efficiency is due to differences in their target binding affinity or essential level in the growth of the biological organism. In order to quantify effects from targeting biocomplexes of different stoichiometry, a well-studied multicomponent system is required that allows empirical comparison of functional inhibition of individual components that are composed of different number of subunits.

An example of one nanobiomachine is the dsDNA translocation motor, for which the ATPase protein is a pivotal component that assembles into a hexameric ring structure and translates the action of ATP binding and hydrolysis into mechanical motion to translocate DNA physically. The DNA packaging motor of bacteriophage phi29 (FIG. 12A) is composed of three essential co-axial rings: 1) a dodecameric connector ring located at the vertex of the viral procapsid; 2) a hexameric packaging RNA (pRNA) ring (FIG. 12A, B) bound to the N-terminus of the connector, and 3) a hexameric ring of ATPase gp16 attached to the helical region of pRNA, powered through the hydrolysis of ATP resulting in DNA packaging. The use of Yang Hui's Triangle or binomial distribution to determine the stoichiometry of the pRNA was first reported in 1997. The use of similar mathematical methods to determine the stoichiometry of the protein subunits has also been reported more recently. The copy number of ATP molecules required to package one full phi29 genomic dsDNA was predicted to be 10000. It has recently been shown that this hexameric motor uses a revolution mechanism without rotation to translocate its genomic DNA.

In this report, we hypothesize that the inhibitory efficiency of a drug is related to the stoichiometry of its targeted biocomplex; the higher the stoichiometry of the target complex, the more efficient the drug. This can lead to the development of potent therapeutics against high-stoichiometric biomachines or biocomplexes as drug targets. We proved this hypothesis by using a mutant subunit as the drugged inactive target to calculate the theoretical inhibition efficiency via binomial distribution, and compared with experimental data from a defined in vitro viral assembly system. Since biomotors share certain common structures and operation mechanisms, the approach in drug development reported here should have general applications especially in developing new generations of drugs for combating the rising acquired drug resistance in viruses, bacteria, and cancers.

Materials and Methods

Preparation of Mutant Genomic dsDNA

Phi29 genomic DNA-gp3 was purified from *B. subtilis* SpoA12 cells by CsCl gradient ultracentrifugation as described previously. Mutant dsDNA was prepared by digesting the phi29 genomic dsDNA with EcoR1 restriction enzyme in fast digest buffer (Fermentas) at 37° C. for 1 hour followed by ethanol precipitation. The mutant DNA was tested by 1% agarose gel electrophoresis, stained by ethidium bromide (Sigma) and imaged by Typhoon (GE).

Preparation of Mutant pRNA

Wild-type phi29 pRNA and inactive mutant as drugged pRNA were prepared by in vitro transcription. In the inactive mutant pRNA, the first four bases "UUCA" (SEQ ID NO: 11) located at the 5' end were mutated to "GGGG" (SEQ ID NO: 11). BglII digested plasmid pRT71 was used as DNA template in the PCR reaction for both RNAs. Oligonucleotide 5'-TAA TAC GAC TCA CTA TAG GGG TGG TAC-3' (SEQ ID NO: 12) and 5'-TTA TCA AAG TAG CGT GCA C-3' (SEQ ID NO: 13) were used as primers for mutant pRNA. RNAs were then transcribed by T7 RNA polymerase using double-stranded DNA generated from PCR, as described before. The RNA from in vitro transcription was further purified by 8 M urea 8% polyacrylamide gel electrophoresis as described previously.

Preparation of Mutant ATPase Gp16

The purification of wild-type gp16 has been described previously. The walker B mutant gp16 was constructed by introducing mutations in the gp16 gene. The amino acid residues D255 and E256 in walker B motif of gp16 were mutated to E255 and D256, respectively. The mutation was introduced with the Stratagene Quick Change site-directed mutagenesis kit using appropriate primers. The expression and purification of protein were carried out followed a published procedure.

Antisense Oligonucleotides

Antisense oligonucleotides P3 and P15 were designed to be reversely complementary to different regions on the pRNA molecule and chemically synthesized by IDT. P3 oligo (5'-TTGCCATGATTGACAAC-3' (SEQ ID NO: 14)) targets the region of 83-99 nucleotides at the 3'end of pRNA. P15 oligo (5'-AAGTACCGTACCATTGA (SEQ ID NO: 15)) targets the region of 1-17 nucleotides at the 5'end of pRNA. P8 oligo (5'-TAATACGACTCAC-TATAGGGGTGGTAC-3' (SEQ ID NO: 16)) was designed as a non-targeting control in the test. 1 μl of individual oligos at 100 μM were mixed with 1 μl of pRNA at 4 μM and dialyzed on a 0.025 μm type VS filter membrane (Millipore Corp) against TBE buffer (89 mM Tris-HCl, pH 8.3, 89 mM boric acid, 2.5 mM EDTA) at room temperature for 15 min. The purified RNA complex was used for in vitro phi29 assembly assay.

In Vitro Phi29 Assembly Assay

Purified components were subjected to in vitro viral assembly assay as described previously. Briefly, 10 μg of purified procapsids were mixed with 100 ng of pRNA in 5 μl of reaction buffer (10 mM ATP, 6 mM 2-mercaptoethanol, and 3 mM spermidine in TMS buffer) at room temperature for 30 min. Purified DNA-gp3 and gp16 were then added and the reaction mixture was incubated at room temperature for one hour to initiate DNA packaging. Finally, the DNA filled procapsids were incubated with 10 μl of gp8.5-9 extract from E. coli containing plasmid pARgp8.5-9 and 20 μl of gp11-14 extract from E. coli to complete the infectious phage assembly.

The newly assembled infectious viruses were plated with inoculated B. subtilis bacteria Su$^{+44}$ cells onto a half LB plate covered with top agar. After 12 hour incubation at 37° C., the viral assembly efficiency (plaque-forming unit, PFU) was calculated by counting the formed plaque numbers. Mixing different ratios of mutant with wild-type components, while keeping all other components the same, the viral assembly efficiency (PFU) versus ratio of mutant components gave an empirical curve for vial assembly inhibition assay, and it was compared with theoretical curves from the binomial distribution equation.

In Vivo Viral Assembly Assay

Plasmid pRBwtRNA containing the pRNA coding sequence under T7 promoter was constructed by ligating the fragment coding pRNA sequence and T7 promoter into pRB381-L550 vector (modified and kindly provided by M. Wang and H. Zalkin) following a previously described method. Plasmid pRBmutRNA contained mutant pRNA under its natural promoter PE1 sequence, and the mutation was changing sequence 5'UUGA-3' (SEQ ID NO: 17) at its 3'end to 5'GGGG-3'(SEQ ID NO: 18). The DNA fragments coding mutant pRNA sequence and PE1 sequence were prepared by PCR as described previously; and digested with HindIII-BglII restriction enzyme. The mutant pRNA sequence coding fragment was further ligated with a 6.0 kb fragment from pRB381-L550 that was digested with HindIII and partially digested with BglII.

The plasmids pRBmutRNA, pRBmutRNA, and pRB381-L550 were transformed into B. subtilis cells following methods described previously. The B. subtilis cells harboring transformed plasmids were incubated in 416 medium with 10 mg/ml of neomycin for 3 hours at 37° C. and then plated onto LB-neomycin (10 mg/ml) plates for plaque formation analysis.

Results

The Definition of "Stoichiometry".

The definition of the stoichiometry in this report is different from conventional definition of stoichiometry used to evaluate drug efficiency. Conventionally the concept of stoichiometry refers to the number of a drug binding to each target molecule, which is also known as $B_{max}$. In this study the definition of stoichiometry refers to the copy number of subunit within a biocomplex or the nanomachine that serves as drug target.

The Definition of "K Value", and K=1 is One Key for Ultra-High Inhibition Efficacy Suppose a biocomplex drug target contains Z copies of subunits, then K is the copy number (K≤Z) of drugged subunits required to inhibit the function of the complex or the nanomachine. As an analogy to the difference between the parallel circuit and the serial circuit, when the Christmas lights are arranged in a parallel circuit, any light bulbs that are burnt out will not affect other bulbs. But in a serial circuit, any one light bulb that is broken will stop the entire lighting system, which is K=1. Thus, the K value is the key to the probability of inactive nanomachines or biocomplexes by combination and permutation of all subunits. K equals 1 is critical for such ultra-high inhibition effect. The foundation of the approach in this report is the difference in probability of inhibited biocomplexes in systems of different K values with combination and permutation algorithms. Biological systems display complicated reactions. Many reactions involve multiple subunits to work cooperatively sequentially or precessively to accomplish one essential biological function. Single assembly pathways have been reported in the viral assembly system. In most cases of the sequential, cooperative, and processive action, inactivation of any one, not necessary all, of the subunits will result in inhibition of its function, thus K=1. Drug synergism was utilized in multi-target drug therapy; in short, a drug combination can simultaneously act on multiple targets in disease networks to produce a synergistic effect. However, our design reported here is unique from the conventional synergistic approach. We suggest that using multi-subunit biocomplexes as drug target could lead to development of ultra-high potent drugs. In a conventional six-component system, for example one drug is designed to target component #3 to stop the entire system, since the drug can only target component #3, the condition fits the model of Z=1 and K=1. Thus, the inhibition efficiency and substrate targeting efficiency (p) of drug will be in linear relationship. However, in the system in this report, the entire system will be blocked when drug targets any subunit of a hexamer, which is Z=6 and K=1. Thus the probability of remaining undrugged targets will be $q^6$, where q represents the fraction of untargeted hexamer subunits; in other words, the drug inhibition efficiency will be $1-q^6$, which increases following a power function compared to the linear for conventional mono-subunit approaches.

Assuming that at least K copies of drugged subunits were needed to deactivate the nanomachine or biocomplex, the probability of functional biocomplexes in the presence of various ratios of inhibited and wild-type subunits could be predicted from equation 2. When K=1, it implies that drug binding to one subunit will inactivate the subunit, and one drugged subunit per multi-subunit complex is sufficient to inhibit the overall function of the complex. The inhibition efficiency by drugs targeting multi-subunit biocomplexes with stoichiometry of Z will equal $1-q^2$, as shown in table 2. An example for such a probability calculation when Z=6 and K=1 is as follows: since it was assumed that 6 (Z=6) copies of subunits per element were required for function and one drugged subunit (K=1) was sufficient to block its activity, all elements possessing 1 to 5 copies of drugged subunits would be non-functional (FIG. 1C). Only those complexes possessing 6 copies of normal subunits will be functional. The chance for a complex containing 6 copies of unaffected subunits in a population is $q^6$ and the inhibition efficiency will be $1-q^6$.

Rationale Behind Selection of Multi-Subunit Biocomplexes as Efficient Drug Targets Mechanisms for drug inhibition of organism growth are to block or stop an essential biological element from functioning. When a drug is designed to target the subunit of a complex with targeting efficiency p, a fraction of subunits will not interact with the drug (a percentile given as q, p+q=1) and will remain active and exert their function properly. Some biological elements are monomers containing only one subunit, while other biological elements, such as the bin-motors of hexameric AAA+ family, consist of multiple-subunits. Conventional drugs are designed to inhibit pathogenesis through targeting of a single subunit molecule, such as an enzyme or a structural protein of a virus. In this situation, the inhibition efficiency is proportional to the substrate targeting efficiency p and the effect is proportional to the first order of p. As described above, in most cases of sequential action or cooperatives in multiple subunit complexes, inactivation of one, not all, of the subunits will result in inhibition of its function. Thus, if complexes containing Z copies of subunits exercise their function in a sequential and cooperative way, then K=1, and the fraction of the uninhibited active biocomplex will be $q^z$, a higher order with regards to the stoichiometry. The inhibition proportion will equal $1-q^z$.

In this investigation, a well-defined in vitro phi29 viral assembly system was used to represent a multi-subunit nano-machine target, with the mutant component representing a target component that have been inactivated by an effective drug. Then, the inhibition efficiencies by targeting different elements of the phi29 DNA packaging motor with different stoichiometry were compared. The viral assembly competition assays combined with binomial distribution analysis illustrated the concept that drug targeting functional biological complexes of a higher-stoichiometry has a higher efficiency than drug acting on a single subunit target.

When the target element is a monomer containing only one subunit, the inhibition efficiency can be calculated through a binomial distribution (equation 1), where p and q are the fractions of drugged (substrate targeting efficiency) and undrugged (normal active elements) subunits, respectively (p+q=1).

$$X=(p+q)^1 \tag{1}$$

However, when the target element contains multiple subunits, a high order binomial distribution (equation 2) is applied to calculate the drug inhibition effect by finding the ratio of resulted active and inactive complexes, where Z represents the total number of subunits (the stoichiometry) in one biocomplex and M represents the number of drugged subunits in one biocomplex.

$$X = (p+q)^Z = \sum_{M=0}^{Z} \binom{Z}{M} p^{Z-M} q^M = \sum_{M=0}^{Z} \left(\frac{Z!}{M!(Z-M)!}\right) p^{Z-M} q^M \tag{2}$$

Note that the binomial distribution as set forth in equation 2 may also be expressed as follows:

$$\sum_{M=0}^{Z} \binom{Z}{M} p^M q^{Z-M} = \sum_{M=0}^{Z} \left(\frac{Z!}{M!(Z-M)!}\right) p^M q^{Z-M}$$

Computational results based on the binomial equation are set forth herein. The context of the results governs which form of the equation is used.

For example, if Z is 3, the probability of all combinations of drugged subunits (M) and undrugged subunits (N; M+N=Z) in a given biocomplex entity can be determined by the expansion of equation 2: $(p+q)^3=p^3+3p^2q+3pq^2+q^3=1$. That is, the probability of a complex element possessing three copies of drugged subunits in the population is $p^3$, two copies of drugged and one copy of undrugged or wild-type subunit is $3p^2$ q, one copy of drugged and two copies of undrugged subunits is $3pq^2$, and three copies of undrugged subunits is $q^3$. Assuming there were 70% (p=0.7) of subunits inactivated by bound drugs, and 30% (q=0.3) unaffected subunits in the population, then the percentage of elements possessing at least two copies of normal subunits would be the sum of those possessing one copy of drugged and two copies of undrugged wild-type subunits, $3pq^2$, and those possessing three copies of native subunits is $q^3$. That is $3pq^2+q^3=3(0.7)(0.3)+(0.3)^3=0.216=21.6\%$. In another example, if one complex contains 6 subunits, and 5 out of the 6 subunits need to remain uninhibited in order to be biologically functional, the active complex ratio in the population will be the sum of: 1) the probability of each element containing 5 undrugged subunits, and 2) the probability of each element containing 6 undrugged subunits.

The probability X in the population displaying a certain combination of undrugged versus drugged subunits can be predicted by a binomial distribution, as shown in equation 2. Table 1 shows the probability of a given element with M drugged and N undrugged subunits at increasing percentages of drugged subunits in the population, considering that the total subunits in one element (Z) is 3 or 12. The formula, $$\frac{Z!}{M!N!} p^M q^N$$

Figure 12A:
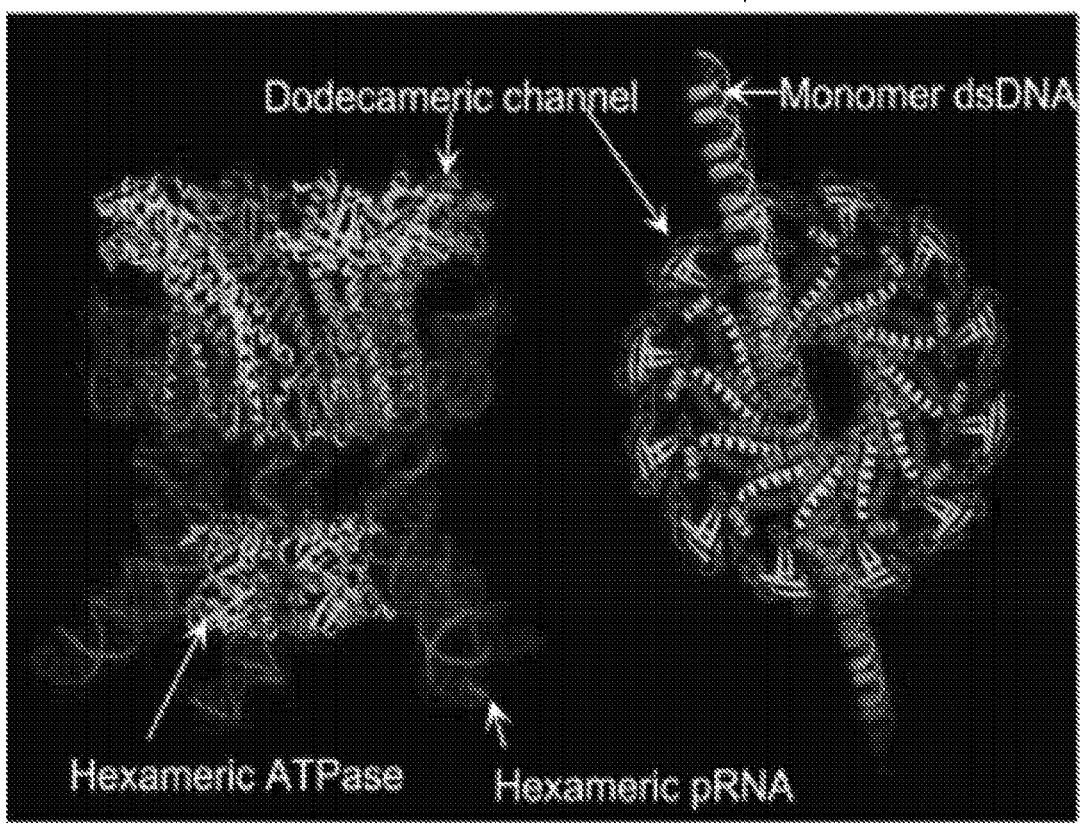
FIGS. 12A-12F show the stoichiometry of viral DNA packaging motor
Figure 12B:
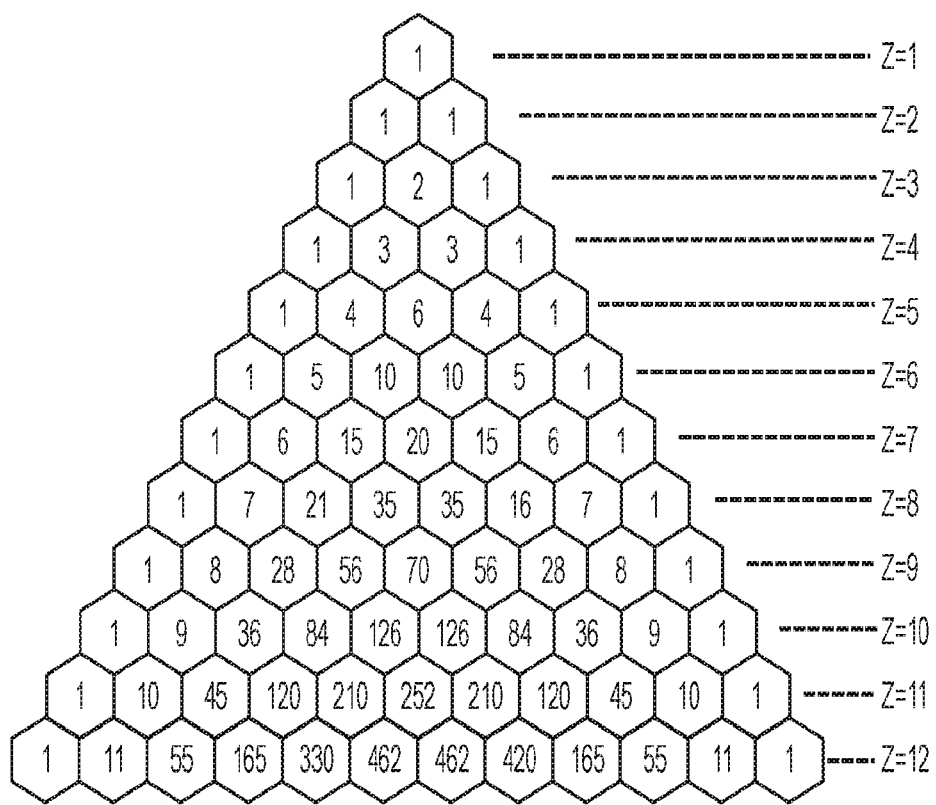
Figure 12C:
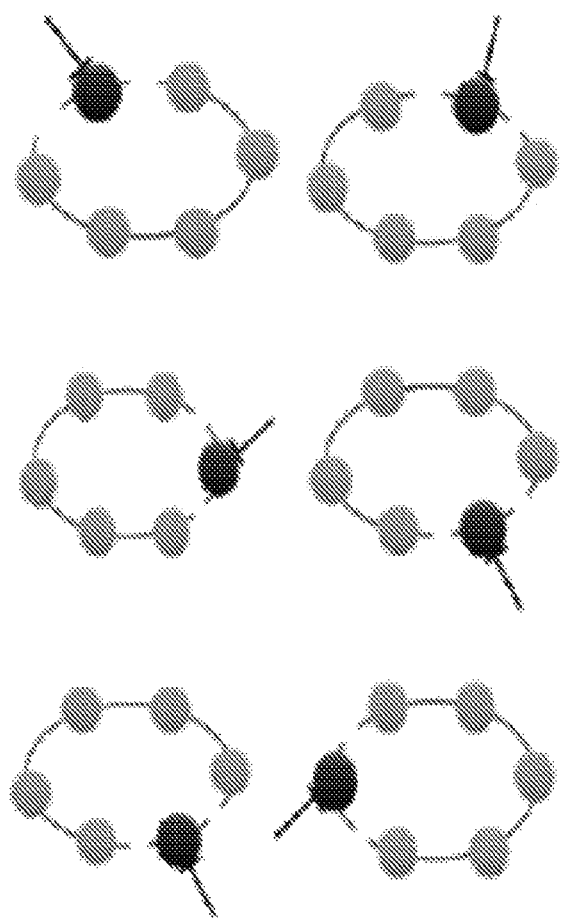
Figure 12D:
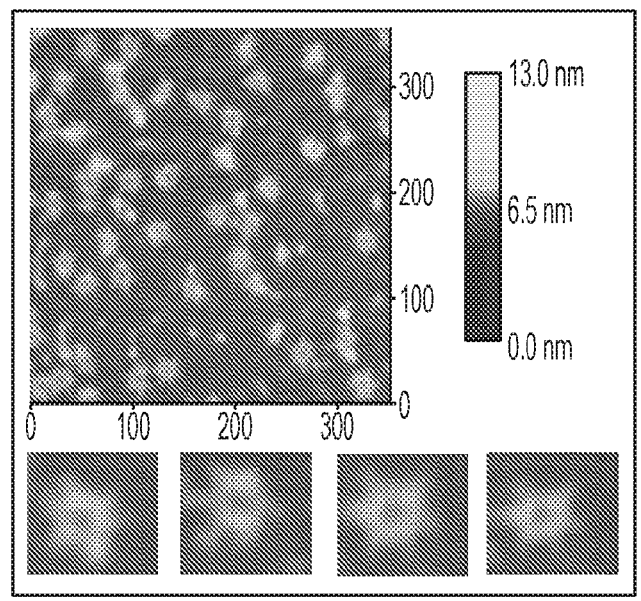
Figure 12D:
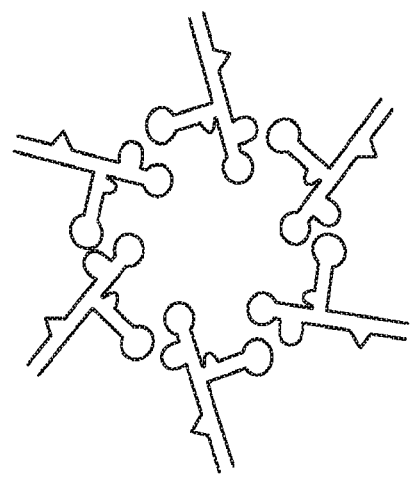
Figure 12E:
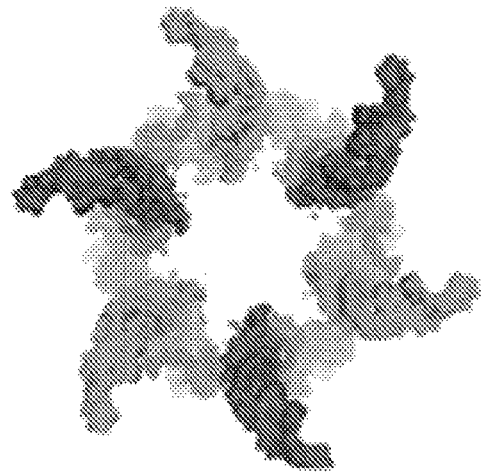
Figure 12E:
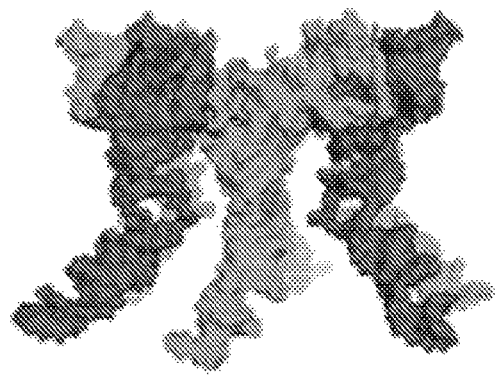
Figure 12F:
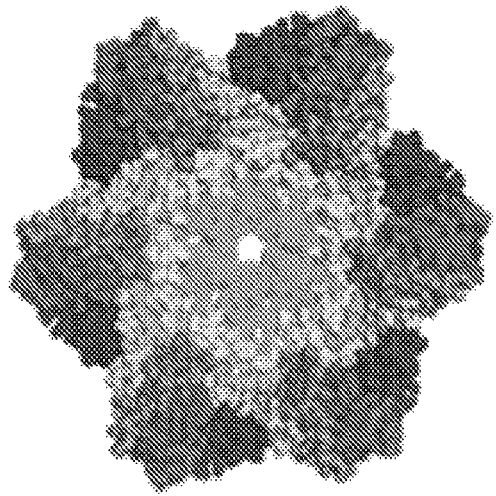
Figure 12F:
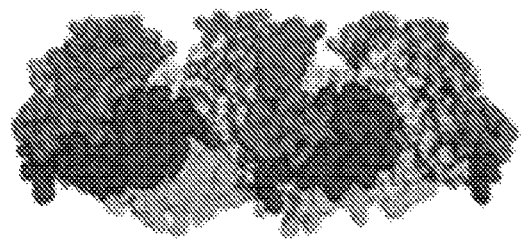

(from equation 2) was used to calculate each combination probability value, the coefficient $$\frac{Z!}{M!N!}$$

in this equation can also be calculated using Yang Hui Triangle, which is also called Pascal's Triangle, or binomial distribution (FIG. 12B).

In Vitro Virus Assembly System Used for Testing the Hypothesis

Figure 12G:
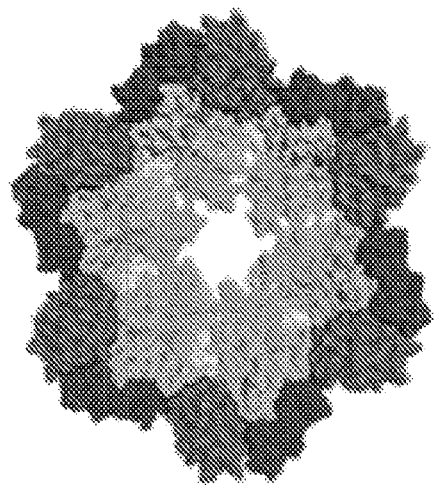
FIG. 12G is a structure of the hexameric AAA+ molecular machine ClpC with adaptor protein MecA. (PDB ID: MecA-ClpC, 3PXG).
Figure 12G:

The highly sensitive in vitro phi29 assembly system was used to determine the inhibition efficiency of drugs targeting multi-subunit complexes. Bacteriophage phi29 DNA packaging motor contains one copy of genomic dsDNA, 6 copies of packaging RNA, 6 copies of ATPase protein gp16 and more than 10000 copies of ATP. The stoichiometry of RNA in phi29 has been proven by extensive studies including single-molecule studies AFM images (FIG. 1D), pRNA crystal structure determination (FIG. 1E), and mathematical studies. The stoichiometry of gp16 in phi29 has been proven by multiple approaches including native gel binding, capillary electrophoresis assays, Hill constant determination, and by titration of mutant subunits using binomial distribution. Many other AAA+ superfamily members have been found to be hexamers as well, such as a red type rubisco activase AAA+ protein CbbX (FIG. 12F), MecA-ClpC molecular machine (FIG. 12G). The copy number of ATP molecules was calculated based on the fact that 6 ATP molecules are required to package one pitch of dsDNA with 10.5 basepairs (hp), thus 1 ATP is used to package 1.7 bp. The entire phi29 genome is composed of 19.4 kbp, thus, it is expected that more than 10000 ATP molecules are required to package the entire phi29 genome. The phi29 DNA nano-motor which packages an entire genomic DNA into the procapsid can be treated as a disease model for drug inhibition efficiency analysis.

In Vitro Testing of the Hypothesis Using DNA Element with Stoichiometry of 1

Figure 13A:
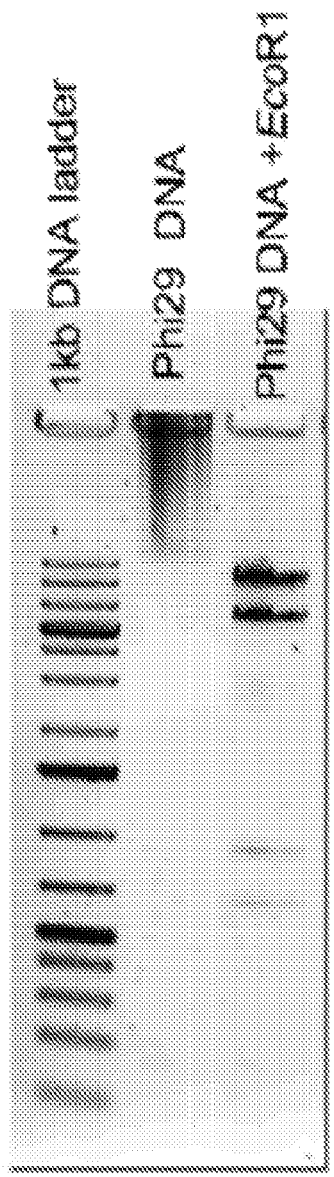
FIGS. 13A-13C show a theoretical plot (with variable Z) and empirical data to illustrate inhibition efficiency with drug targeting to genomic DNA (Z-1).
Figure 13B:
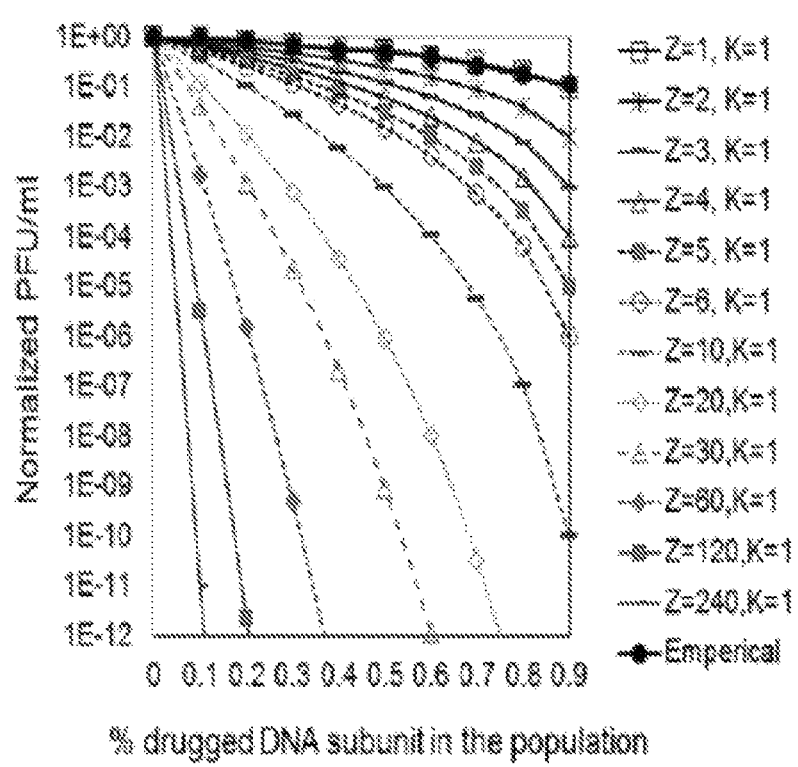
Figure 13C:
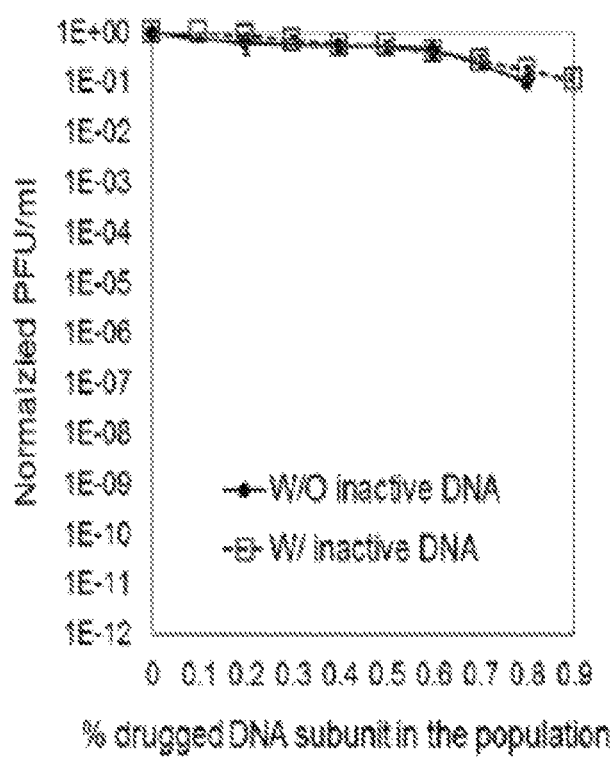

The inhibition efficiency of drugs targeting a single subunit substrate was tested by in vitro phi29 assembly inhibition by mutating the genomic dsDNA (FIG. 13A). Various ratios of mutant DNA were mixed with wild-type DNA in in vitro viral assembly assays. The empirical curve of viral assembly efficiency against drugged mutant DNA ratio fits well with the theoretical curve from binomial distribution for Z=1 and K=1 (FIG. 13B). This suggests that when designing drug targeting the genomic DNA in phi29 nano-motor, it is expected to be a first order inhibition response. Comparing the in vitro phi29 assembly inhibition, by adding drugged mutant DNA, with simply diluting wild-type DNA concentration as a control, revealed that the drugged mutant DNA didn't cause much difference (FIG. 13C). The results showed that the inhibition effect of drugs targeting the substrate with stoichiometry of 1 is minimal.

In Vitro Testing of the Hypothesis Using RNA Elements with Stoichiometry of 6

Figure 14A:
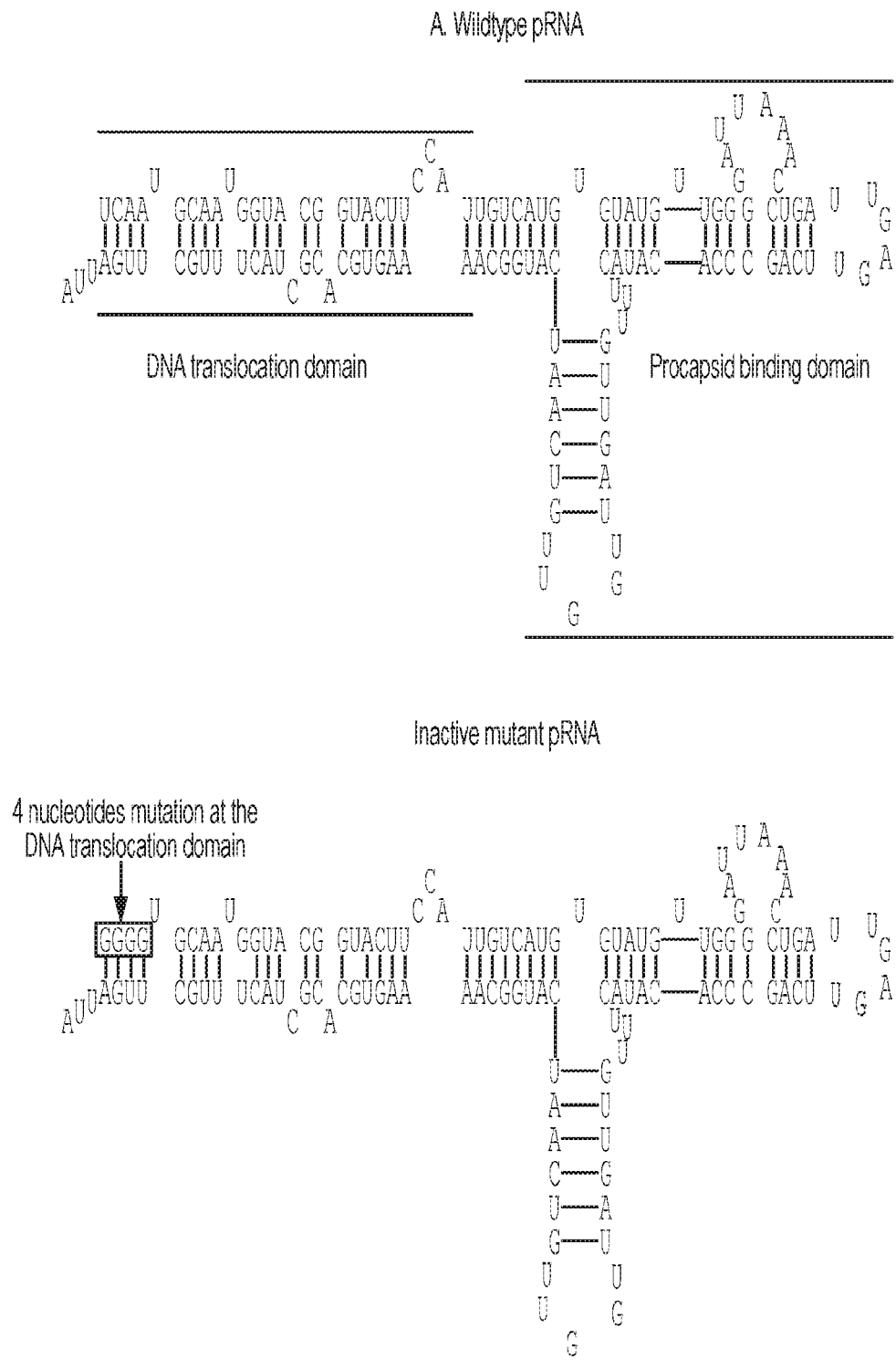
FIGS. 14A-14C is a theoretical plot (K=1 to 6) and empirical data to illustrate inhibition efficiency with drug targeting pRNA (Z=6).
Figure 14B:
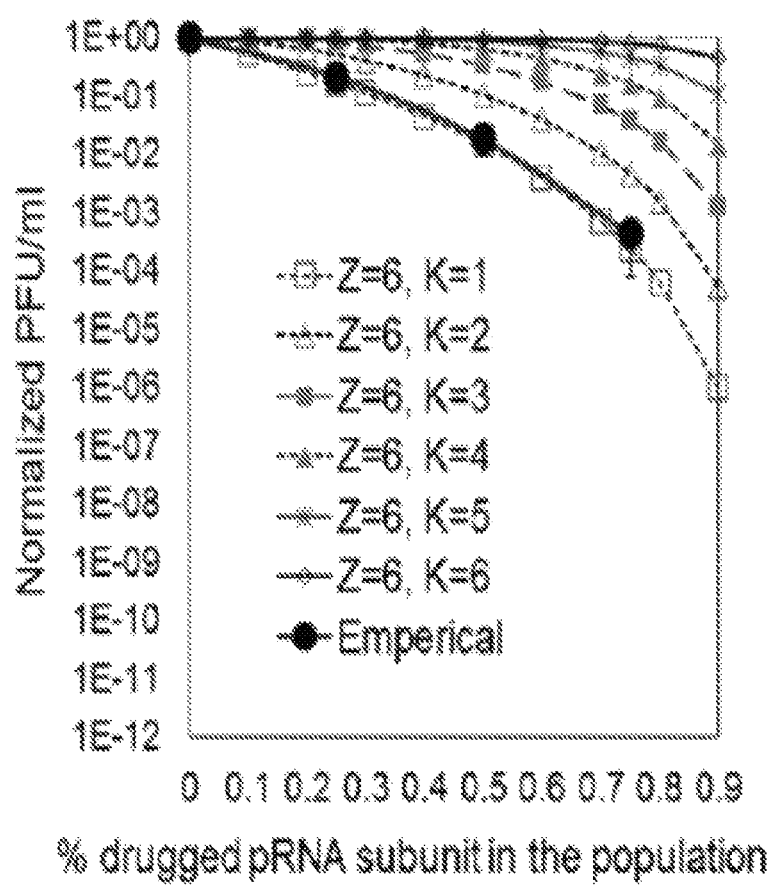
Figure 14C:
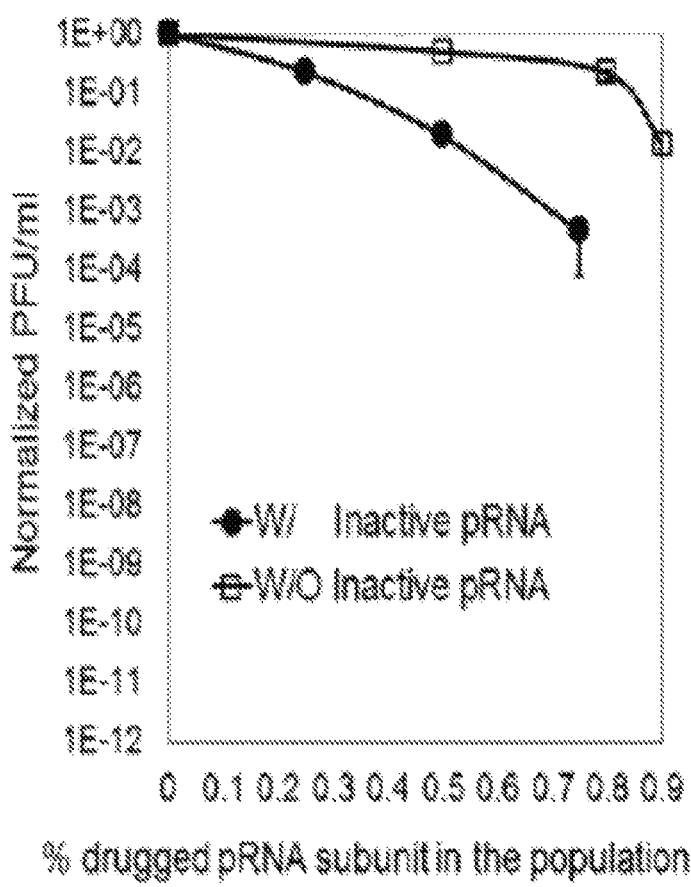

The pRNA of phi29 contains two domains; a head-loop domain essential for procapsid binding and a helix domain essential for DNA translocation (FIG. 14A, upper panel). The right-hand loop and left-hand loop of two pairing pRNA molecules can interact with each other by complementary base pairing. Extensive studies have led to the conclusion that 6 copies of pRNA form a hexameric ring which binds to the procapsid for virus activity. Drugged mutant pRNA was constructed by mutating 4 nucleotide sequences at the 5'end region of pRNA (FIG. 14A, lower panel), which has been shown to compete with wild-type pRNA for procapsid binding, but was found to be deficient in allowing DNA packaging to occur. The theoretical curves generated using the expansion of binomial distribution equation while total subunit number Z is 6 and varying K number from 1 to 6 are shown in FIG. 14B. Fitting the empirical data from phage assembly efficiency at different ratios of drugged mutant pRNAs into the theoretical curves, the empirical data fit into the theoretical curve of Z=6 and K=1. It suggested that the pRNA oligomer ring is composed of six copies of pRNA subunits and one subunit of the pRNA multimer blockage is sufficient to block the phage assembly activity. Comparing the empirical curve for viral assembly efficiency against different ratios of drugged mutant pRNAs with the wild-type pRNA concentration dilution control, addition of drugged mutant pRNA showed a much stronger inhibition effect (FIG. 3C).

To further prove the concept that drugs targeting biocomplex with high stoichiometry causes stronger inhibition effect, antisense oligonucleotides which can bind to pRNA molecules were designed as mock drugs in the viral assembly assay. The oligonucleotides P15, and P3 were designed to target the 5'-end and 3'-end regions on pRNA, respectively. It was confirmed that the antisense oligonucleotides can be hybridized to pRNA by gel shift assay (data not shown). When mixing the antisense oligonucleotides with wild-type pRNA for in vitro phi29 assembly assay, complete inhibition effects were shown by antisense oligonucleotides P15, and P3, but not with the non-targeting control oligonucleotide P8. By mixing the non-targeting oligo P8 with pRNA, it generated plaques with $4.4 \times 10^6$ PFU on the plate.

In Vivo Testing of the Hypothesis Using RNA Elements with Stoichiometry of 6

Figure 15A:
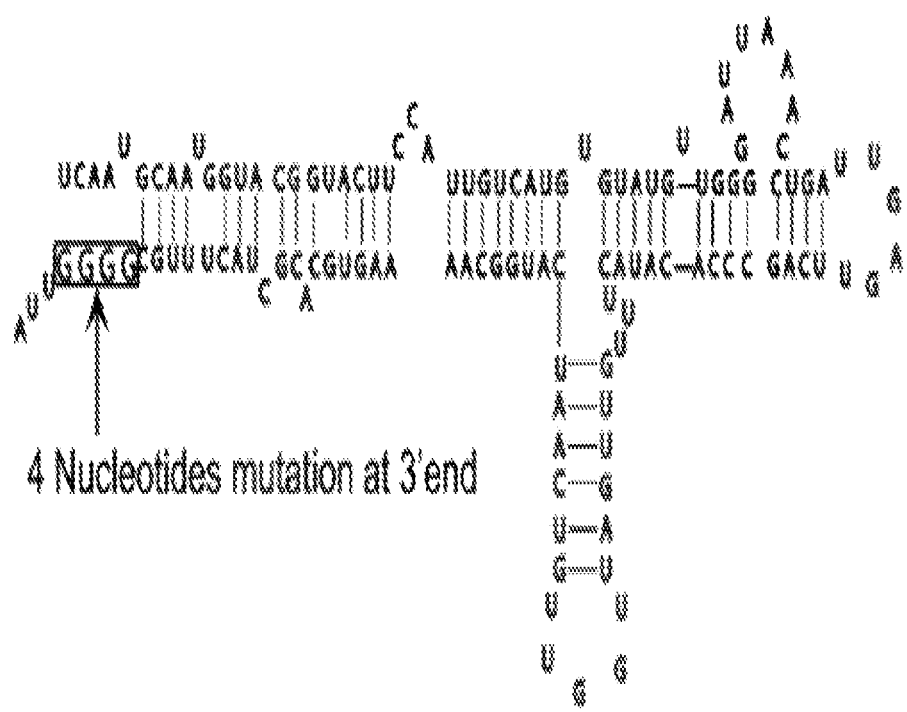
FIGS. 15A-15B shows complete inhibition of viral assembly in vivo by mutant pRNA as a model of drugged complex (Z=6).
Figure 15B:
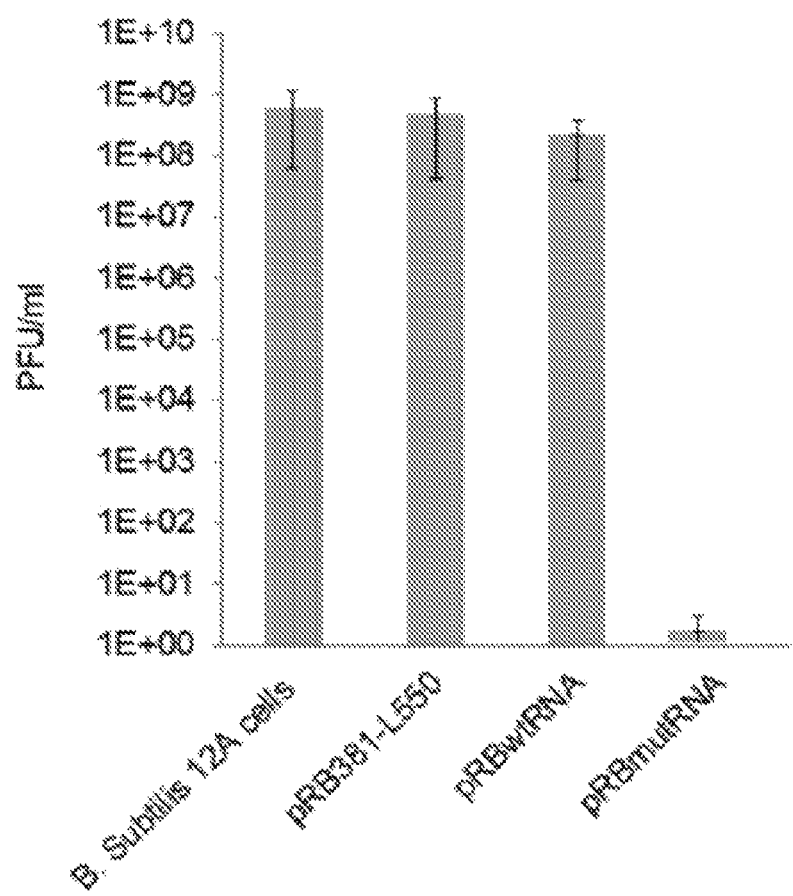

Formation of the hexameric ring of pRNA in the phi29 dsDNA packaging motor has been discovered through biochemical and structural studies and activity assays. The observed high inhibition efficiency by drugged mutant pRNA on phi29 assembly in vitro was striking. To test whether such a high level of inhibition was attainable in vivo, pRBmutRNA plasmid expressing a pRNA with 4-base mutation at the 3' end (FIG. 15A) was transformed into B. subtilis DE1 cells. Plasmid pRBwtRNA contained the pRNA coding sequence but do not express pRNA in B. subtilis DE1 cells, and vector pRB381-L550 was introduced as well as a negative control. The results showed that only cells harboring pRBmutRNA plasmid were completely resistant to plaque formation by wild-type phi29 virus infection. Control cells, including B. subtilis 12A cells alone, B. subtilis DE1 cells carrying vector pRB381-L550 alone, and cells carrying a wild-type pRNA coding sequence but no expression plasmid pRBwtRNA were all positive for plaque fin (nation (FIG. 15B). The ability of mutant pRNAs generated in cells by plasmid pRBmutRNA completely inhibited plaque formation indicated that hexameric pRNA in DNA packaging nano-motor may be a potential target for developing potent antiviral agents.

In Vitro Testing of the Hypothesis Using the ATPase with Stoichiometry of 6

Hexameric folding of ATPase gp16 protein in the phi29 dsDNA packaging motor has been discovered. The hexameric gp16 protein complex functions as ATPase like many other AAA+ superfamily members. ATP binding to one subunit of gp16 stimulates the ATPase to change its conformation from having a lower affinity to one having a higher affinity for dsDNA.

Figure 16A:
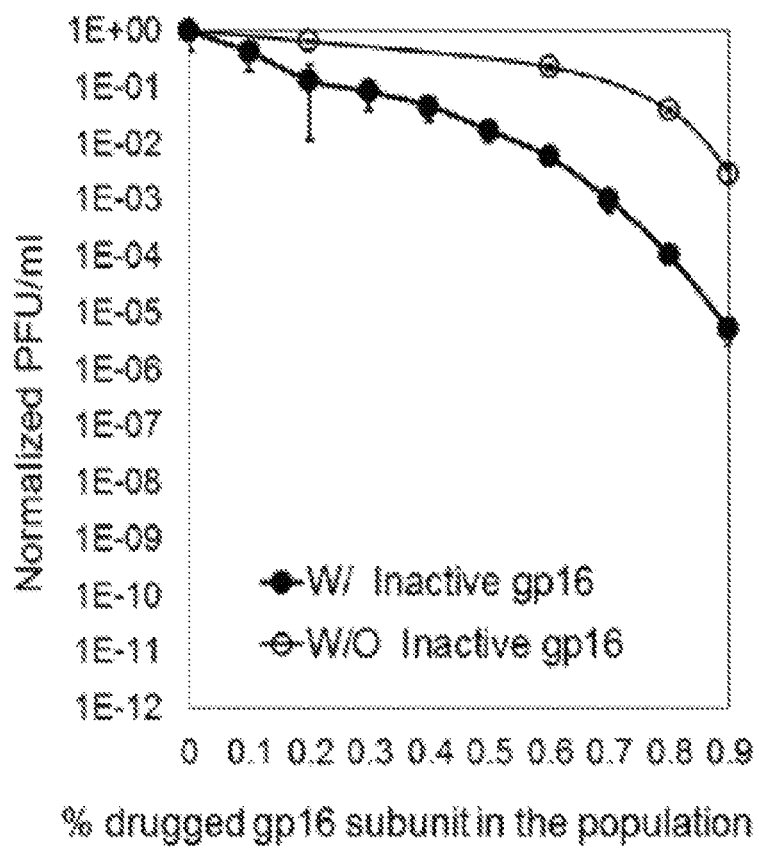
FIGS. 16A-16C show comparison of inhibition efficiency using targets with different Z values.

Determination of gp16 stoichiometry was carried out by in vitro phage assembly assay and based on the binomial distribution of wild-type and Walker B mutant gp16. Different ratios of drugged Walker B mutant gp16 were mixed with undrugged gp16 to test the inhibition efficiency of gp16 mutation on phi29 DNA packaging motor. Assuming K equals 1 and the total copy number of gp16 (Z) is between 1 and 12, twelve theoretical curves for the production of phi29 virion against the ratio of the Walker B mutant corresponding to the stoichiometry (Z) of 1 to 12 were generated according to equation 2. The empirical data nearly perfectly overlapped the theoretical curve of Z=6, K=1. This data suggested that the ATPase gp16 components of phi29 DNA packaging motor have a stoichiometry of six, and only one copy of the drugged gp16 can block the phi29 motor function. Comparing the inhibition effect of adding mutant gp16 with wild-type gp16 at different concentrations, it showed that adding mutant gp16 had a much stronger inhibition effect than the wild-type gp16 concentration dilution control (FIG. 16A). Comparing the inhibition effect of mutation on hexameric gp16 to the effect of mutation on single subunit target DNA, the gp16 mutation displayed a much stronger inhibition effect on virus assembly than the same ratio of DNA mutation, indicating the hexameric ATPase protein complex of virus assembly system should also be an efficient target for generating new anti-virus drugs with high potency.

In Vitro Testing of the Hypothesis Using ATP with Stoichiometry of More than 10000

Figure 16B:
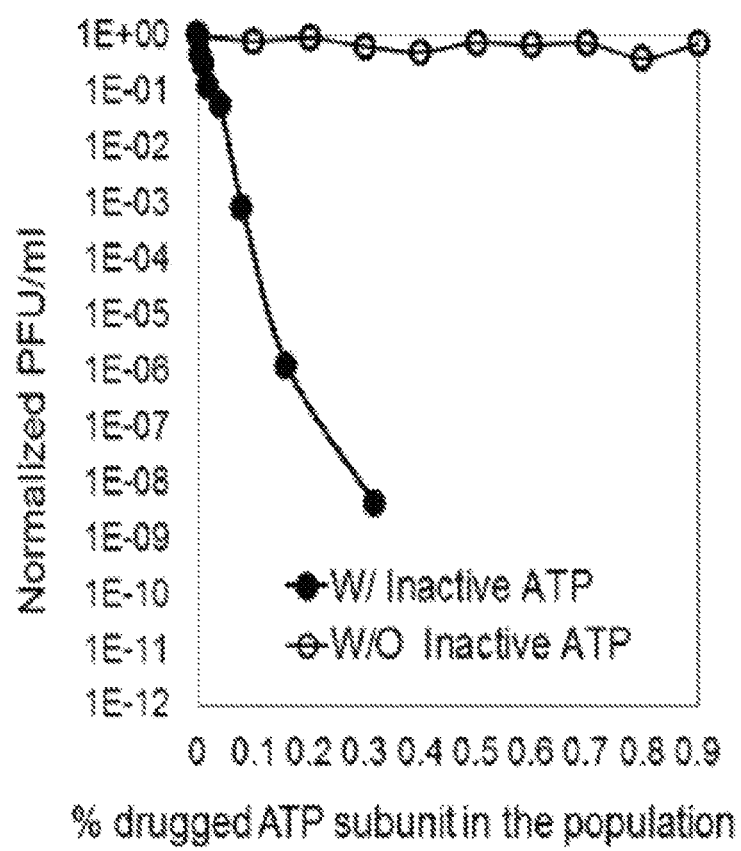

It has been reported that 6 ATP molecules are required to package one pitch of dsDNA with 10.5 bp [90], thus 1 ATP is used to package 1.7 bp. As the entire phi29 genomic DNA has 19,000 base pairs, it is expected that more than 10000 ATP molecules are required to package the entire phi29 genome. Since concerning ATP, the functional unit displayed in FIG. 5 is the viral production expressed as plaque-forming unit (PFU), so the production of one functional unit of PFU require 10000 ATP subunits to package one genomic DNA. Thus, the ATP in one phi29 nanomotor can be regarded as a stoichiometry of 10000. One non-hydrolysable ATP analogue γ-S-ATP was treated as the drugged subunit that mixed with ATP at different ratios to test the inhibition effect of γ-S-ATP on phi29 assembly efficiency. It was found that the inhibition curve of mutant ATP fits into the theoretical curve between Z=100, K=1 and Z=60, K=1 (FIG. 16B). The empirical ATP value derived from binomial distribution assay was different from real condition, since the binomial distribution equation was based on a condition that each subunits has the same binding affinity to the biocomplex in the targeted nanomotor, but due to the change of the γ-S-ATP structure, it has a ATPase gp16 binding affinity lower than the normal ATP. Furthermore, the affinity difference in each subunit has a multiplicative effect in the nanomotor's activity. Thus, there is a big discrepancy between the curves with predicted Z value and the empirical Z value.

Figure 16C:
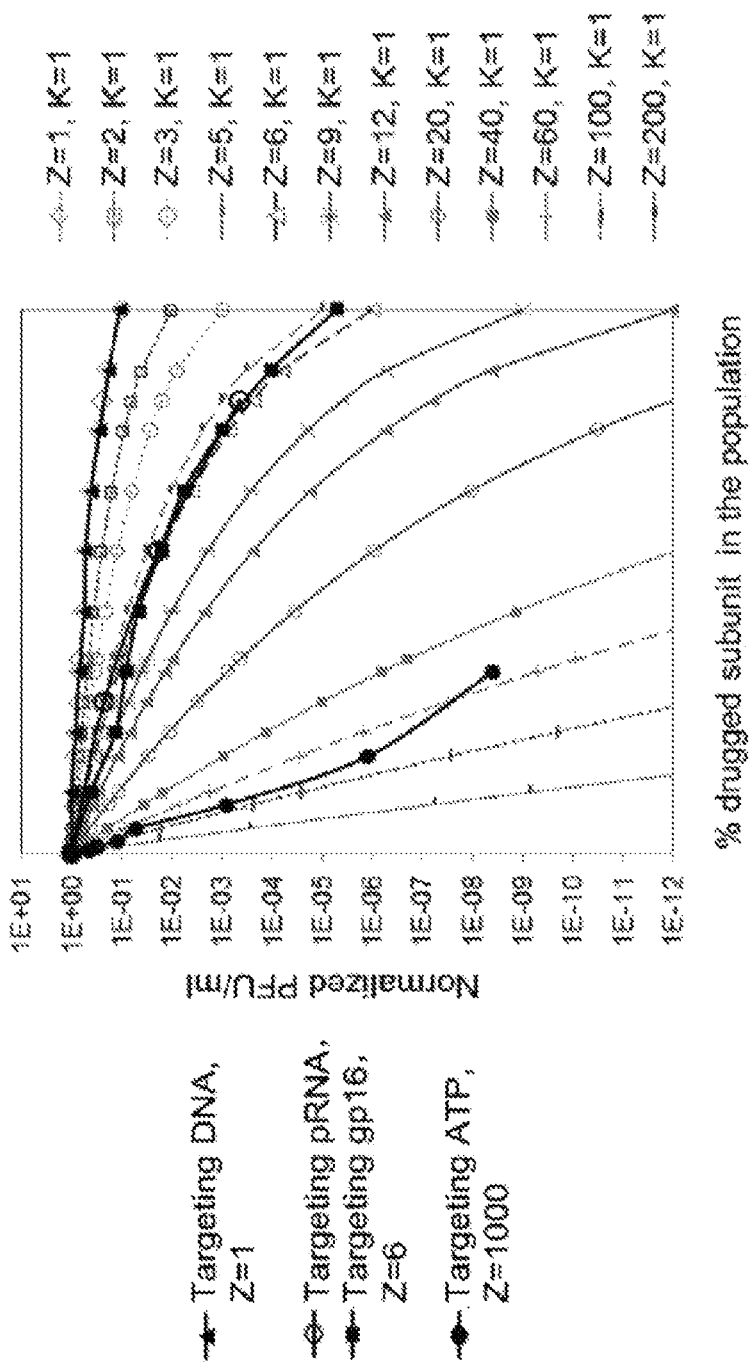

Comparing virus assembly inhibition effect using different components, the γ-S-ATP showed a severe inhibition effect (FIG. 16C). Adding 20% of gamma-s-ATP nearly completely inhibited the viral assembly. Comparing the inhibition effect targeting to ATP, pRNA, ATPase gp16, and DNA with stoichiometry of 10000, 6, 6, and 1, respectively, γ-S-ATP showed the strongest inhibition effect, while drugged mutant pRNA and mutant gp16 showed stronger inhibitory effect than mutant DNA (FIG. 5C). For example, adding 20% mutant DNA caused 20% inhibition effect in viral assembly, while 20% of drugged mutant pRNA exerted 74% of inhibition effect on viral assembly and 20% of γ-S-ATP almost completely inhibited the viral assembly, indicating the higher the stoichiometry, the stronger the inhibition efficacy.

Mathematical Reasoning for the Increase of Inhibition Efficacy

Using a biological complex with higher stoichiometry as drug target will substantially reduce the proportion of non-inhibited complex. For K=1, the proportion of non-inhibited complex is $q^Z$. Table 3 compares the proportion of non-inhibited complex from two populations with Z=6 and Z=1, respectively, with varied substrate targeting efficiency (p) when K=1. For example, when q=0.4, the proportion of non-inhibited complex is $q^Z=0.4^1=0.4$ for Z=1 K=1. Therefore, only 1-0.4=60% of complex is inhibited. In contrast, for Z=6, K=1, the proportion of non-inhibited complex is $q^Z=0.4^6=0.0041$. Therefore, 1-0.0041=99.59% of complex is inhibited. The ratio of the proportions of non-inhibited complex equals 0.0041/0.4=0.0102, indicating a 1/0.0102=98-fold decrease in the proportion of non-inhibited complex. One more example is to use the drug targeting efficiency p=0.9 to compare the inhibition efficiency between two groups with Z=6 and Z=1. For Z=6, K=1, the proportion of inhibited complex is $1-q^Z=1-0.1^6=0.999999$. The proportion of non-inhibited complex is $q^Z=0.1^6=1E-6$. For Z=1, K=1, the proportion of inhibited complex is $1-q^Z=1-0.1=0.9$. The proportion of non-inhibited complex is $q^Z=0.1$. The ratio of inhibition efficiency equals to 1E-6/0.1=1E-5, indicating a 10000-fold increase in inhibition efficiency (Table 3).

The equation displays inhibitory effect with a power function of stoichiometry since when K=1, the percentage of uninhibited biocomplexes in the population equal to $q^Z$. Since (P+q)=1, thus q≤1, thus the larger the Z, the smaller the value of $q^Z$ That is to say, the higher the stoichiometry, the smaller number of the uninhibited background will display. With the same substrate targeting efficacy, p, the inhibition efficiency is determined by z, the power of the equation component. The inhibitory effect is a power function concerning the stoichiometry. Thus, the higher the stoichiometry, the more efficient the inhibition comparing the drugs with same binding affinity.

Figure 17:
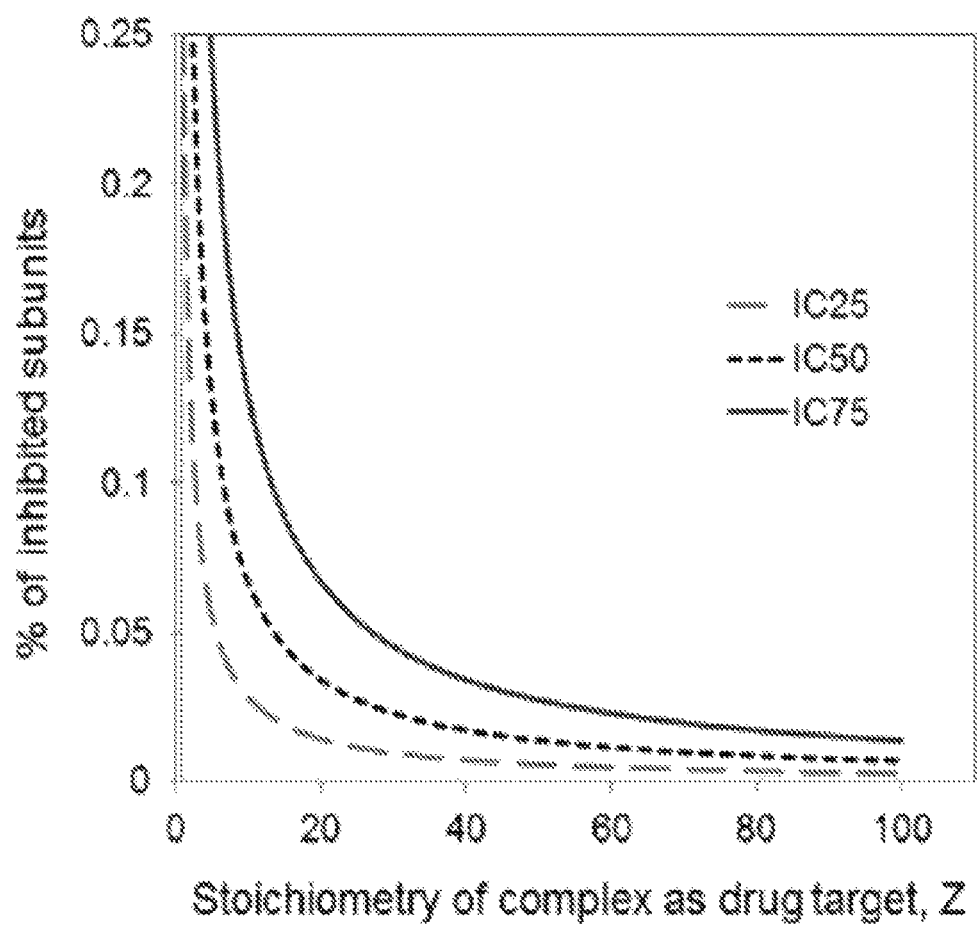
FIG. 17 shows a relationship between stoichiometry (Z) and drug targeting level (a combined result of drug binding efficacy and drug concentration) to reach the inhibition effect (IC).

The half maximal inhibitory concentration ($IC_{50}$) is commonly used to evaluate drug effect, which quantitatively indicates how much of a particular drug is needed to inhibit a given biological process by half. If we denote $p_{IC50}$ as the percentage of drugged subunit needed to reach to 50% inhibition in the in vitro assay in the defined system, thus $1-(1-p_{IC50})^Z=50\%$. Solving this equation, $p_{IC50}=1-0.5^{1/Z}$. FIG. 17 shows the relationship between stoichiometry (Z) and drug targeting level p to reach the inhibition effect (IC), where p is the combined result of drug binding efficacy and drug concentration (dosage). When biocomplexes with stoichiometry of Z are used as drug targets, the dosage of drug or the drug binding affinity presented by percentage of drugged subunits to reach $IC_{50}$, $IC_{25}$, or $IC_{75}$ decreases. This clearly shows that as Z increases, decreases (FIG. 17), and hence the drug is more potent.

Discussion

Aiming to find a method for developing drugs with ultra-high potency, we proposed that the inhibition efficiency of a given drug depends on stoichiometry of the biocomplex or bio-machine that was used as drug target. Here the definition of the stoichiometry is different from conventional definition of stoichiometry used to evaluate drug efficiency. Conventional thinking in drug development emphasizes stoichiometry which refers to the number of drug binding per target molecule, which is also known as $B_{max}$. In this study the definition of stoichiometry refers to the copy number of subunit within a biocomplex that serves as drug target. We used phi29 viral components with a series of variable but known stoichiometry as mock drug targets to test the hypothesis. Both in vitro and in vivo won assembly assays were employed to compare the inhibition efficiency targeting to components with different numbers of subunit stoichiometry. Viral inhibition efficiency was analyzed with Yang Hui's (Pascal's) Triangle (or knowns as binomial distribution). It was found that inhibition efficiency on virus replication correlates to the component stoichiometry of nano-machine as drug target. It displayed power law inhibitory effect since when K=1, the percentage of uninhibited biocomplexes in the population equal to $q^z$. With the same q and same K value, the inhibition efficiency is determined by z, the number of subunits within the biocomplex or the bio-machine as drug target. Here z serves as the power in the equation, thus, the inhibitory effect is the power of the stoichiometry. Empirical data demonstrated that the target with thousand-subunits shows higher inhibition effect than the targets with six subunits, and in turn higher than the target with single subunit.

In evaluation of drug effect, two parameters were commonly used. One is the half maximal inhibitory concentration ($IC_{50}$), which quantitatively indicates how much of a particular drug is needed to inhibit a given biological process by half. It is universally used as a measure of drug potency in pharmacological research. Another important parameter is the median lethal dose ($LD_{50}$), which is also known as 50% of lethal concentration ($LC_{50}$). $LD_{50}$ is frequently used to indicate a substance's acute toxicity. Obviously, the usefulness of a drug will dependent on the ratio of $LD_{50}$ to $IC_{50}$. The larger this ratio, the safer the drug. By ways of increasing the inhibition efficiency through targeting to the components with high stoichiometry, the $IC_{50}$ of a drug will decrease. As a result, lower concentration of drug will be required for reaching a desired effect, resulting in a reduced toxicity of the drug.

Most of current anti-cancer, anti-virus or anti-bacteria drugs target single enzymes or single proteins. Our data showed that drugs selected to target components, biocomplexes, or nano-machines with high copy numbers could lead to a much higher efficacy, and it could potentially solve the problem of low drug effect and multi-drug resistance.

Conclusions

Targeting the functional biological units with higher stoichiometries will have a higher efficiency of inhibition. The inhibition effect is power, other than proportional, and the power, is the copy number of the drug-targeted element of the machine. The new theory developed herein suggests that potent drugs can be developed by targeting biocomplex with high stoichiometry, and a complete inhibition of virus, bacterium, or cancer is possible if a bio-machine with high stoichiometry is identified. Since bio-motors share certain common structure and operation mechanism in viruses, bacteria, and cells, approach should have getter-application in drug development.

Future Perspective

Living systems contain many elegant arrays, motors and nanomachines that are multi-subunit complex. As reported here, these biocomplex with high copy number of components can serve as potent drug targets. For example, most members of the AAA+ family are hexamer. However, these machines are common in living systems therefore the specificity and toxicity is an issue. For bacteria and virus, since our goal is to kill them nonexclusively, the specificity and toxicity is not an issue as long as the target biocomplex is not identical to that in human body. For cancers drugs, as long as a mutation is found in the multiple-subunit biocomplex, it will be an ideal target for potent drug.

Executive Summary

Aim

A method for developing potent drugs is sought.

Without being bound by theory, drug inhibition potency depends on the stoichiometry of the targeted biocomplex.

Approach:

Phi29 viral components with variable stoichiometry were used as model to prove the hypothesis Virion assembly efficiency was assayed and analyzed with Yang Hui's Triangle:

$$(p+q)^Z = \sum_{M=0}^{Z} \binom{Z}{M} p^{Z-M} q^M.$$

Results:

Inhibition efficiency displayed a power function of the stoichiometry of the target biocomplexes. The uninhibited biocomplex in population can equals to $q^z$. Thus, the inhibitory effect is a power of the stoichiometry.

Targets with thousand-subunit showed higher inhibition effect than with six subunits, and in turn higher than target with single subunit.

A complete inhibition of virus, bacterium, or cancer was demonstrated when targets with high stoichiometry was used as target.

Conclusion:

Drug inhibition potency depends on the stoichiometry of the targeted components of the biocomplex or nano-machine.

The inhibition effect displayed a power function of the stoichiometry of the target biocomplex.

Since bio-motors share certain common structure and operation mechanism in viruses, bacteria, and cells, this approach should have general application in drug development.

Finally, for further explanation of the features, benefits and advantages of the present invention, attached hereto is Appendices A-F, which are incorporated herein by this reference in their entirety, as are all cited references in Appendices A-F.

The following two publications (set forth in paragraphs 00295 and 00296 below) are herein incorporated by reference in their entirety.

New approach to develop ultra-high inhibitory drug using the power function of the stoichiometry of the targeted nanomachine or biocomplex. Publication J and date: Nanomedicine (Lond). 2015 July; 10(12):1881-97. doi: 10.2217/nnm.15.37.

Discovery of a new method for potent drug development using power function of stoichiometry of homomeric biocomplexes or biological nanomotors. Publication J and date: Expert Opin Drug Deliv. 2016 January; 13(1):23-36.

All publications, patents, and patent applications mentioned in this specification, including those set forth in the following list, are herein incorporated by reference to the same extent as if each individual publication, patent, or patent application was specifically and individually indicated to be incorporated by reference.

APPENDIX A

Reference Numbers in this Appendix a Correspond to Reference Numbers Set Forth in Section 1 (and FIGS. 1-6)

1. Guo P. Zhao Z, Haak J et al. Common Mechanisms of DNA translocation motors in Bacteria and Viruses Using One-way Revolution Mechanism without Rotation. *Biotechnology Advances* 32, 853-872 (2014).
2. Jankowsky E, Fairman M E, Yang Q. RNA Helicases: Versatile ATP-Driven Nanomotors. *J. Nanosci. Nanotechnol.* 5, 1983-1989 (2005).
3. Guo P X Lee T J. Viral nanomotors for packaging of dsDNA and dsRNA. *Mol. Microbiol.* 64, 886-903 (2007).
4. Molineux L I, Panja D. Popping the cork: mechanisms of phage genome ejection. *Nat Rev. Microbiol.* 11(3), 194-204 (2013).
5. Lee B S, Lee S C, Holliday L S. Biochemistry of mechanoenzymes: Biological motors for nanotechnology. *Biomedical Microdevices* 5(4), 269-280 (2003).
6. Pegtel D M, Cosmopoulos K, Thorley-Lawson D A et al. Functional delivery of viral miRNAs via exosomes. *Proc. Natl. Acad. Sci. U.S.A* 107(14), 6328-6333 (2010).
7. Valadi H, Ekstrom K, Bossios A, Sjostrand M, Lee J J, Lotvall J O. Exosome-mediated transfer of mRNAs and microRNAs is a novel mechanism of genetic exchange between cells. *Nat Cell Biol* 9(6), 654-659 (2007).
8. Wendler F, Bota-Rabassedas N, Franch-Marro X. Cancer becomes wasteful: emerging roles of exosomes (dagger) in cell-fate determination. *J. Extracell. Vesicles.* 2 (22390), 1-9 (2013).
9. Fang H, Jing P, Haque F, Guo P. Role of channel Lysines and "Push Through a One-way Valve" Mechanism of Viral DNA packaging Motor. *Biophysical Journal* 102, 127-135 (2012).
10. Zhang H, Schwartz C, De Donatis G M, Guo P. "Push Through One-Way Valve" Mechanism of Viral DNA Packaging. *Adv. Virus Res* 83, 415-465 (2012).
11. Jing P, Haque F, Shu D, Montemagno C, Guo P. One-Way Traffic of a Viral Motor Channel for Double-Stranded DNA Translocation. *Nano Lett.* 10, 3620-3627 (2010).
12. Kasianowicz J J, Brandin E, Branton D. Deamer D W. Characterization of individual polynucleotide molecules using a membrane channel. *Proc. Natl. Acad. Sci. U.S.A* 93(24), 13770-13773 (1996).
13. Butler T Z, Pavlenok M, Derrington I M, Niederweis M, Gundlach J H. Single-molecule DNA detection with an engineered MspA protein nanopore. *Proc. Natl. Acad. Sci. U.S.A* 105(52), 20647-20652 (2008).
14. Wendell D, Jing P, Geng J et al. Translocation of double-stranded DNA through membrane-adapted phi29 motor protein nanopores. *Nat. Nanotechnol.* 4, 765-772 (2009).
15. Pastoriza-Gallego M, Rabah L, Gibrat G et al. Dynamics of unfolded protein transport through an aerolysin pore. *J. Am. Chem. Soc.* 133(9), 2923-2931 (2011).
16. Ezzell C. How Chaperonins Monitor Their Protein Charges. *The Journal of NIH Research* 6, 31-34 (1994).
17. Maga G, Hubscher U. Proliferating cell nuclear antigen (PCNA): a dancer with many partners. *J. Cell Sci.* 116(Pt 15), 3051-3060 (2003).
18. Rubinchik S, Parris W. Gold M. The in vitro ATPases of bacteriophage terminase and its large subunit, gene product A. *J Biol Chem* 269, 13586-13593 (1994).
19. Schwartz C, De Donatis G M, Fang H, Guo P. The ATPase of the phi29 DNA-packaging motor is a member of the hexameric AAA+ superfamily. *Virology* 443, 20-27 (2013).
20. Sun L, Young L N, Zhang X et al. Icosahedral bacteriophage PhiX174 forms a tail for DNA transport during infection. *Nature* 505(7483), 432-435 (2014).
21. Haque F, Li J, Wu H-C, Liang X-J, Guo P. Solid-state and biological nanopore for real-time sensing of single chemical and sequencing of DNA. *Nano Today* 8, 56-74 (2013).
22. Haque F, Lunn J, Fang H, Smithrud D, Guo P. Real-Time Sensing and Discrimination of Single Chemicals Using the Channel of Phi29 DNA Packaging Nanomotor. *ACS Nano* 6, 3251-3261 (2012).
23. Wang S, Haque F, Rychahou P G, Evers B M, Guo P. Engineered Nanopore of Phi29 DNA-Packaging Motor for Real-Time Detection of Single Colon Cancer Specific Antibody in Serum. *ACS Nano* 7, 9814-9822 (2013).
24. Fennimore A M, Yuzvinsky T D. Han W Q, Fuhrer M S, Cumings J, Zettl A. Rotational actuators based on carbon nanotubes. *Nature* 424, 408-410 (2003).
25. Craighead H G. Nanoelectromechanical systems. *Science* 290, 1532-1536 (2000).
26. Gerion D, Parak W J, Williams S C, Zanchet D, Micheel C M, Alivisatos A P. Sorting fluorescent nanocrystals with DNA. *J Am. Chem Soc.* 124, 7070-7074 (2002).
27. Geng J, Wang S, Fang H, Guo P. Channel size conversion of Phi29 DNA-packaging nanomotor for discrimination of single- and double-stranded nucleic acids. *ACS Nano* 7(4), 3315-3323 (2013).
28. McNally B, Singer A, Yu Z. Sun Y, Weng Z. Meller A. Optical recognition of converted DNA nucleotides for single-molecule DNA sequencing using nanopore arrays. *Nano Lett.* 10(6), 2237-2244 (2010).
29. Chandler E L, Smith A L, Burden L M. Kasianowicz J J, Burden D L. Membrane surface dynamics of DNA-threaded nanopores revealed by simultaneous single-molecule optical and ensemble electrical recording. *Langmuir* 20(3), 898-905 (2004).
30. Shu D, Shu Y, Haque F, Abdelmawla S, Guo P. Thermodynamically stable RNA three-way junctions for constructing multifunctional nanoparticles for delivery of therapeutics. *Nature Nanotechnology* 6, 658-667 (2011).
31. Haque F, Shu D, Shu Y et al. Ultrastable synergistic tetravalent RNA nanoparticles for targeting to cancers. *Nano Today* 7, 245-257 (2012).
32. Crozat E, Grainge I. FtsK DNA translocase: the fast motor that knows where it's going. *Chembiochem.* 11, 2232-2243 (2010).
33. Schwartz C, De Donatis G M, Zhang F L Fang H, Guo P. Revolution rather than rotation of AAA+ hexameric phi29 nanomotor for viral dsDNA packaging without coiling. *Virology* 443, 28-39 (2013).
34. Hanson P I, Whiteheart S W. AAA+ proteins: have engine, will work. *Nat. Rev. Mol Cell Biol.* 6, 519-529 (2005).
35. Guo P, Schwartz C, Haak J, Zhao Z. Discovery of a new motion mechanism of biomotors similar to the earth revolving around the sun without rotation. *Virology* 446, 133-143 (2013).
36. De-Donatis G, Zhao Z, Wang S et al. Finding of widespread viral and bacterial revolution dsDNA translocation motors distinct from rotation motors by channel chirality and size. *Cell Biosci* 4, 30-(2014).
37. Batra S, Adekola K U A, Rosen S T, Shanmugam M. Cancer Metabolism as a Therapeutic Target. *ONCOLOGY-NEW YORK* 27, 460-467 (2013).
38. Buskin S E, Zhang S, Thibault C S. Prevalence of and viral outcomes associated with primary HIV-1 drug resistance. *Open. AIDS J.* 6, 181-187 (2012).
39. Spellberg B. Powers J H, Brass E P, Miller L G, Edwards J E. Jr. Trends in antimicrobial drug development: implications for the future. *Clin. Infect. Dis.* 38(9), 1279-1286 (2004).
40. Lakshmanan M, Xavier A S. Bedaquiline—The first ATP synthase inhibitor against multi drug resistant tuberculosis. *J. Young. Pharm.* 5(4), 112-115 (2013).
41. Aird K M, Ding X Y, Baras A et al. Trastuzumab signaling in ErbB2-overexpressing inflammatory breast cancer correlates with X-linked inhibitor of apoptosis protein expression. *Molecular Cancer Therapeutics* 7(1), 38-47 (2008).
42. Park S H, Kim H. Song B J. Down regulation of bcl2 expression in invasive ductal carcinomas is both estrogen- and progesterone-receptor dependent and associated with poor prognostic factors. *Pathol. Oncol. Res.* 8(1), 26-30 (2002).
43. Akine A, Querbes W, De S et al. Targeted delivery of RNAi therapeutics with endogenous and exogenous ligand-based mechanisms. *Mol. Ther.* 18(7), 1357-1364 (2010).
44. Aronov O, Horowitz A T, Gabizon A. Gibson D. Folate-targeted PEG as a potential carrier for carboplatin analogs. Synthesis and in vitro studies. *Bioconjugate Chem.* 14(3), 563-574 (2003).
45. Bae Y H, Park K. Targeted drug delivery to tumors: myths, reality and possibility. *J. Control Release* 153(3), 198-205 (2011).
46. Guo P, Haque F, Hallahan B. Reif R, Li H. Uniqueness, advantages, challenges, solutions, and perspectives in therapeutics applying RNA nanotechnology. *Nucleic Acid Ther.* 22(4), 226-245 (2012).
47. Lusky K. HIV's potent cocktail. *Contemp. Longterm. Care* 22(12), 59-(1999).
48. Chatterjee A, Chattopadhyay D, Chakrabarti G. miR-17-5p Downregulation Contributes to Paclitaxel Resistance of Lung Cancer Cells through Altering Beclin1 Expression. *PLoS ONE* 9(4), e95716-(2014).
49. Sanchez C, Chan R, Bajgain P et al. Combining T-cell immunotherapy and anti-androgen therapy for prostate cancer. *Prostate Cancer Prostatic. Dis.* 16(2), 123-31 (2013).
50. Ito M, Zhao N, Zeng Z, Chang C C, Zu Y. Synergistic growth inhibition of anaplastic large cell lymphoma cells by combining cellular ALK gene silencing and a low dose of the kinase inhibitor U0126. *Cancer Gene Ther.* 17(9), 633-44 (2010).
51. Fang H, Zhang P, Huang L P et al. Binomial distribution for quantification of protein subunits in biological nano-assemblies and functional nanomachines. *Nanomedicine.* 10(7), 1433-40 (2014).
52. Guo P, Zhang C, Chen C, Trottier M, Garver K. Inter-RNA interaction of phage phi29 pRNA to form a hexameric complex for viral DNA transportation. *Mol. Cell.* 2, 149-155 (1998).
53. Hugel T, Michaelis J, Hetherington C L et al. Experimental test of connector rotation during DNA packaging into bacteriophage phi29 capsids. *Plos Biology* 5, 558-567 (2007).
54. Xiao F, Moll D, Guo S, Guo P. Binding of pRNA to the N-terminal 14 amino acids of connector protein of bacterial phage phi29. *Nucleic Acids Res* 33, 2640-2649 (2005).
55. Guo P, Peterson C, Anderson D. Prohead and DNA-gp3-dependent ATPase activity of the DNA packaging protein gp16 of bacteriophage phi29. *J Mol Biol* 197, 229-236 (1987).
56. Trottier M Guo P. Approaches to determine stoichiometry of viral assembly components. *J. Virol.* 71, 487-494 (1997).
57. Guo P, Peterson C, Anderson D. Initiation events in in vitro packaging of bacteriophage phi29 DNA-gp3. *J Mol Biol* 197, 219-228 (1987).
58. Zhao Z, Khisamutdinov E, Schwartz C, Guo P. Mechanism of one-way traffic of hexameric phi29 DNA packaging motor with four electropositive relaying layers facilitating anti-parallel revolution. *ACS Nano* 7, 4082-4092 (2013).
59. Guo P, Grainge I, Zhao Z, Vieweger M. Two classes of nucleic acid translocation motors: rotation and revolution without rotation. *Cell Biosci.* 4(1), 54-(2014).
60. Casjens S R. The DNA-packaging nanomotor of tailed bacteriophages. *Nat Rev. Microbiol.* 9(9), 647-657 (2011).
61. Boal A K, Ilhan F, DeRouchey J E, Thum-Albrecht T, Russell T P, Rotello V M. Self-assembly of nanoparticles into structured spherical and network aggregates. *Nature* 404(6779), 746-748 (2000).
62. Holohan C. Van S S, Longley D B, Johnston P G. Cancer drug resistance: an evolving paradigm. *Nat. Rev. Cancer* 13(10), 714-726 (2013).
63. Guo P, Grimes S, Anderson D. A defined system for in vitro packaging of DNA-gp3 of the *Bacillus subtilis* bacteriophage phi29. *Proc. Natl. Acad. Sci. USA* 83, 3505-3509 (1986).
64. Zhang C L, Lee C-S, Guo P. The proximate 5' and 3' ends of the 120-base viral RNA (pRNA) are crucial for the packaging of bacteriophage φ29 DNA. *Virology* 201, 77-85 (1994).
65. Shu D, Huang L, Hoeprich S. Guo P. Construction of phi29 DNA-packaging RNA (pRNA) monomers, dimers and trimers with variable sizes and shapes as potential parts for nano-devices. *J. Nanosci. Nanotechnol.* 3, 295-302 (2003).
66. Lee C S, Guo P. A highly sensitive system for the assay of in vitro viral assembly of bacteriophage phi29 of *Bacillus subtilis*. *Virology* 202, 1039-1042 (1994).
67. Trottier M, Zhang C L, Guo P. Complete inhibition of virion assembly in vivo with mutant pRNA essential for phage phi29 DNA packaging. *J. Virol.* 70, 55-61 (1996).
68. Chen C Guo P. Sequential action of six virus-encoded DNA-packaging RNAs during phage phi29 genomic DNA translocation. *J. Viral.* 71(5), 3864-3871 (1997).
69. Stitt B L, Xu Y. Sequential hydrolysis of ATP molecules bound in interacting catalytic sites of *Escherichia coli* transcription termination protein Rho. *J. Biol. Chem* 273 (41), 26477-26486 (1998).
70. Kammerer R A, Schulthess T, Landwehr R, Lustig A, Fischer D, Engel J. Tenascin-C hexabrachion assembly is a sequential two-step process initiated by coiled-coil alpha-helices. *J. Biol. Chem.* 273(17), 10602-10608 (1998).
71. Lisal J, Tuma R. Cooperative mechanism of RNA packaging motor. *J Biol Chem* 280, 23157-23164 (2005).
72. Zhang Z, Lewis D, Strock C et al. Detailed characterization of the cooperative mechanism of Ca(2+) binding and catalytic activation in the Ca(2+) transport (SERCA) ATPase. *Biochemistry* 39(30), 8758-8767 (2000).
73. Sun H, Squier T C. Ordered and cooperative binding of opposing globular domains of calmodulin to the plasma membrane Ca-ATPase. *J. Biol. Chem.* 275(3), 1731-1738 (2000).
74. Hiller R, Carmeli C. Kinetic analysis of cooperative interactions induced by Mn2+ binding to the chloroplast H(+)-ATPase. *Biochemistry* 29(26), 6186-6192 (1990).
75. Persechini A, Hartshorne D J. Cooperative behavior of smooth muscle myosin. *Fed. Proc.* 41(12), 2868-2872 (1982).
76. Lee C S, Guo P. Sequential interactions of structural proteins in phage phi29 procapsid assembly. *J. Virol.* 69, 5024-5032 (1995).
77. Casjens S, Hendrix R. Control mechanisms in dsDNA bacteriophage assembly. In: *The Bacteriophages Vol.* 1. Calendar R (Eds.). Plenum Publishing Corp., 15-92 (1988)
78. Qian X, Ren Y, Shi Z et al. Sequence-dependent synergistic inhibition of human glioma cell lines by combined temozolomide and miR-21 inhibitor gene therapy. *Mol. Pharm.* 9(9), 2636-2645 (2012).
79. Zhang H, Shu D, Huang F, Guo P. Instrumentation and metrology for single RNA counting in biological complexes or nanoparticles by a single molecule dual-view system. *RNA* 13, 1793-1802 (2007).
80. Chen C, Trottier M, Guo P. New approaches to stoichiometry determination and mechanism investigation on RNA involved in intermediate reactions. *Nucleic Acids Symposium Series* 36, 190-193 (1997).
81. Shu D. Zhang H, Jin J, Guo P. Counting of six pRNAs of phi29 DNA-packaging motor with customized single molecule dual-view system. *EMBO J.* 26, 527-537 (2007).
82. Shu Y, Haque F, Shu D et al. Fabrication of 14 Different RNA Nanoparticles for Specific Tumor Targeting without Accumulation in Normal Organs. *RNA* 19, 766-777 (2013).
83. Shu Y, Shu D, Haque F, Guo P. Fabrication of pRNA nanoparticles to deliver therapeutic RNAs and bioactive compounds into tumor cells. *Nat Protoc.* 8(9), 1635-1659 (2013).
84. Zhang H, Endrizzi J A, Shu Y et al. Crystal Structure of 3WJ Core Revealing Divalent Ion-promoted Thermostability and Assembly of the Phi29 Hexameric Motor pRNA. *RNA* 19, 1226-1237 (2013).
85. Mueller-Cajar O, Stotz M, Wendler P, Hartl F U, Bracher A, Hayer-Hartl M. Structure and function of the AAA+ protein CbbX, a red-type Rubisco activase. *Nature* 479, 194-199 (2011).
86. Wang F, Mei Z, Qi Y et al. Structure and mechanism of the hexameric MecA-ClpC molecular machine. *Nature* 471, 331-335 (2011).
87. Aker J, Hesselink R, Engel R et al. In vivo hexamerization and characterization of the *Arabidopsis* AAA ATPase CDC48A complex using forster resonance energy transfer-fluorescence lifetime imaging microscopy and fluorescence correlation spectroscopy. *Plant Physiology* 145(2), 339-350 (2007).
88. Willows R D. Hansson A, Birch D, Al-Karadaghi S, Hansson M. EM single particle analysis of the ATP-dependent BchI complex of magnesium chelatase: an AAA(+) hexamer. *J Struct Biol* 146(1-2), 227-233 (2004).
89. Chen Y J, Yu X, Egelman E H. The hexameric ring structure of the *Escherichia coli* RuvB branch migration protein. *J. Mol. Biol.* 319(3), 587-591 (2002).
90. Happonen L J, Oksanen E, Liljeroos L, Goldman A. Kajander T, Butcher S J. The structure of the NTPase that powers DNA packaging into *Sulfolobus* turreted icosahedral virus 2. *J. Virol.* 87, 8388-8398 (2013).
91. Snider J, Thibault G, Houry W A. The AAA+ superfamily of functionally diverse proteins. *Genome Biol* 9(4), 216-216 (2008).
92. Schwartz C, Fang H, Huang L, Guo P. Sequential action of ATPase, ATP, ADP, Pi and dsDNA in procapsid-free system to enlighten mechanism in viral dsDNA packaging. *Nucleic Acids Res.* 40, 2577-2586 (2012).
93. Trottier M, Garver K, Zhang C, Guo P. DNA-packaging pRNA as target for complete inhibition of viral assembly in vitro and in vivo. *Nucleic Acids Symposium Series* 36, 187-189 (1997).
94. Chen C, Zhang C, Guo P. Sequence requirement for hand-hi-hand interaction in formation of pRNA dimers and hexamers to gear phi29 DNA translocation motor. *RNA* 5, 805-818 (1999).
95. Zhang C L, Trottier M, Guo P X. Circularly permuted viral pRNA active and specific in the packaging of bacteriophage Phi29 DNA. *Virology* 207, 442-451 (1995).
96. Zhang F, Lemieux S, Wu X et al. Function of hexameric RNA in packaging of bacteriophage phi29 DNA in vitro. *Mol. Cell.* 2, 141-147 (1998).
97. Hendrix R W. Bacteriophage DNA packaging: RNA gears in a DNA transport machine (Minireview). *Cell* 94, 147-150 (1998).
98. Bourassa N, Major F. Implication of the prohead RNA in phage phi29 DNA packaging. *Biochimie* 84, 945-951 (2002).
99. Xiao F, Zhang H. Guo P. Novel mechanism of hexamer ring assembly in protein/RNA interactions revealed by single molecule imaging. *Nucleic Acids Res* 36, 6620-6632 (2008).
100. Moll D Guo P. Grouping of Ferritin and Gold Nanoparticles Conjugated to pRNA of the Phage phi29 DNA-packaging motor. *J Nanosci and Nanotech (JNN)* 7, 3257-3267 (2007).
101. Ibarra B, Caston J. R., Llorca O., Valle M, Valpuesta J. M., Carrascosa J. L. Topology of the components of the DNA packaging machinery in the phage phi29 prohead. *J. Mol. Biol.* 298, 807-815 (2000).
102. Xiao F, Demeler B, Guo P. Assembly Mechanism of the Sixty-Subunit Nanoparticles via Interaction of RNA with the Reengineered Protein Connector of phi29 DNA-Packaging Motor. *ACS Nano.* 4(6), 3293-3301 (2010).
103. Fang Y, Cai Q, Qin P Z. The procapsid binding domain of phi29 packaging RNA has a modular architecture and requires 2'-hydroxyl groups in packaging RNA interaction. *Biochemistry* 44, 9348-9358 (2005).
104. Chen C, Sheng S, Shao Z, Guo P. A dimer as a building block in assembling RNA: A hexamer that gears bacterial virus phi29 DNA-translocating machinery. *J Biol Chem* 275(23), 17510-17516 (2000).
105. Zhang C L, Garver K, Guo P. Inhibition of phage phi29 assembly by antisense oligonucleotides targeting viral pRNA essential for DNA packaging. *Virology* 211, 568-576 (1995).
106. White S R, Lauring B. AAA+ ATPases: Achieving diversity of function with conserved machinery. *Traffic* 8(12), 1657-1667 (2007).
107. Iyer L M, Leipe D D, Koonin E V, Aravind L. Evolutionary history and higher order classification of AAA plus ATPases. *J Struct Biol* 146(1-2), 11-31 (2004).

108. Liu Y, Huang T, MacMorris M, Blumenthal T. Interplay between AAUAAA and the trans-splice site in processing of a *Caenorhabditis elegans* operon pre-mRNA. *RNA*. 7(2), 176-181 (2001).

APPENDIX B

Tables in this Appendix Correspond to the Tables Set Forth in Section 1

TABLE 1

Probability of the complex containing M copies of drugged subunits and N copies of undrugged subunits

| Inhibited Subunits (p) | Z = 3 | | | |
|---|---|---|---|---|
| | M = 0, N = 3 | M = 1, N = 2 | M = 2, N = 1 | M = 3, N = 0 |
| 0   | 1.0000 | 0.0000 | 0.0000 | 0.0000 |
| 0.1 | 0.7290 | 0.2430 | 0.0270 | 0.0010 |
| 0.2 | 0.5120 | 0.3840 | 0.0960 | 0.0080 |
| 0.3 | 0.3430 | 0.4410 | 0.1890 | 0.0270 |
| 0.4 | 0.2160 | 0.4320 | 0.2880 | 0.0640 |
| 0.5 | 0.1250 | 0.3750 | 0.3750 | 0.1250 |
| 0.6 | 0.0640 | 0.2880 | 0.4320 | 0.2160 |
| 0.7 | 0.0270 | 0.1890 | 0.4410 | 0.3430 |
| 0.8 | 0.0080 | 0.0960 | 0.3840 | 0.5120 |
| 0.9 | 0.0010 | 0.0270 | 0.2430 | 0.7290 |
| 1   | 0.0000 | 0.0000 | 0.0000 | 1.0000 |

| Inhibited Subunits (p) | Z = 12 | | | | | | | | | | | | |
|---|---|---|---|---|---|---|---|---|---|---|---|---|---|
| | M = 0, N = 12 | M = 1, N = 11 | M = 2, N = 10 | M = 3, N = 9 | M = 4, N = 8 | M = 5, N = 7 | M = 6, N = 6 | M = 7, N = 5 | M = 8, N = 4 | M = 9, N = 3 | M = 10, N = 2 | M = 11, N = 1 | M = 12, N = 0 |
| 0   | 1.0000 | 0.0000 | 0.0000 | 0.0000 | 0.0000 | 0.0000 | 0.0000 | 0.0000 | 0.0000 | 0.0000 | 0.0000 | 0.0000 | 0.0000 |
| 0.1 | 0.2824 | 0.3766 | 0.2301 | 0.0852 | 0.0213 | 0.0038 | 0.0005 | 0.0000 | 0.0000 | 0.0000 | 0.0000 | 0.0000 | 0.0000 |
| 0.2 | 0.0687 | 0.2062 | 0.2835 | 0.2362 | 0.1329 | 0.0532 | 0.0155 | 0.0033 | 0.0005 | 0.0001 | 0.0000 | 0.0000 | 0.0000 |
| 0.3 | 0.0138 | 0.0712 | 0.1678 | 0.2397 | 0.2311 | 0.1585 | 0.0792 | 0.0291 | 0.0078 | 0.0015 | 0.0002 | 0.0000 | 0.0000 |
| 0.4 | 0.0022 | 0.0174 | 0.0639 | 0.1419 | 0.2128 | 0.2270 | 0.1766 | 0.1009 | 0.0420 | 0.0125 | 0.0025 | 0.0003 | 0.0000 |
| 0.5 | 0.0002 | 0.0029 | 0.0161 | 0.0537 | 0.1208 | 0.1934 | 0.2256 | 0.1934 | 0.1208 | 0.0537 | 0.0161 | 0.0029 | 0.0002 |
| 0.6 | 0.0000 | 0.0003 | 0.0025 | 0.0125 | 0.0420 | 0.1009 | 0.1766 | 0.2270 | 0.2128 | 0.1419 | 0.0639 | 0.0174 | 0.0022 |
| 0.7 | 0.0000 | 0.0000 | 0.0002 | 0.0015 | 0.0078 | 0.0291 | 0.0792 | 0.1585 | 0.2311 | 0.2397 | 0.1678 | 0.0712 | 0.0138 |
| 0.8 | 0.0000 | 0.0000 | 0.0000 | 0.0001 | 0.0005 | 0.0033 | 0.0155 | 0.0532 | 0.1329 | 0.2362 | 0.2835 | 0.2062 | 0.0687 |
| 0.9 | 0.0000 | 0.0000 | 0.0000 | 0.0000 | 0.0000 | 0.0000 | 0.0005 | 0.0038 | 0.0213 | 0.0852 | 0.2301 | 0.3766 | 0.2824 |
| 1   | 0.0000 | 0.0000 | 0.0000 | 0.0000 | 0.0000 | 0.0000 | 0.0000 | 0.0000 | 0.0000 | 0.0000 | 0.0000 | 0.0000 | 1.0000 |

TABLE 2

Predicted inhibition efficiency of drugs targeting biocomplexes, K = 1

| Drugged subunit (p) | Inhibition efficiency of the multi-subunit complex with | | | | | | |
|---|---|---|---|---|---|---|---|
| | Z = 1 | Z = 2 | Z = 3 | Z = 6 | Z = 10 | Z = 100 | Z = 1000 |
| 0   | 0.0000 | 0.0000 | 0.0000 | 0.0000 | 0.0000 | 0.0000 | 0.0000 |
| 0.1 | 0.1000 | 0.1900 | 0.2710 | 0.4686 | 0.6513 | 1.0000 | 1.0000 |
| 0.2 | 0.2000 | 0.3600 | 0.4880 | 0.7379 | 0.8926 | 1.0000 | 1.0000 |
| 0.3 | 0.3000 | 0.5100 | 0.6570 | 0.8824 | 0.9718 | 1.0000 | 1.0000 |
| 0.4 | 0.4000 | 0.6400 | 0.7840 | 0.9533 | 0.9940 | 1.0000 | 1.0000 |
| 0.5 | 0.5000 | 0.7500 | 0.8750 | 0.9844 | 0.9990 | 1.0000 | 1.0000 |
| 0.6 | 0.6000 | 0.8400 | 0.9360 | 0.9959 | 0.9999 | 1.0000 | 1.0000 |
| 0.7 | 0.7000 | 0.9100 | 0.9730 | 0.9993 | 1.0000 | 1.0000 | 1.0000 |
| 0.8 | 0.8000 | 0.9600 | 0.9920 | 0.9999 | 1.0000 | 1.0000 | 1.0000 |
| 0.9 | 0.9000 | 0.9900 | 0.9990 | 1.0000 | 1.0000 | 1.0000 | 1.0000 |
| 1   | 1.0000 | 1.0000 | 1.0000 | 1.0000 | 1.0000 | 1.0000 | 1.0000 |

TABLE 3

Comparison of proportion of non-inhibited complex between Z = 6 and
Z = 1 when K = 1 but having equal drug targeting efficacy

| Substrate targeting efficacy (p) | Proportion of non-inhibited complex from the population with Z = 6 | Proportion of non-inhibited complex from the population with Z = 1 | Ratio of the proportions of non-inhibited complex from the two populations with Z = 6 and Z = 1 | Reduction (fold) in proportion of non-inhibited complex comparing Z = 6 and Z = 1 |
|---|---|---|---|---|
| 0 | 1 | 1 | 1 | 1 |
| 0.1 | 0.5314 | 0.9 | 0.5905 | 1.7 |
| 0.2 | 0.2621 | 0.8 | 0.3277 | 3.1 |
| 0.3 | 0.1176 | 0.7 | 0.1681 | 5.9 |
| 0.4 | 0.0467 | 0.6 | 0.0778 | 12.9 |
| 0.5 | 0.0156 | 0.5 | 0.0312 | 32 |
| 0.6 | 0.0041 | 0.4 | 0.0102 | 98 |
| 0.7 | 7E−04 | 0.3 | 0.0024 | 416 |
| 0.8 | 1E−04 | 0.2 | 0.0003 | 3333 |
| 0.9 | 1E−06 | 0.1 | 1E−05 | 10000 |

APPENDIX C

This Appendix Provides Synopses for Certain References Set Forth in Appendix A

1**. Guo P, Zhao Z, Haak J, Wang S, Weitao T. Common Mechanisms of DNA translocation motors in Bacteria and Viruses Using One-way Revolution Mechanism without Rotation. *Biotechnology Advances*. 32, 853-872 (2014).
Synopsis: This review reports that revolution mechanism is commonly used in bacteria and viruses which avoid DNA g in translocation the lengthy genomic dsDNA helix.

19*. Schwartz C, Dc Donatis G M, F ng H, Guo P. The ATPase of the phi29 DNA-packaging motor is a member of the hexameric AAA+ superfamily. *Virology* 443, 20-27 (2013).
Synopsis: This paper confirmed the stoichiometry of ATPase in phi29 motor is a hexamer and provided data suggesting that the phi29 motor ATPase belongs to classical hexameric AAA+ superfamily.

33*. Schwartz C, Donatis G M, Zhang H, Fang H, Guo P. Revolution rather than rotation of AAA+ hexameric phi29 nanomotor for dsDNA packaging without coiling. *Virology* 443, 28-39 (2013).
Synopsis: This paper shows how the nanomotor in phi29 virus w with a revolution mechanism using six copies of ATPase.

36**. De-Donatis G, Zhao Z, Wang S et al. Finding of widespread viral and bacterial revolution dsDNA translocation motors distinct from rotation motors by channel chirality and size. Cell & Bioscience 4, 30 (2014).
Synopsis: This paper reports that the revolution motor nanomachine is widespread among biological systems, an can be distinguished from rotation motors by channel size and chirality.

51**. Fang H, Huang L P et al. Binomial distribution for quantification of protein subunits in biological nanoassemblies and functional nanomachines. *Nanomedicine*. 10(7), 1433-40 (2014).
Synopsis: This is the first report to describe how to use the Yang Hui's Triangle (binomial distribution) to determine the stoichiometry of protein subunits in biocomplex. It precisely confirmed that phi29 motor contains six copies of ATPase gp16 and one mutant subunit would cause motor to stop.

52*. Gun P. Zhang C, Chen C, Trottier M. Garver K. Inter-1 interaction of phage phi29 pRNA to form a hexameric complex for viral DNA transportation. *Mol. Cell*. 2, 149-15, (1998
Synopsis: This is the first paper to reveal that the pRNA of phi29 DNA packaging motorfirms a hexameric ring, and prove-of-concept of RNA nanotechnology since this paper shows that by bottom-up assembly, the RNA nanoparticles of dimers, trimers and hexamers can be constructed using the reenginered RNA fragments derived from phi29 motor pRNA.

*56. Trottier M, Quo P. Approaches to determine stoichiometry of viral assembly components. *J. Virol*. 71, 487-494 (1997),
Synopsis: This is the first report to describe how to use the Yang Hui Triangle (binomial distribution) to determine the stoichiometry of biocomplex or nanomachine.

81*. Shu D, Zhang H, Guo P. Counting of six pRNAs of phi29 DNA-packaging motor with customized single molecule dual-view system. *EMBO J*. 26, 527-537 (2007).
Synopsis: This is the first report describing the use of single fluorophore photobleaching technique to count subunits in biocomplex, and documents the "seeing is believing" to confirm that phi29 DNA packaging motor contains six copies of packaging pRNA.

APPENDIX D

Reference Numbers in this Appendix D Correspond to Reference Numbers Set Forth in Section 2 (and FIGS. 7-11)

1. Batra S, Adekola K U A, Rosen S T, Shanmugam M. Cancer Metabolism as a Therapeutic Target. ONCOLOGY-NEW YORK 2013; 27:460-7

2. Aird K M, Ding X Y, Batas A, et al. Trastuzumab signaling in ErbB2-overexpressing inflammatory breast cancer correlates with X-linked inhibitor of apoptosis protein expression. Molecular Cancer Therapeutics 2008; 7:38-47

3. Park S H, Kim H, Song B J. Down regulation of bcl2 expression in invasive ductal carcinomas is both estrogen- and progesterone-receptor dependent and associated with poor prognostic factors. Pathol Oncol Res 2002; 8:26-30

4. Lakshmanan M, Xavier A S. Bedaquiline—The first ATP synthase inhibitor against multi drug resistant tuberculosis. J Young Pharm 2013; 5:112-5
5. Akinc A, Querbes W, De S, et al. Targeted delivery of RNAi therapeutics with endogenous and exogenous ligand-based mechanisms. Mol Ther 2010; 18:1357-64
6. Aronov O, Horowitz A T, Gabizon A, Gibson D. Folate-targeted PEG as a potential carrier for carboplatin analogs. Synthesis and in vitro studies. Bioconjugate Chem 2003; 14:563-74
7. Bae Y H, Park K. Targeted drug delivery to tumors: myths, reality and possibility. J Control Release 2011; 153:198-205
8. Guo P. Haque E. Hallahan B. et al. Uniqueness, advantages, challenges, solutions, and perspectives in therapeutics applying RNA nanotechnology. Nucleic Acid Ther 2012; 22:226-45
9. Chatterjec A, Chattopadhyay D, Chakrabarti G. miR-17-5p Downregulation Contributes to Paclitaxel Resistance of Lung Cancer Cells through Altering Beclin1 Expression. PLoS ONE 2014; 9:e95716
10. Sanchez C, Chan R, Bajgain P, et al. Combining T-cell immunotherapy and anti-androgen therapy for prostate cancer. Prostate Cancer Prostatic Dis 2013; 16:123-131.
11. Lusky K. HIV's potent cocktail. Contemp Longterm Care 1999; 22:59
12. Ito M. Zhao N, Zeng Z, et al. Synergistic growth inhibition of anaplastic large cell lymphoma cells by combining cellular ALK gene silencing and a low dose of the kinase inhibitor U0126. Cancer Gene Ther 2010; 17(9):633-44
13. Shu D, Pi F, Wang C, et al. New approach to develop ultra-high inhibitory drug using the power-function of the stoichiometry of the targeted nanomachine or biocomplex. Nanomedicine 2015; 10:1881-97
** This is the first research article which suggested and proved the concept that targeting nanomachine or biocomplex with high stoichiometry for potent drug development.
14. Fang H, Zhang P. Huang L P, et al. Binomial distribution for quantification of protein subunits in biological nanoassemblies and functional nanomachines. Nanomedicine 2014; 10:1433-40
15. Fang H, Jing P, Haque F, Guo P. Role of channel Lysines and "Push Through A One-way Valve" Mechanism of Viral DNA packaging Motor. Biophysical Journal 2012; 102:127-35
16. Guo P. Zhang C, Chen C, et al. Inter-RNA interaction of phage phi29 pRNA to form a hexameric complex for viral DNA transportation. Mol Cell 1998; 2:149-55
17. Hugel T, Michaelis J, Hetherington C L, et al. Experimental test of connector rotation during DNA packaging into bacteriophage phi29 capsids. Plos Biology 2007; 5:558-67
18. Xiao F, Moll D, Guo S, Guo P. Binding of pRNA to the N-terminal 14 amino acids of connector protein of bacterial phage phi29. Nucleic Acids Res 2005; 33:2640-9
19. Guo P. Peterson C. Anderson D. Prohead and DNA-gp3-dependent ATPase activity of the DNA packaging protein gp16 of bacteriophage phi29. J Mol Biol 1987; 197:229-36
20. Schwartz C, De Donatis G M, Fang H, Guo P. The ATPase of the phi29 DNA-packaging motor is a member of the hexameric AAA+ superfamily. Virology 2013; 443:20-7
* This article confirmed that the ATPase of phi29 DNA packaging motor is a hexamer complex.
21. Zhang H. Schwartz C. De Donatis G M, Guo P. "Push Through One-Way Valve" Mechanism of Viral DNA Packaging. Adv Virus Res 2012; 83:415-65
22. Trottier M, Guo P. Approaches to determine stoichiometry of viral assembly components. J Virol 1997; 71:487-94
23. Schwartz C. De Donatis G M, Zhang H, et al. Revolution rather than rotation of AAA+ hexameric phi29 nanomotor for viral dsDNA packaging without coiling. Virology 2013; 443:28-39
24. Zhao Z, Khisamutdinov E, Schwartz C, Guo P. Mechanism of one-way traffic of hexameric phi29 DNA packaging motor with four electropositive relaying layers facilitating anti-parallel revolution. ACS Nano 2013; 7:4082-92
25. Guo P, Schwartz C, Haak J, Zhao Z. Discovery of a new motion mechanism of biomotors similar to the earth revolving around the sun without rotation. Virology 2013; 446:133-43
26. Guo P, Grainge I, Zhao Z, Vieweger M. Two classes of nucleic acid translocation motors: rotation and revolution without rotation. Cell Biosci 2014; 4:54
27. De-Donatis G, Zhao Z, Wang S, et al. Finding of widespread viral and bacterial revolution dsDNA translocation motors distinct from rotation motors by channel chirality and size. Cell Biosci 2014; 4:30
** This review reported that revolution biomotors are widespread in biological systems. This new approach for targeting nanomotor for potent drug development should have broad applications.
28. Wolfe A. Phipps K, Weitao T. Viral and cellular SOS-regulated motor proteins: dsDNA translocation mechanisms with divergent functions. Cell Biosci 2014; 4:31
29. Guo P, Peterson C, Anderson D. Initiation events in in vitro packaging of bacteriophage phi29 DNA-gp3. J Mol Biol 1987; 197:219-28
30. Sperlagh B, Illes P. P2X7 receptor: an emerging target in central nervous system diseases. Trends Pharmacol Sci 2014; 35:537-47
31. Schiebel J. Chang A, Shah S, et al. Rational Design of Broad Spectrum Antibacterial Activity Based on a Clinically Relevant Enoyl-Acyl Carrier Protein (ACP) Reductase Inhibitor. J Biol Chem 2014:289:15987-6005
32. Whitby F G, Luecke H, Kuhn P, et al. Crystal structure of *Tritrichomonas foetus* inosine-5'-monophosphate dehydrogenase and the enzyme-product complex. Biochemistry 1997; 36:10666-74
33. Casjens S R. The DNA-packaging nanomotor of tailed bacteriophages. Nat Rev Microbiol 2011; 9:647-57
34. Guo P. Zhao Z, Haak J. et al. Common Mechanisms of DNA translocation motors in Bacteria and Viruses Using One-way Revolution Mechanism without Rotation. Biotechnology Advances 2014; 32:853-72
35. Buskin S E, Zhang S. Thibault C S. Prevalence of and viral outcomes associated with primary HIV-1 drug resistance. Open AIDS J 2012; 6:181-7
36. Boal A K, Ilhan F, DeRouchey J E, et al. Self-assembly of nanoparticles into structured spherical and network aggregates. Nature 2000; 404:746-8
37. Holohan C, Van S S, Longley D B, Johnston P G. Cancer drug resistance: an evolving paradigm. Nat Rev Cancer 2013; 13:714-26
38. Hanson P I, Whiteheart S W. AAA+ proteins: have engine, will work. Nat Rev Mol Cell Biol 2005; 6:519-29
39. Lee C S, Guo P. Sequential interactions of structural proteins in phage phi29 procapsid assembly. J Virol 1995; 69:5024-32

40. Stitt B L, Xu Y. Sequential hydrolysis of ATP molecules bound in interacting catalytic sites of *Escherichia coli* transcription termination protein Rho. J Biol Chem 1998; 273:26477-86
41. Persechini A. Hartshorne D J. Cooperative behavior of smooth muscle myosin. Fed Proc 1982; 41:2868-72
42. Lisal J, Tuma R. Cooperative mechanism of RNA packaging motor. J Biol Chem 2005; 280:23157-64
43. Andrews B T, Catalano C E. Strong subunit coordination drives a powerful viral DNA packaging motor. Proc Natl Acad Sci USA 2013; 110:5909-14
44. Zhang H, Shu D, Huang F, Guo P. Instrumentation and metrology for single RNA counting in biological complexes or nanoparticles by a single molecule dual-view system. RNA 2007; 13:1793-802
45. Chen C, Trottier M, Guo P. New approaches to stoichiometry determination and mechanism investigation on RNA involved in intermediate reactions. Nucleic Acids Symposium Series 1997:36:190-3
46. Chen C, Guo P. Sequential action of six virus-encoded DNA-packaging RNAs during phage phi29 genomic DNA translocation. J Virol 1997; 71:3864-71
47. Kammerer R A, Schulthess T, Landwehr R, et al. Tenascin-C hexabrachion assembly is a sequential two-step process initiated by coiled-coil alpha-helices. J Biol Chem 1998; 273:10602-8
48. Zhang Z, Lewis D, Strock C, et al. Detailed characterization of the cooperative mechanism of Ca(2+) binding and catalytic activation in the Ca(2+) transport (SERCA) ATPase. Biochemistry 2000; 39:8758-67
49. Sun H, Squier T C. Ordered and cooperative binding of opposing globular domains of calmodulin to the plasma membrane Ca-ATPase. J Biol Chem 2000; 275:1731-8
50. Hiller R, Carmeli C. Kinetic analysis of cooperative interactions induced by Mn2+ binding to the chloroplast H(+)-ATPase. Biochemistry 1990; 29:6186-92
51. Casjens S, Hendrix R. Control mechanisms in dsDNA bacteriophage assembly. In: Calendar R, editor. The Bacteriophages Vol. 1. New York: Plenum Publishing Corp., 1988. p. 15-92.
52. Qian X, Ren Y. Shi Z. et al. Sequence-dependent synergistic inhibition of human glioma cell lines by combined temozolomide and miR-21 inhibitor gene therapy. Mol Pharm 2012; 9:2636-45
53. Gillman S, Gillard M, Strolin B M. The concept of receptor occupancy to predict clinical efficacy: a comparison of second generation H1 antihistamines. Allergy Asthma Proc 2009; 30:366-76
54. Shu D, Zhang H, Jin J, Guo P. Counting of six pRNAs of phi29 DNA-packaging motor with customized single molecule dual-view system. EMBO J 2007; 26:527-37
* This article confirmed the stoichiometry of pRNA in phi29 DNA packaging motor is six by single fluorophore photo bleaching method.
55. Lee C S, Guo P. A highly sensitive system for the assay of in vitro viral assembly of bacteriophage phi29 of *Bacillus subtilis*. Virology 1994; 202:1039-42
56. Shu Y, Haque F, Shu D, et al. Fabrication of 14 Different RNA Nanoparticles for Specific Tumor Targeting without Accumulation in Normal Organs. RNA 2013; 19:766-77
57. Shu Y. Shu D, Haque F. Guo P. Fabrication of pRNA nanoparticles to deliver therapeutic RNAs and bioactive compounds into tumor cells. Nat Protoc 2013; 8:1635-59
58. Zhang H, Endrizzi J A, Shu Y, et al. Crystal Structure of 3WJ Core Revealing Divalent Ion-promoted Thermostability and Assembly of the Phi29 Hexameric Motor pRNA. RNA 2013; 19:1226-37
59. Schwartz C, Fang H, Huang L, Guo P. Sequential action of ATPase, ATP, ADP, Pi and dsDNA in procapsid-free system to enlighten mechanism in viral dsDNA packaging. Nucleic Acids Res 2012; 40:2577-86
60. Han W, Shen Y, She Q. Nanobiomotors of archaeal DNA repair machineries: current research status and application potential. Cell Biosci 2014; 4:32
61. Swuec P, Costa A. Molecular mechanism of double Holliday junction dissolution. Cell Biosci 2014; 4:36
62. Happonen L J, Erdmann S, Garrett R A, Butcher S J. Adenosine triphosphatases of thermophilic archaeal double-stranded DNA viruses. Cell Biosci 2014; 4:37
63. Junge W, Lill H, Engelbrecht S. ATP synthase: an electrochemical transducer with rotatory mechanics. Trends in Biochemical Sciences 1997; 22:420-3
64. DeRosier D J. The turn of the screw: the bacterial flagellar motor. Cell 1998; 93:17-20
65. Yoshida M, Muneyuki E, Hisabori T. ATP synthase—a marvellous rotary engine of the cell. Nat Rev Mol Cell Biol 2003; 2(9):669-77
66. Okuno D, Iino R, Noji H. Rotation and structure of FoF1-ATP synthase. Journal of Biochemistry 2011; 149: 655-64
67. Kaplan D L, Steitz T A. DnaB from *Thermus aquaticus* unwinds forked duplex DNA with an asymmetric tail length dependence. J Biol Chem 1999; 274:6889-97
68. LeBowitz J H, McMacken R. The *Escherichia coli* dnaB replication protein is a DNA helicase. The Journal of Biological Chemistry 1986; 261:4738-48
69. Itsathitphaisam O, Wing R A, Eliason W K, et al. The hexameric helicase DnaB adopts a nonplanar conformation during translocation. Cell 2012; 151:267-77
70. Thomsen N D, Berger J M. Running in reverse: the structural basis for translocation polarity in hexameric helicases. Cell 2009; 139:523-34
71. Di C E, Engel A, Stasiak A, Koller T. Characterization of complexes between recA protein and duplex DNA by electron microscopy. J Mol Biol 1982; 157:87-103
72. VanLoock M S, Yu X, Yang S X, et al. ATP-Mediated conformational changes in the RecA filament. Structure 2003; 11:187-96
73. Ammelburg M, Frickey T. Lupas A N. Classification of AAA+ proteins. J Struct Biol 2006; 156:2-11
74. Guo P X, Lee T J. Viral nanomotors for packaging of dsDNA and dsRNA. Mol Microbiol 2007; 64:886-903
75. Snider J, Houry W A. AAA+ proteins: diversity in function, similarity in structure. Biochemical Society Transactions 2008; 36:72-7
76. Snider J, Thibault G, Houry W A. The AAA+ superfamily of functionally diverse proteins. Genome Biol 2008; 9:216
77. Chemla Y R, Aathavan K, Michaelis J, et al. Mechanism of force generation of a viral DNA packaging motor. Cell 2005; 122:683-92
78. Hwang Y, Catalano C E, Feiss M. Kinetic and mutational dissection of the two ATPase activities of terminase, the DNA packaging enzyme of bacteriophage lambda. Biochemistry 1996; 35:2796-803
79. Guenther B, Onrust R, Sali A, et al. Crystal structure of the delta' subunit of the clamp-loader complex of *E. coli* DNA polymerase III. Cell 1997; 91:335-45
80. McNally R, Bowman G D, Goedken E R, et al. Analysis of the role of PCNA-DNA contacts during clamp loading. BMC Struct Biol 2010; 10:3
81. Aussel L, Barre F X, Aroyo M, et al. FtsK is a DNA motor protein that activates chromosome dimer resolution by switching the catalytic state of the XerC and XerD recombinases. Cell 2002; 108:195-205

82. Barre F X, Aroyo M, Colloms S D, et al. FtsK functions in the processing of a Holliday junction intermediate during bacterial chromosome segregation. Genes Dev 2000; 14:2976-88

83. Yu X C, Weihe E K, Margolin W. Role of the C terminus of FtsK in *Escherichia coli* chromosome segregation. J Bacteriol 1998; 180:6424-8

84. Burton B, Dubnau D. Membrane-associated DNA transport machines. Cold Spring Harb Perspect Biol 2010; 2:a000406

85. Pease P J, Levy O, Cost G J, et al. Sequence-directed DNA translocation by purified FtsK. Science 2005; 307:586-90

86. Crozat E, Grainge I. FtsK DNA translocase: the fast motor that knows where it's going. Chembiochem 2010; 11:2237-43

87. Massey T H, Mercogliano C P, Yates J, et al. Double-stranded DNA translocation: structure and mechanism of hexameric FtsK. Mol Cell 2006; 23:457-69

88. Lowe J. Ellonen A, Allen M D, et al. Molecular mechanism of sequence-directed DNA loading and translocation by FtsK. Mol Cell 2008; 31:498-509

89. Casado V, Cortes A, Mallol J, et al. GPCR homomers and heteromers: a better choice as targets for drug development than GPCR monomers? Pharmacol Ther 2009; 124:248-57

90. Makowska-Grzyska M, Kim Y, Maltseva N, et al. A novel cofactor-binding mode in bacterial IMP dehydrogenases explains inhibitor selectivity. J Biol Chem 2015; 290:5893-911

91. Murakami S, Nakashima R, Yamashita E, Yamaguchi A. Crystal s of bacterial multidrug efflux transporter AcrB. Nature 2002; 419:587-93

92. Sennhauser G, Bukowska M A, Briand C, Grutter M G. Crystal structure of the multidrug exporter MexB from *Pseudomonas aeruginosa*. J Mol Biol 2009; 389:134-45

93. Hu S, Chen Z, Franke R, et al. Interaction of the multikinase inhibitors sorafenib and sunitinib with solute carriers and ATP-binding cassette transporters. Clin Cancer Res 2009; 15:6062-9

94. Ziolo M T, Martin J L, Bossuyt J, et al. Adenoviral gene transfer of mutant phospholamban rescues contractile dysfunction in failing rabbit myocytes with relatively preserved SERCA function. Circ Res 2005; 96:815-7

95. Aker J, Hesselink R, Engel R, et al. In vivo hexamerization and characterization of the *Arabidopsis* AAA ATPase CDC48A complex using forster resonance energy transfer-fluorescence lifetime imaging microscopy and fluorescence correlation spectroscopy. Plant Physiology 2007; 145:339-50

96. White S R, Lauring B. AAA+ ATPases: Achieving diversity of function with conserved machinery. Traffic 2007; 8:1657-67

97. Willows R D, Hansson A, Birch D, et al. EM single particle analysis of the ATP-dependent BchI complex of magnesium chelatase: an AAA(+) hexamer. J Struct Biol 2004; 146:227-33

98. Iyer L M, Leipe D D, Koonin E V, Aravind L Evolutionary history and higher order classification of AAA plus ATPases. J Struct Biol 2004; 146:11-31

99. Liu Y. Huang T, MacMorris M, Blumenthal T. Interplay between AAUAAA and the trans-splice site in processing of a *Caenorhabditis elegans* operon pre-mRNA. RNA 2001; 7:176-81

100. Watanabe R, Matsukage Y, Yukawa A, et al. Robustness of the Rotary Catalysis Mechanism of F-1-ATPase. J Biol Chem 2014; 289:19331-40

101. Yasuda R, Noji H, Kinosita K, Jr., Yoshida M. F1-ATPase is a highly efficient molecular motor that rotates with discrete 120 degree steps. Cell 1998:93:1117-24

102. Kinosita K, Jr., Yasuda R, Noji H, et al. F1-ATPase: a rotary motor made of a single molecule. Cell 1998; 93:21-4

103. Stock D, Leslie A G, Walker J E. Molecular architecture of the rotary motor in ATP synthase. Science 1999; 286:1700-5

104. Boyer P D. What makes ATP synthase spin? Nature 1999; 402:247-9

105. Adachi K, Yasuda R, Noji H, et al. Stepping rotation of F1-ATPase visualized through angle-resolved single-fluorophore imaging. Proc Natl Acad Sci USA 2000; 97:7243-7

106. Hara K Y, Noji H, Bald D, et al. The role of the DELSEED motif of the beta subunit in rotation of F1-ATPase. J Biol Chem 2000; 275:14260-3

107. Masaike T, Mitome N, Noji H, et al. Rotation of F(1)-ATPase and the hinge residues of the beta subunit. J Exp Biol 2000; 203 Pt 1:1-8

108. Wada Y, Sambongi Y, Futai M. Biological nano motor. ATP synthase F(o)F(1): from catalysis to gammaepsilonc (10-12) subunit assembly rotation. Biochim Biophys Acta 2000; 1459:499-505

109. Okazaki K, Hummer G. Phosphate release coupled to rotary motion of F-1-ATPase. Proceedings of the National Academy of Sciences of the United States of America 2013; 110:16468-73

110. Ito Y, Yoshidome T, Matubayasi N, et al. Molecular Dynamics Simulations of Yeast F-1-ATPase before and after 16 degrees Rotation of the gamma Subunit. Journal of Physical Chemistry B 2013; 117:3298-307

111. Arai H C, Yukawa A, Iwatate R J, et al. Torque Generation Mechanism of F-1-ATPase upon NTP Binding. Biophysical Journal 2014; 107:156-64

112. Trottier M, Zhang C L, Guo P. Complete inhibition of virion assembly in vivo with mutant pRNA essential for phage phi29 DNA packaging. J Virol 1996; 70:55-61

113. Sprowl J A, Ciarimboli G, Lancaster C S, et al. Oxaliplatin-induced neurotoxicity is dependent on the organic cation transporter OCT2. Proc Natl Acad Sci USA 2013; 110:11199-204

114. Furmanski B D, Hu S, Fujita K. et al. Contribution of ABCC4-mediated gastric transport to the absorption and efficacy of dasatinib. Clin Cancer Res 2013; 19:4359-70

APPENDIX E

Tables in this Appendix Correspond to the Tables Set Forth in Paragraphs Section 2

| Inhibited Subunits (p) | Z = 1 | | Z = 6 | | | | | | |
|---|---|---|---|---|---|---|---|---|---|
| | M = 0, N = 1 | M = 1, N = 0 | M = 0, N = 6 | M = 1, N = 5 | M = 2, N = 4 | M = 3, N = 3 | M = 4, N = 2 | M = 5, N = 1 | M = 6, N = 0 |
| 0% | 100% | 0% | 100% | 0% | 0% | 0% | 0% | 0% | 0% |
| 10% | 90% | 9% | 53% | 35% | 10% | 1% | 0% | 0% | 0% |
| 20% | 80% | 16% | 26% | 39% | 25% | 8% | 2% | 0% | 0% |
| 30% | 70% | 21% | 12% | 30% | 32% | 19% | 6% | 1% | 0% |
| 40% | 60% | 24% | 5% | 19% | 31% | 28% | 14% | 4% | 0% |
| 50% | 50% | 25% | 2% | 9% | 23% | 31% | 23% | 9% | 2% |
| 60% | 40% | 24% | 0% | 4% | 14% | 28% | 31% | 19% | 5% |
| 70% | 30% | 21% | 0% | 1% | 6% | 19% | 32% | 30% | 12% |
| 80% | 20% | 16% | 0% | 0% | 2% | 8% | 25% | 39% | 26% |
| 90% | 10% | 9% | 0% | 0% | 0% | 1% | 10% | 35% | 53% |
| 100% | 0% | 0% | 0% | 0% | 0% | 0% | 0% | 0% | 100% |

APPENDIX F

Tables in this Appendix Correspond to the Tables Set Forth in Paragraphs Section 3

TABLE 1

| Inhibited Subunits (p) | Z = 3 | | | | Z = 12 | | | | |
|---|---|---|---|---|---|---|---|---|---|
| | M = 0, N = 3 | M = 1, N = 2 | M = 2, N = 1 | M = 3, N = 0 | M = 0, N = 12 | M = 1, N = 11 | M = 2, N = 10 | M = 3, N = 9 | M = 4, N = 8 |
| 0 | 1.0000 | 0.0000 | 0.0000 | 0.0000 | 1.0000 | 0.0000 | 0.0000 | 0.0000 | 0.0000 |
| 0.1 | 0.7290 | 0.2430 | 0.0270 | 0.0010 | 0.2824 | 0.3766 | 0.2301 | 0.0652 | 0.0219 |
| 0.2 | 0.5120 | 0.3840 | 0.0960 | 0.0080 | 0.0687 | 0.2062 | 0.2835 | 0.2362 | 0.1329 |
| 0.3 | 0.3430 | 0.4410 | 0.1890 | 0.0270 | 0.0138 | 0.0712 | 0.1678 | 0.2397 | 0.2311 |
| 0.4 | 0.2160 | 0.4320 | 0.2880 | 0.0640 | 0.0022 | 0.0174 | 0.0619 | 0.1419 | 0.2128 |
| 0.5 | 0.1250 | 0.3750 | 0.3750 | 0.1250 | 0.0002 | 0.0029 | 0.0161 | 0.0537 | 0.1208 |
| 0.6 | 0.0640 | 0.2880 | 0.4320 | 0.2160 | 0.0000 | 0.0003 | 0.0025 | 0.0125 | 0.0420 |
| 0.7 | 0.0270 | 0.1890 | 0.4410 | 0.3430 | 0.0000 | 0.0000 | 0.0002 | 0.0015 | 0.0078 |
| 0.8 | 0.0080 | 0.0960 | 0.3540 | 0.5120 | 0.0000 | 0.0000 | 0.0000 | 0.0001 | 0.0005 |
| 0.9 | 0.0010 | 0.0270 | 0.2430 | 0.7290 | 0.0000 | 0.0000 | 0.0000 | 0.0000 | 0.0000 |
| 1 | 0.0000 | 0.0000 | 0.0000 | 1.0000 | 0.0000 | 0.0000 | 0.0000 | 0.0000 | 0.0000 |

| Inhibited Subunits (p) | Z = 12 | | | | | | |
|---|---|---|---|---|---|---|---|
| | M = 5, N = 7 | M = 6, N = 6 | M = 7, N = 5 | M = 8, N = 4 | M = 9, N = 3 | M = 10, N = 2 | M = 11, N = 1 | M = 12, N = 0 |
| 0 | 0.0000 | 0.0000 | 0.0000 | 0.0000 | 0.0000 | 0.0000 | 0.0000 | 0.0000 |
| 0.1 | 0.0038 | 0.0005 | 0.0000 | 0.0000 | 0.0000 | 0.0000 | 0.0000 | 0.0000 |
| 0.2 | 0.0532 | 0.0155 | 0.0033 | 0.0005 | 0.0001 | 0.0000 | 0.0000 | 0.0000 |
| 0.3 | 0.1585 | 0.0792 | 0.0291 | 0.0078 | 0.0015 | 0.0002 | 0.0000 | 0.0000 |
| 0.4 | 0.2270 | 0.1766 | 0.1009 | 0.0420 | 0.0125 | 0.0025 | 0.0003 | 0.0000 |
| 0.5 | 0.1934 | 0.2256 | 0.1934 | 0.1208 | 0.0537 | 0.0161 | 0.0029 | 0.0002 |
| 0.6 | 0.1009 | 0.1766 | 0.2270 | 0.2128 | 0.1419 | 0.0639 | 0.0174 | 0.0022 |
| 0.7 | 0.0291 | 0.0792 | 0.1585 | 0.2311 | 0.2397 | 0.1678 | 0.0712 | 0.0138 |
| 0.8 | 0.0033 | 0.0155 | 0.0532 | 0.1329 | 0.2362 | 0.2835 | 0.2062 | 0.0687 |
| 0.9 | 0.0000 | 0.0005 | 0.0038 | 0.0213 | 0.0832 | 0.2301 | 0.3766 | 0.2524 |
| 1 | 0.0000 | 0.0000 | 0.0000 | 0.0000 | 0.0000 | 0.0000 | 0.0000 | 1.0000 |

TABLE 2

Predicted inhibition efficiency of drugs targeting biocomplexes, K = 1

| Drugged subunit (p) | Inhibition efficiency of the multi-subunit complex with | | | | | | |
|---|---|---|---|---|---|---|---|
| | Z = 1 | Z = 2 | Z = 3 | Z = 6 | Z = 10 | Z = 100 | Z = 1000 |
| 0 | 0.0000 | 0.0000 | 0.0000 | 0.0000 | 0.0000 | 0.0000 | 0.0000 |
| 0.1 | 0.1000 | 0.1900 | 0.2710 | 0.4686 | 0.6513 | 1.0000 | 1.0000 |
| 0.2 | 0.2000 | 0.3600 | 0.4880 | 0.7379 | 0.8926 | 1.0000 | 1.0000 |
| 0.3 | 0.3000 | 0.5100 | 0.6570 | 0.8824 | 0.9718 | 1.0000 | 1.0000 |
| 0.4 | 0.4000 | 0.6400 | 0.7840 | 0.9533 | 0.9940 | 1.0000 | 1.0000 |
| 0.5 | 0.5000 | 0.7500 | 0.8750 | 0.9844 | 0.9990 | 1.0000 | 1.0000 |
| 0.6 | 0.6000 | 0.8400 | 0.9360 | 0.9959 | 0.9999 | 1.0000 | 1.0000 |
| 0.7 | 0.7000 | 0.9100 | 0.9730 | 0.9993 | 1.0000 | 1.0000 | 1.0000 |
| 0.8 | 0.8000 | 0.9600 | 0.9920 | 0.9999 | 1.0000 | 1.0000 | 1.0000 |
| 0.9 | 0.9000 | 0.9900 | 0.9990 | 1.0000 | 1.0000 | 1.0000 | 1.0000 |
| 1 | 1.0000 | 1.0000 | 1.0000 | 1.0000 | 1.0000 | 1.0000 | 1.0000 |

TABLE 3

Comparison of proportion of non-inhibited complex between Z = 6 and Z = 1 when K = 1 but having equal drug targeting efficacy

| Substrate targeting efficacy (p) | Proportion of non-inhibited complex from the population with Z = 6 | Proportion of non-inhibited complex from the population with Z = 1 | Ratio of the proportions of non-inhibited complex from the two populations with Z = 6 and Z = 1 | Reduction (fold) in proportion of non-inhibited complex comparing Z = 6 and Z = 1 |
|---|---|---|---|---|
| 0 | 1 | 1 | 1 | 1 |
| 0.1 | 0.5314 | 0.9 | 0.5905 | 1.7 |
| 0.2 | 0.2621 | 0.8 | 0.3277 | 3.1 |
| 0.3 | 0.1176 | 0.7 | 0.1681 | 5.9 |
| 0.4 | 0.0467 | 0.6 | 0.0778 | 12.9 |
| 0.5 | 0.0156 | 0.5 | 0.0312 | 32 |
| 0.6 | 0.0041 | 0.4 | 0.0102 | 98 |
| 0.7 | 7E−04 | 0.3 | 0.0024 | 416 |
| 0.8 | 1E−04 | 0.2 | 0.0003 | 3333 |
| 0.9 | 1E−06 | 0.1 | 1E−05 | 10000 |

What is claimed is:

1. A method for the identification of multi-subunit biocomplex drug targets, the method comprising, identifying a target that performs a biological function, wherein the target comprises one or more subunits, wherein a minimum number (K) of the one or more subunits is inactivated (M) to inhibit the biological function;

selecting a drug that binds specifically to each subunit of the one or more subunits with a target probability (p), wherein the target probability comprises a common probability for each subunit that the drug delivered to the target inactivates the subunit;

describing a relationship between inhibition efficiency of the drug and total number (Z) of the one or more subunits using a binomial distribution, wherein the inhibition efficiency comprises a probability that the delivered drug blocks the biological function, wherein the inhibition efficiency is computed with respect to the minimum number and the total number;

confirming empirically the relationship using an experimental target, wherein the target includes the experimental target;

administering the drug to the target to treat a multi-drug resistant disease, wherein the target comprises a biological complex in a mammalian subject.

2. The method of claim 1, wherein variable N represents an active subunit of the one or more subunits, wherein Z=M+N.

3. The method of claim 1, wherein q=1−p.

4. The method of claim 3, wherein a probability that the target includes M inactivated subunits and N active units is given by the binomial expression $$\frac{(Z!)}{(N!)(M!)} p^M q^N.$$

5. The method of claim 4, wherein the inhibition efficiency is given by the binomial equation $$\sum_{M=1}^{Z} \left( \frac{Z!}{M!(Z-M)!} \right) p^M q^{Z-M}.$$

6. The method of claim 5, wherein K=1 and Z>1.

7. The method of claim 6, wherein the inhibition efficiency is given by $1-q^Z$.

8. The method of claim 1, wherein the experimental target comprises a component or subunit of a multimeric biocomplex or a biological nanomotor.

9. The method of claim 8, wherein the nanomotor comprises a linear motor, a rotation motor, or a revolution motor.

10. The method of claim 8, wherein the nanomotor comprises an ATPase component.

11. The method of claim 8, wherein the multimeric biocomplex comprises a receptor, a channel, an enzyme, or a transporter.

12. The method of claim 8, wherein the multimeric biocomplex comprises a homomeric biocomplex.

13. The method of claim 8, wherein the multimeric biocomplex comprises a dimer, a hetero-oligomer, or a homo-oligomer.

14. The method of claim 8, wherein the number of components or subunits is at least 2, 3, 4, 5, 6, 7, 8, 9, 10, 11, or 12.

15. The method of claim 8, wherein the nanomotor is a bacteriophage Phi29 DNA packaging motor.

16. The method of claim 15, wherein the bacteriophage Phi29 DNA packaging motor comprises a genomic dsDNA component, a packaging RNA component, an ATPase gp16 component, an ATP component, or a combination thereof.

17. The method of claim 16, wherein each Phi29 DNA packaging motor component comprises the experimental target.

18. The method of claim 15, wherein the bacteriophage Phi29 DNA packaging motor comprises 1 copy of genomic dsDNA, and wherein the copy comprises a subunit.

19. The method of claim 15, wherein the bacteriophage Phi29 DNA packaging motor comprises 6 copies of packaging RNA, and wherein the copies comprise subunits.

20. The method of claim 15, wherein the bacteriophage Phi29 DNA packaging motor comprises 6 copies of gp16, and wherein the copies comprise subunits.

21. The method of claim 15, wherein the bacteriophage Phi29 DNA packaging motor comprises 10,000 copies of ATP, and wherein the copies comprise subunits.

22. The method of claim 1, wherein the multi-drug resistant disease is caused by a multidrug-resistant organism.

23. The method of claim 22, wherein the multidrug-resistant organism is a bacterium, a fungus, a virus, or a parasite.

24. A method for increasing inhibition efficiency of a multimeric biocomplex, the method comprising,
identifying a target that performs a biological function, wherein the target comprises one or more subunits, wherein a minimum number of the one or more subunits is inactivated to inhibit the biological function;
selecting a drug that binds specifically to each subunit of the one or more subunits with a target probability, wherein the target probability comprises a common probability for each subunit that the drug delivered to the target inactivates the subunit;
describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number;
confirming empirically the relationship using an experimental target, wherein the target includes the experimental target;
administering the drug to the target to treat a multi-drug resistant disease, wherein the target comprises a biological complex in a mammalian subject.

25. A method for treating a subject afflicted with a multi-drug resistant disease, the method comprising,
identifying a target that performs a biological function, wherein the target comprises one or more subunits, wherein a minimum number of the one or more subunits is inactivated to inhibit the biological function;
selecting a drug that binds specifically to each subunit of the one or more subunits with a target probability, wherein the target probability comprises a common probability for each subunit that the drug delivered to the target inactivates the subunit;
describing a relationship between inhibition efficiency of the drug and total number of the one or more subunits using a binomial distribution, wherein the inhibition efficiency comprises a probability that the delivered drug blocks the biological function, wherein the inhibition efficiency is computed with respect to the minimum number and the total number;
confirming empirically the relationship using an experimental target, wherein the target includes the experimental target;
administering the drug to the target to treat a multi-drug resistant disease, wherein the target comprises a biological complex in a mammalian subject.

* * * * *